US010093673B2

United States Patent
Fu et al.

(10) Patent No.: US 10,093,673 B2
(45) Date of Patent: *Oct. 9, 2018

(54) TETRACYCLIC PYRIDONE COMPOUNDS AS ANTIVIRALS

(71) Applicant: Novartis AG, Basel (CH)

(72) Inventors: Jiping Fu, Danville, CA (US); Xianming Jin, San Ramon, CA (US); Patrick Lee, Walnut Creek, CA (US); Peichao Lu, Pleasant Hill, CA (US); Joseph Michael Young, Castro Valley, CA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/782,722

(22) Filed: Oct. 12, 2017

(65) Prior Publication Data

US 2018/0030053 A1 Feb. 1, 2018

Related U.S. Application Data

(63) Continuation of application No. 15/435,137, filed on Feb. 16, 2017, now Pat. No. 9,845,325.

(60) Provisional application No. 62/434,658, filed on Dec. 15, 2016, provisional application No. 62/297,590, filed on Feb. 19, 2016.

(51) Int. Cl.
   *C07D 491/147* (2006.01)
   *C07D 471/14* (2006.01)
   *A61K 31/4375* (2006.01)
   *C07D 217/08* (2006.01)
   *C07D 491/14* (2006.01)

(52) U.S. Cl.
   CPC ........ *C07D 471/14* (2013.01); *A61K 31/4375* (2013.01); *C07D 217/08* (2013.01); *C07D 491/14* (2013.01); *C07D 491/147* (2013.01)

(58) Field of Classification Search
   CPC .............. C07D 491/147; C07D 471/14; A61K 31/4375
   USPC ........................................................... 546/1
   See application file for complete search history.

(56) References Cited

U.S. PATENT DOCUMENTS 9,845,325 B2 * 12/2017 Fu ..................... C07D 471/14
2015/0252057 A1   9/2015 Guo et al.

FOREIGN PATENT DOCUMENTS

| CN | 106928215 A     | 7/2017  |
|----|-----------------|---------|
| CN | 106928245 A     | 7/2017  |
| WO | WO 2015/113990  | 8/2015  |
| WO | WO 2015/173164  | 11/2015 |
| WO | WO 2016/023877  | 2/2016  |
| WO | WO 2016/071215  | 5/2016  |
| WO | WO 2016/128335  | 8/2016  |
| WO | WO 2017/016921  | 2/2017  |
| WO | WO 2017/016960  | 2/2017  |
| WO | WO 2017/017042  | 2/2017  |
| WO | WO 2017/102648  | 6/2017  |
| WO | WO 2017/108630  | 6/2017  |
| WO | WO 2017/114812  | 7/2017  |
| WO | WO 2017/216685  | 12/2017 |
| WO | WO 2017/216686  | 12/2017 |

OTHER PUBLICATIONS

Ciupe et al., "Antibody Responses During Hepatitis B Viral Infection" PLOS 10(7):e1003730, Jul. 2014.

Dougherty et al., "A Substituted Tetrahydro-Tetrazolo-Pyrimidine Is a Specific and Novel Inhibitor of Hepatitis B Virus Surface Antigen SecretionV" Antimicrob. Agents Chemother. 51(12)4427-4437, Dec. 2007.

Gilbert et al., "Hepatitis B small surface antigen particles are octahedral" Proc. Natl. Acad Sci USA 102(41):14783-14788, Oct. 11, 2005.

Georgopapadakou et al. "Monocyclic and Tricyclic Analogs of Quinolones: Mechanism of Action" Antimicrobial Agents and Chemotherapy 31(4):614-616, 1987.

* cited by examiner

*Primary Examiner* — Niloofar Rahmani
(74) *Attorney, Agent, or Firm* — Mark H. Hopkins

(57) ABSTRACT

The invention provides compounds of Formula (I)

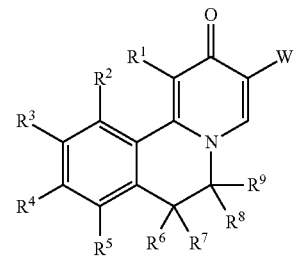

as described herein, along with pharmaceutically acceptable salts, pharmaceutical compositions containing such compounds, and methods to use these compounds, salts and compositions for treating viral infections, particularly infections caused by hepatitis B virus, and reducing the occurrence of serious conditions associated with HBV.

16 Claims, No Drawings

TETRACYCLIC PYRIDONE COMPOUNDS AS ANTIVIRALS

CROSS-REFERENCE TO RELATED APPLICATIONS

This is a continuation of U.S. Ser. No. 15/435,137, filed 16 Feb. 2017, which claims the benefit of priority to U.S. Provisional Application No. 62/297,590, filed 19 Feb. 2016 and U.S. Provisional Application No. 62/434,658, filed 15 Dec. 2016; the contents of these applications are incorporated herein by reference.

FIELD OF THE INVENTION

The present invention relates to novel tetracyclic pyridone compounds that are inhibitors of hepatitis virus replication, and are thus useful to treat viral infections, and particularly hepatitis B virus (HBV). The invention provides novel tetracyclic pyridone compounds as disclosed herein, pharmaceutical compositions containing such compounds, and methods of using these compounds and compositions in the treatment and prevention of HBV infections.

BACKGROUND

Globally, over 240 million people are chronically infected with hepatitis B virus (HBV), and more than 2 million reside in the United States alone. Of those chronically infected patients, up to 40 percent will eventually develop complications of liver failure from cirrhosis or development of hepatocellular carcinoma (HCC). Hepatitis B virus (HBV) belongs to the family of Hepadnaviridae, a group of small hepatotropic DNA viruses that replicate through the reverse transcription of an RNA intermediate. The 3.2-kb HBV genome in viral particles is in a circular, partially doublestranded DNA conformation (relaxed circular DNA or rcDNA). The HBV genome consists of four overlapping open reading frames (ORF), which encode for the core, polymerase (Pol), envelope, and X proteins. rcDNA is transcriptionally inert and must be converted into covalently closed circular DNA (cccDNA) in the nucleus of infected cells before viral RNAs can be transcribed. cccDNA is the only template for HBV transcription and, because HBV RNA templates genomic reverse transcription, its persistence is required for persistent infection.

The envelope of HBV comprises a mixture of surface antigen proteins (HBsAg). The HBsAg coat is a mixture of three overlapping proteins: all three share a common region, which corresponds to the smallest of the three proteins (SHBsAg). The mixture consists mostly of SHBsAg, but also includes Medium HBsAg, which comprises SHBsAg plus an additional polypeptide segment, and Large HBsAg, which comprises M HBsAg plus another added polypeptide segment. In addition to forming the infectious virion particle, the S, M and L HBsAg proteins also assemble into a subviral particle knows as the 22-nm particle, which is not infectious but contains the same proteins that envelope the infectious virus particles. Indeed, these subviral, non-infectious particles have been used as a vaccine, since they contain the same antigenic surface proteins that envelope the infectious HBV virion and thus elicit antibodies that recognize the infectious agent. Interestingly, these subviral particles greatly outnumber infectious virions, and are believed to protect the infectious virions from the immune system of the infected host. By sheer numbers, they may act as decoys, distracting immune responses from the infectious virus particles, but in addition they are reported to suppress the function of immune cells (monocytes, dendritic cells and natural killer cells) and may thus impair the immune response to HBV. Because these subviral particles protect infectious HBV from the host immune system, reducing the level of subviral particles has been recognized as a viable therapeutic approach. See, e.g., WO2015/113990.

One of the key diagnostic symptoms of chronic HBV is the high serum levels of the hepatitis B surface antigen (HBsAg). Clinical data in recent years suggest that sustained virologic response is often associated with on-treatment HBsAg decline during the early phase of the treatment as early as week 8, while sustained exposure to HBsAg and other viral antigens may lead to HBV-specific immune-tolerance. Chronic HB patients who experienced larger and faster decreases in serum HBsAg levels achieved significantly higher rate (~40%) of sustained virologic response as defined by sustained viral control post treatment.

Current treatment options for HBV include interferon therapies and nucleoside/nucleotide inhibitors of the viral DNA polymerase, such as entecavir and tenofovir. These focus on reduction in the level of viremia and toleration of hepatic dysfunction, and may have adverse side-effects and also select for drug-resistant virus variants during long term therapy. More importantly, these therapies cannot eradicate the intrahepatic HBV cccDNA pool in chronic hepatitis B patients or limit the transcription of HBsAg from the preexisting cccDNA, nor do they affect the secretion of synthesized HBsAg into patients' blood to counteract the host innate immune response. As a result, these HBV treatments are in most cases life-long therapy and discontinuation often leads to virological relapse. Some compounds have been reported to reduce serum HBsAg levels but so far have not resulted in new approved therapeutic agents. See for example WO2015/113990, WO2015/173164, WO2016/023877, WO2016/071215, and WO2016/128335.

Accordingly, there remains a need for more effective treatments for HBV, especially for treating chronic HBV infections. The invention provides compounds that are believed to operate by suppression of the secretion of the 22 nm subviral particles containing HBsAg. These compounds are useful to treat HBV infections and to reduce the incidence of serious liver disorders caused by HBV infections. They also exhibit improved properties relative to prior art compounds having similar biological activity, such as improved solubility in buffered aqueous systems and lower predicted propensity for certain adverse effects.

SUMMARY

The present invention provides novel compounds that inhibit secretion of HBsAg from cells infected with hepatitis B virus and thereby reduce viral load and viral replication in patients having chronic HBV infection. Some of the compounds of the invention, in addition to being highly effective at suppression of HBsAg levels, also exhibit improved safety relative to similar compounds known in the art, such as reduced inhibition of sodium ion channels that can be indicative of potential cardiotoxicity, reduced drug-drug interactions, and lower risk of time-dependent cytochrome (CYP) inhibition. Thus the compounds of the invention are suitable for treatment of patients with HBV. The invention also provides pharmaceutical compositions containing the novel compounds as well as methods to use the compounds and compositions to inhibit hepatitis B virus replication, and to treat disease conditions associated with or caused by HBV. Further objects of this invention are described in the following description and the examples.

In one aspect, the invention provides compounds of Formula (I):

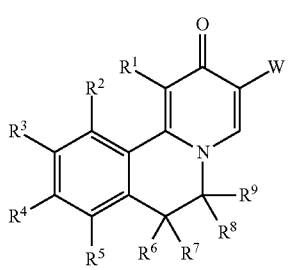

wherein:
R$^1$ is H, halo, or C$_1$-C$_3$ alkyl;
R$^2$ is H, halo, CN, C$_1$-C$_3$ alkyl or C$_1$-C$_3$ haloalkyl, C$_1$-C$_3$ alkoxy;
R$^3$ is OH, halo, CN, C$_1$-C$_3$ alkyl, C$_3$-C$_6$ cycloalkyl, C$_1$-C$_3$ haloalkyl, C$_1$-C$_3$ alkoxy, or C$_1$-C$_3$ haloalkoxy;
R$^4$ is selected from R$^{11}$, —OR$^{11}$, —SR$^{11}$, and —NRR$^{11}$;
R$^{11}$ is C$_1$-C$_4$ alkyl, C$_3$-C$_6$ cycloalkyl, oxetanyl, tetrahydrofuranyl, or tetrahydropyranyl, each of which is optionally substituted with up to three groups selected from halo, CN, —OR, C$_1$-C$_3$ haloalkoxy, and a 4-7 membered heterocyclic group containing one or two heteroatoms selected from N, O and S as ring members that is optionally substituted with one or two groups selected from halo, oxo, CN, R, —OR, and —NR$_2$;
R is independently selected at each occurrence from H and C$_1$-C$_3$ alkyl optionally substituted with one to three groups selected from halo, —OH, C$_1$-C$_3$ alkoxy, oxo, CN, —NH$_2$, —NH(C$_1$-C$_3$ alkyl), —N(C$_1$-C$_3$ alkyl)$_2$, and cyclopropyl;
and two R groups directly attached to a single atom can optionally be taken together to form a 3-6 membered ring that can optionally contain a heteroatom selected from N, O and S as a ring member, and can be substituted by up to two groups selected from —OH, oxo, C$_1$-C$_3$ alkyl, and C$_1$-C$_3$ alkoxy;
R$^5$ is H, halo, CN, C$_1$-C$_3$ alkyl, or C$_1$-C$_3$ haloalkyl;
R$^6$ is H, halo, C$_1$-C$_3$ alkoxy, or C$_1$-C$_6$ alkyl;
R$^7$ is H, halo, C$_1$-C$_3$ alkoxy, or C$_1$-C$_6$ alkyl;
R$^8$ is H or C$_1$-C$_6$ alkyl;
R$^9$ taken together with one group selected from R$^6$, R$^7$ and R$^8$ forms a 3-7 membered cycloalkyl ring or a 3-7 membered heterocyclic ring containing N, O or S as a ring member; wherein the cycloalkyl or heterocyclic ring is optionally substituted with up to three groups selected from R, —OR, —NR$_2$, halo, CN, COOR, CONR$_2$, and oxo;
W is —COOR$^{10}$, —C(O)NH—SO$_2$R, —C(O)NH—SO$_2$NR$_2$, 5-tetrazolyl, or 1,2,4-oxadiazol-3-yl-5(4H)-one;
R$^{10}$ is H or C$_1$-C$_6$ alkyl that is optionally substituted with one or two groups selected from halo, —OR, oxo, CN, —NR$_2$, COOR, and CONR$_2$;
or a pharmaceutically acceptable salt thereof.

DETAILED DESCRIPTION

For purposes of interpreting this specification, the following definitions will apply, and whenever appropriate, terms used in the singular will also include the plural.

Terms used in the specification have the following meanings unless the context clearly indicates otherwise:

As used herein, the term "subject" refers to an animal. In certain aspects, the animal is a mammal. A subject also refers to for example, primates (e.g., humans), cows, sheep, goats, horses, dogs, cats, rabbits, rats, mice, fish, birds and the like. In certain embodiments, the subject is a human. A "patient" as used herein refers to a human subject.

As used herein, the term "inhibition" or "inhibiting" refers to the reduction or suppression of a given condition, symptom, or disorder, or disease, or a significant decrease in the baseline activity of a biological activity or process.

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

"Optionally substituted" means the group referred to can be substituted at one or more positions by any one or any combination of the radicals listed thereafter. The number, placement and selection of substituents is understood to encompass only those substitutions that a skilled chemist would expect to be reasonably stable; thus 'oxo' would not be a substituent on an aryl or heteroaryl ring, for example, and a single carbon atom would not have three hydroxy or amino substituents. Unless otherwise specified, optional substituents are typically up to four groups selected from halo, oxo, CN, amino, hydroxy, —C$_{1-3}$ alkyl, —OR*, —NR*$_2$, —SR*, —SO$_2$R*, —COOR*, and —CONR*$_2$, where each R* is independently H or C$_{1-3}$ alkyl.

"Aryl" as used herein refers to a phenyl or naphthyl group unless otherwise specified. Aryl groups unless otherwise specified may be optionally substituted with up to four groups selected from halo, CN, amino, hydroxy, C$_{1-3}$ alkyl, —OR*, —NR*$_2$, —SR*, —SO$_2$R*, —COOR*, and —CONR*$_2$, where each R* is independently H or C$_{1-3}$ alkyl.

"Halo" or "halogen", as used herein, may be fluorine, chlorine, bromine or iodine.

"C$_{1-6}$ alkyl" or "C$_1$-C$_6$ alkyl", as used herein, denotes straight chain or branched alkyl having 1-6 carbon atoms. If a different number of carbon atoms is specified, such as C$_4$ or C$_3$, then the definition is to be amended accordingly, such as "C$_{1-4}$ alkyl" will represent methyl, ethyl, propyl, isopropyl, butyl, isobutyl, sec-butyl and tert-butyl.

"C$_{1-6}$ alkylene" or "C$_1$-C$_6$ alkylene", as used herein, denotes straight chain or branched alkyl having 1-6 carbon atoms and two open valences for connection to two other groups. If a different number of carbon atoms is specified, such as C$_4$ or C$_3$, then the definition is to be amended accordingly, such as "C$_{1-4}$ alkylene" will represent methylene (—CH$_2$—), ethylene (—CH$_2$CH$_2$—), straight chain or branched propylene (—CH$_2$CH$_2$CH$_2$— or —CH$_2$—CHMe-CH$_2$—), and the like.

"C$_{1-6}$ alkoxy", as used herein, denotes straight chain or branched alkoxy (—O-Alkyl) having 1-6 carbon atoms. If a different number of carbon atoms is specified, such as C$_4$ or C$_3$, then the definition is to be amended accordingly, such as "C$_{1-4}$ alkoxy" will represent methoxy, ethoxy, propoxy, isopropoxy, butoxy, isobutoxy, sec-butoxy and tert-butoxy.

"C$_{1-4}$ Haloalkyl" or "C$_1$-C$_4$ haloalkyl" as used herein, denotes straight chain or branched alkyl having 1-4 carbon atoms wherein at least one hydrogen has been replaced with a halogen. The number of halogen replacements can be from one up to the number of hydrogen atoms on the unsubstituted alkyl group. If a different number of carbon atoms is specified, such as C$_6$ or C$_3$, then the definition is to be amended accordingly. Thus "C$_{1-4}$ haloalkyl" will represent methyl, ethyl, propyl, isopropyl, butyl, isobutyl, sec-butyl and tert-butyl that have at least one hydrogen substituted with halogen, such as where the halogen is fluorine: CF$_3$CF$_2$—, (CF$_3$)$_2$CH—, CH$_3$—CF$_2$—, CF$_3$CF$_2$—, CF$_3$, CF$_2$H—, CF$_3$CF$_2$CH(CF$_3$)— or CF$_3$CF$_2$CF$_2$CF$_2$—.

"C$_{3-8}$ cycloalkyl" as used herein refers to a saturated monocyclic hydrocarbon ring of 3 to 8 carbon atoms. Examples of such groups include cyclopropyl, cyclobutyl, cyclopentyl and cyclohexyl. If a different number of carbon atoms is specified, such as C$_3$-C$_6$, then the definition is to be amended accordingly.

"4- to 8-Membered heterocyclyl", "5- to 6-membered heterocyclyl", "3- to 10-membered heterocyclyl", "3- to 14-membered heterocyclyl", "4- to 14-membered heterocyclyl" and "5- to 14-membered heterocyclyl", refers, respectively, to 4- to 8-membered, 5- to 6-membered, 3- to 10-membered, 3- to 14-membered, 4- to 14-membered and 5- to 14-membered heterocyclic rings; unless otherwise specified, such rings contain 1 to 7, 1 to 5, or 1 to 3 heteroatoms selected from the group consisting of nitrogen, oxygen and sulfur as ring members, and the rings may be saturated, or partially saturated but not aromatic. The heterocyclic group can be attached to another group at a nitrogen or a carbon atom. The term "heterocyclyl" includes single ring groups, fused ring groups and bridged groups. Examples of such heterocyclyl include, but are not limited to pyrrolidine, piperidine, piperazine, pyrrolidinone, morpholine, tetrahydrofuran, tetrahydrothiophene, tetrahydrothiopyran, tetrahydropyran, 1,4-dioxane, 1,4-oxathiane, 8-azabicyclo[3.2.1]octane, 3,8-diazabicyclo[3.2.1]octane, 3-Oxa-8-aza-bicyclo[3.2.1]octane, 8-Oxa-3-aza-bicyclo[3.2.1]octane, 2-Oxa-5-aza-bicyclo[2.2.1]heptane, 2,5-Diazabicyclo[2.2.1]heptane, azetidine, ethylenedioxo, oxetane or thiazole. In certain embodiments, if not otherwise specified, heterocyclic groups have 1-2 heteroatoms selected from N, O and S as ring members, and 4-7 ring atoms, and are optionally substituted with up to four groups selected from halo, oxo, CN, amino, hydroxy, C$_{1-3}$ alkyl, —OR*, —NR*$_2$, —SR*, —SO$_2$R*, —COOR*, and —CONR*$_2$, where each R* is independently H or C$_{1-3}$ alkyl. In particular, heterocyclic groups containing a sulfur atom are optionally substituted with one or two oxo groups on the sulfur.

"Heteroaryl" is a completely unsaturated (aromatic) ring. The term "heteroaryl" refers to a 5-14 membered monocyclic- or bicyclic- or tricyclic-aromatic ring system, having 1 to 8 heteroatoms selected from N, O or S. Typically, the heteroaryl is a 5-10 membered ring or ring system (e.g., 5-7 membered monocyclic group or an 8-10 membered bicyclic group), often a 5-6 membered ring containing up to four heteroatoms selected from N, O and S, though often a heteroaryl ring contains no more than one divalent O or S in the ring. Typical heteroaryl groups include furan, isothiazole, thiadiazole, oxadiazole, indazole, indole, quinoline, 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-(1,2,4-triazolyl), 4- or 5-(1,2, 3-triazolyl), tetrazolyl, triazine, pyrimidine, 2-, 3-, or 4-pyridyl, 3- or 4-pyridazinyl, 3-, 4-, or 5-pyrazinyl, 2-pyrazinyl, and 2-, 4-, or 5-pyrimidinyl. Heteroaryl groups are and are optionally substituted with up to four groups selected from halo, CN, amino, hydroxy, C$_{1-3}$ alkyl, —OR*, —NR*$_2$, —SR*, —SO$_2$R*, —COOR*, and —CONR*$_2$, where each R* is independently H or C$_{1-3}$ alkyl.

The term "hydroxy" or "hydroxyl" refers to the group —OH.

Various embodiments of the invention are described herein. It will be recognized that features specified in each embodiment may be combined with other specified features to provide further embodiments. The following enumerated embodiments are representative of the invention:

1. A compound of formula (I):

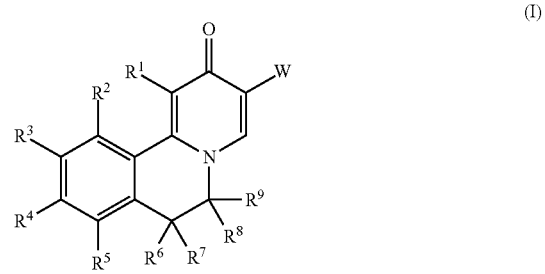

wherein:

R$^1$ is H, halo, or C$_1$-C$_3$ alkyl;

R$^2$ is H, halo, CN, C$_1$-C$_3$ alkyl or C$_1$-C$_3$ haloalkyl, C$_1$-C$_3$ alkoxy;

R$^3$ is OH, halo, CN, C$_1$-C$_3$ alkyl, C$_3$-C$_6$ cycloalkyl, C$_1$-C$_3$ haloalkyl, C$_1$-C$_3$ alkoxy, or C$_1$-C$_3$ haloalkoxy;

R$^4$ is selected from R$^{11}$, —OR$^{11}$, —SR$^{11}$, and —NRR$^{11}$;

R$^{11}$ is C$_1$-C$_4$ alkyl, C$_3$-C$_6$ cycloalkyl, oxetanyl, tetrahydrofuranyl, or tetrahydropyranyl, each of which is optionally substituted with up to three groups selected from halo, CN, —OR, C$_1$-C$_3$ haloalkoxy, —NR$_2$, and a 4-7 membered heterocyclic group containing one or two heteroatoms selected from N, O and S as ring members that is optionally substituted with one or two groups selected from halo, oxo, CN, R, —OR, and —NR$_2$;

R is independently selected at each occurrence from H and C$_1$-C$_3$ alkyl optionally substituted with one to three groups selected from halo, —OH, C$_1$-C$_3$ alkoxy, oxo, CN, —NH$_2$, —NH(C$_1$-C$_3$ alkyl), —N(C$_1$-C$_3$ alkyl)$_2$, and cyclopropyl;

and two R groups directly attached to the same atom, which may be C or N, can optionally be taken together to form a 3-6 membered ring that can optionally contain an added heteroatom selected from N, O and S as a ring member, and can be substituted by up to two groups selected from —OH, oxo, $C_1$-$C_3$ alkyl, and $C_1$-$C_3$ alkoxy;

$R^5$ is H, halo, CN, $C_1$-$C_3$ alkyl, or $C_1$-$C_3$ haloalkyl;

$R^6$ is H, halo, $C_1$-$C_3$ alkoxy, or $C_1$-$C_6$ alkyl;

$R^7$ is H, halo, $C_1$-$C_3$ alkoxy, or $C_1$-$C_6$ alkyl;

$R^8$ is H or $C_1$-$C_6$ alkyl;

$R^9$ taken together with one group selected from $R^6$, $R^7$ and $R^8$ forms a 3-7 membered cycloalkyl ring or a 3-7 membered heterocyclic ring containing N, O or S as a ring member; wherein the cycloalkyl or heterocyclic ring is optionally substituted with up to three groups selected from R, —OR, —$NR_2$, halo, CN, COOR, $CONR_2$, and oxo;

W is —$COOR^{10}$, —C(O)NH—$SO_2R$, —C(O)NH—$SO_2NR_2$, 5-tetrazolyl, or 1,2,4-oxadiazol-3-yl-5(4H)-one;

$R^{10}$ is H or $C_1$-$C_6$ alkyl that is optionally substituted with one or two groups selected from halo, —OR, oxo, CN, —$NR_2$, COOR, and $CONR_2$;

or a pharmaceutically acceptable salt thereof.

A preferred option for W in embodiment 1 is —COOH.

2. A compound according to embodiment 1 or a pharmaceutically acceptable salt thereof, wherein $R^1$ is H. Alternatively, a compound of embodiment 1 wherein $R^1$ is F or Cl.

3. A compound according to embodiment 1 or embodiment 2 or a pharmaceutically acceptable salt thereof, wherein $R^2$ is H or halo.

4. A compound according to any one of embodiments 1 to 3 or a pharmaceutically acceptable salt thereof, wherein $R^3$ is $C_1$-$C_3$ alkoxy or halo.

5. A compound according to any of the preceding embodiments or a pharmaceutically acceptable salt thereof, wherein $R^4$ is —$OR^1$.

6. A compound according to any of the preceding embodiments or a pharmaceutically acceptable salt thereof, wherein $R^5$ is H or halo.

7. A compound according to any of the preceding embodiments or a pharmaceutically acceptable salt thereof, which is of the formula:

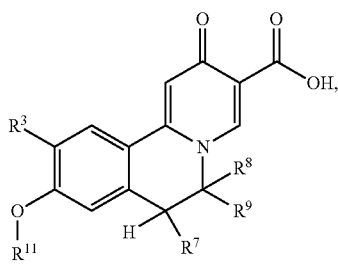

wherein $R^9$ taken together with $R^7$ forms a 3-7 membered cycloalkyl ring or a 3-7 membered heterocyclic ring containing N, O or S as a ring member; wherein the cycloalkyl or heterocyclic ring is optionally substituted with up to three groups selected from R, —OR, —$NR_2$, halo, CN, COOR, $CONR_2$, and oxo; or a pharmaceutically acceptable salt thereof.

In preferred compounds of this embodiment, the ring formed by $R^9$ and $R^7$ taken together is cis-fused onto the tricyclic core. In certain compounds of this embodiment, $R^8$ is H. Compounds of special interest in this embodiment include compounds with this absolute stereochemistry:

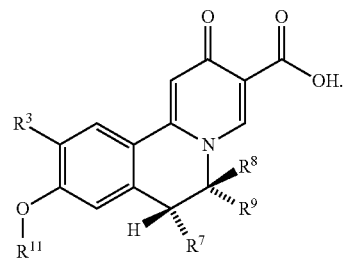

8. A compound according to any of embodiments 1-6, which is of the formula:

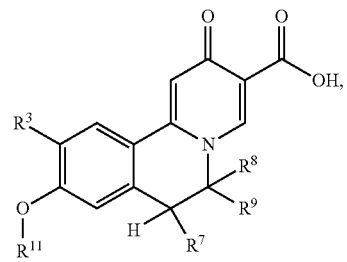

wherein $R^9$ taken together with $R^8$ forms a 3-7 membered cycloalkyl ring or a 3-7 membered heterocyclic ring containing N, O or S as a ring member; wherein the cycloalkyl or heterocyclic ring is optionally substituted with up to three groups selected from R, —OR, —$NR_2$, halo, CN, COOR, $CONR_2$, and oxo; or a pharmaceutically acceptable salt thereof.

9. A compound according to any of the preceding embodiments or a pharmaceutically acceptable salt thereof, wherein $R^{11}$ is $C_1$-$C_4$ alkyl, optionally substituted with up to two groups selected from halo, CN, —OR, $C_1$-$C_3$ haloalkoxy, and a 4-7 membered heterocyclic group containing one or two heteroatoms selected from N, O and S as ring members that is optionally substituted with one or two groups selected from halo, oxo, CN, R, —OR, and —$NR_2$.

10. A compound according to any of embodiments 1-9 or a pharmaceutically acceptable salt thereof, wherein the $R^{11}$ is selected from —$CH_2CH_2OMe$, —$CH_2CH_2CH_2OMe$, —$CH_2$—OEt, —$CH_2CH_2$-Q, and —$CH_2CH_2CH_2$-Q, where Q is selected from

11. A compound according to any of the preceding embodiments or a pharmaceutically acceptable salt thereof, wherein $R^9$ taken together with one group selected from $R^6$, $R^7$ and $R^8$ forms a 4-6 membered cycloalkyl ring or a 5-6 membered heterocyclic ring containing N, O or S as a ring member; wherein the cycloalkyl or heterocyclic ring is optionally substituted with up to three groups selected from R, —OR, —$NR_2$, halo, CN, COOR, $CONR_2$, and oxo.

12. The compound according to embodiment 1, which is selected from:

-continued
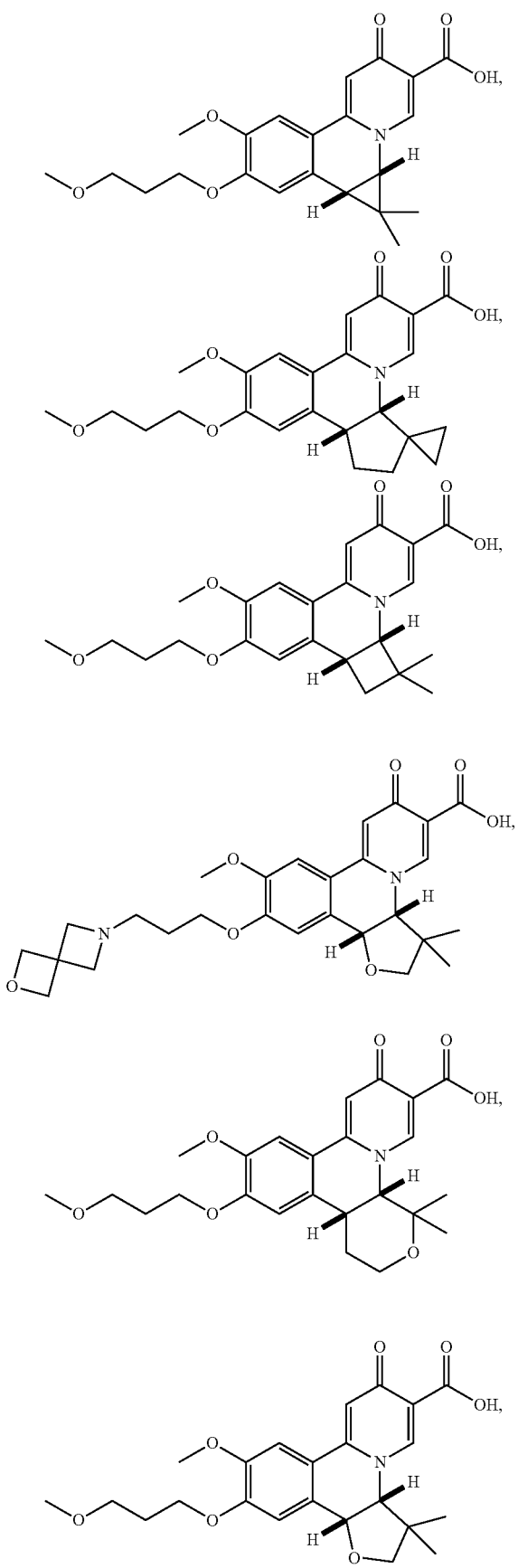
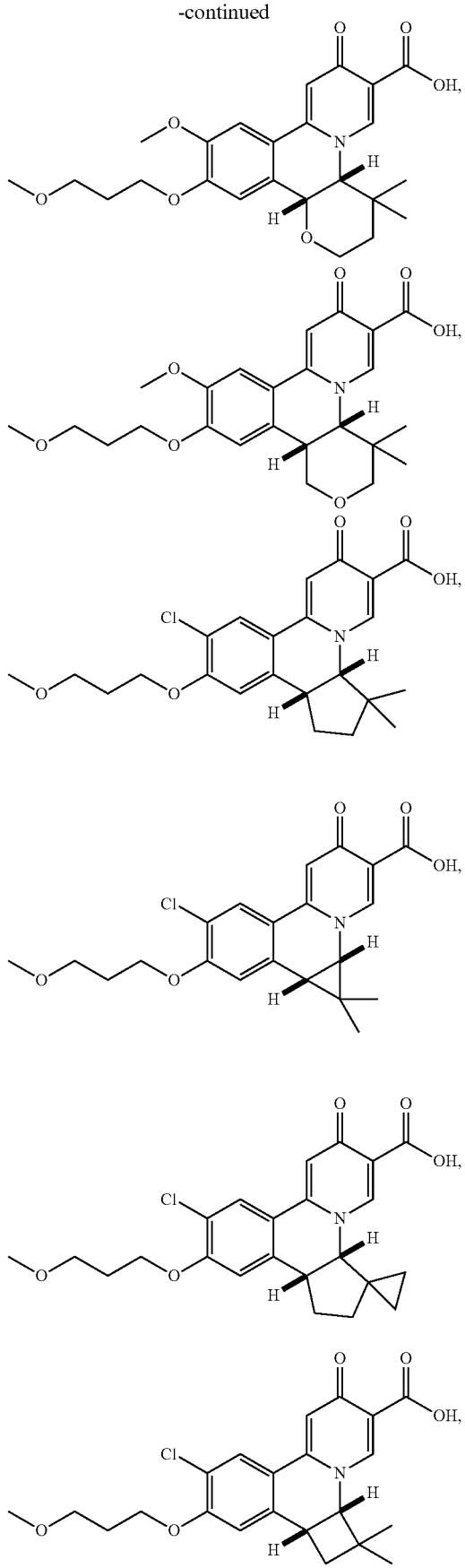

-continued
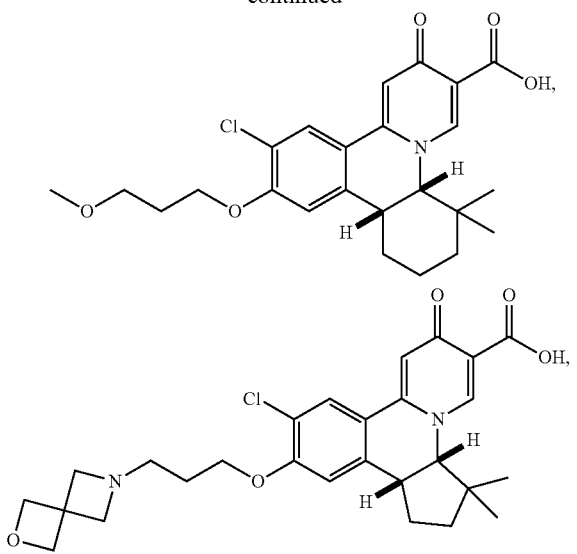
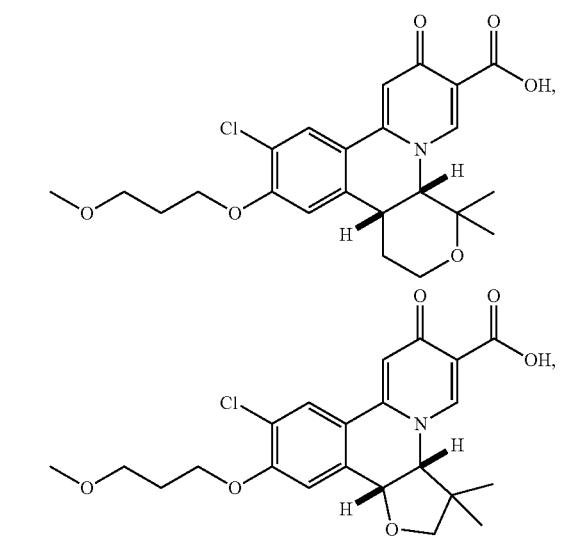
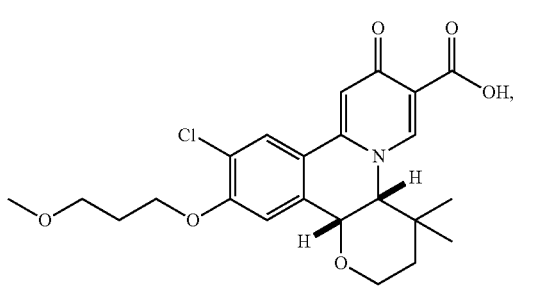
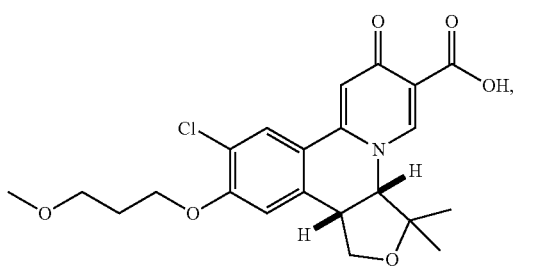
-continued
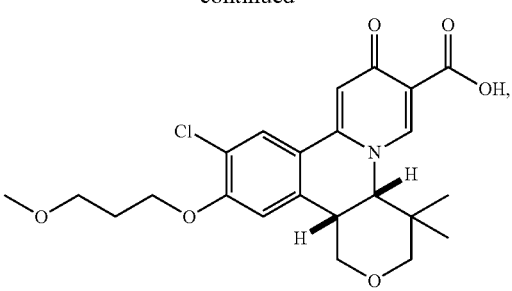
and the enantiomers of these compounds;
or a pharmaceutically acceptable salt thereof. Additional compounds of embodiment 1 include the following, and their pharmaceutically acceptable salts:
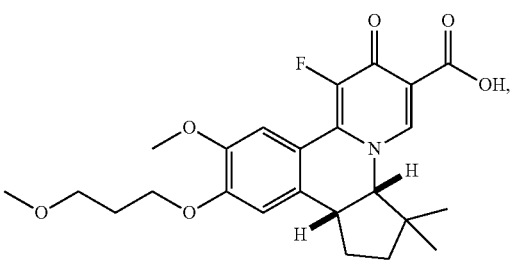
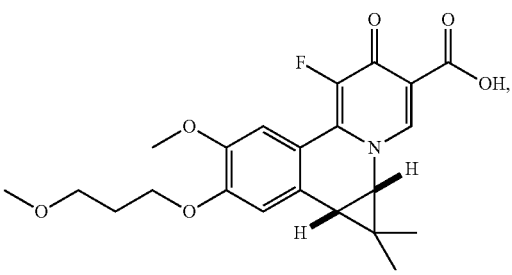
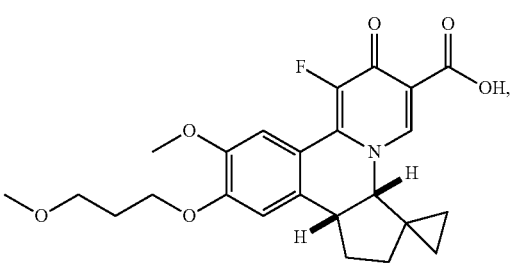
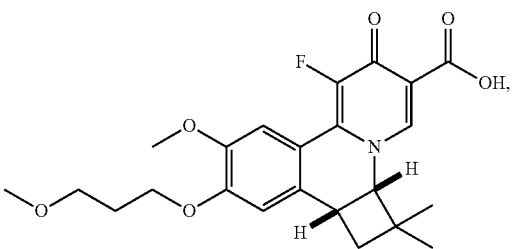

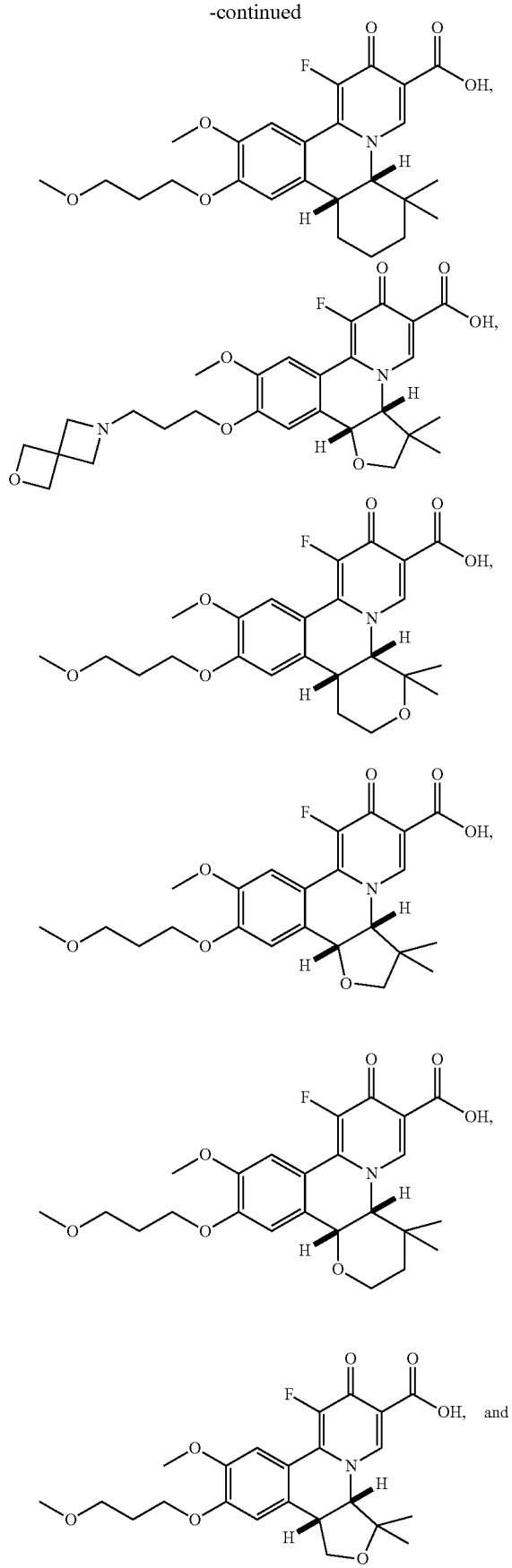
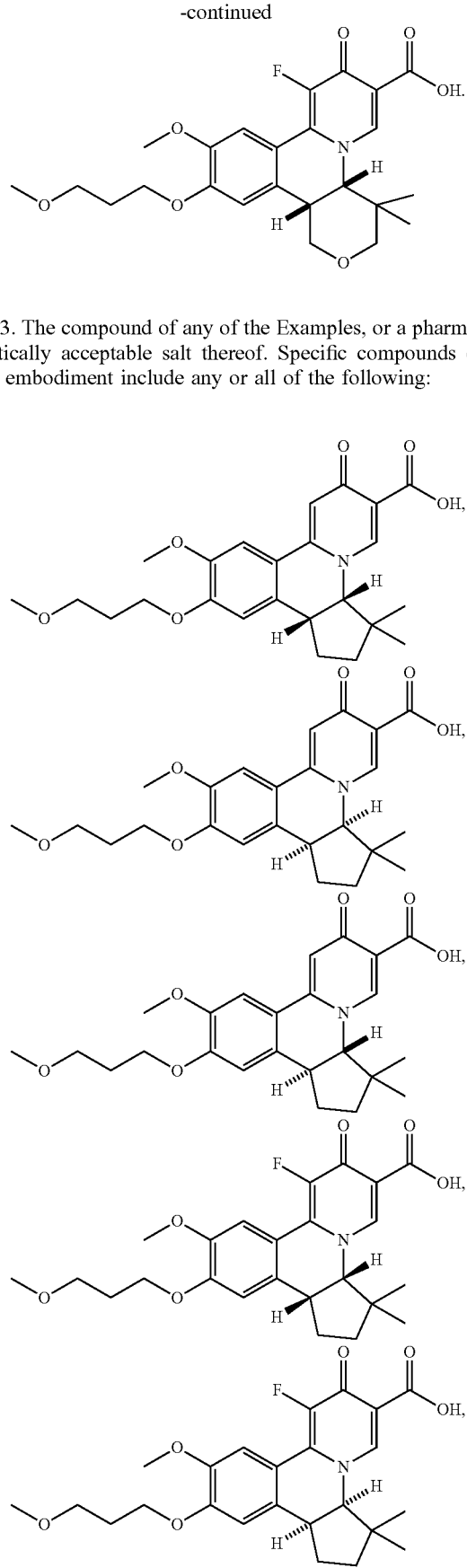
13. The compound of any of the Examples, or a pharmaceutically acceptable salt thereof. Specific compounds of this embodiment include any or all of the following:

-continued

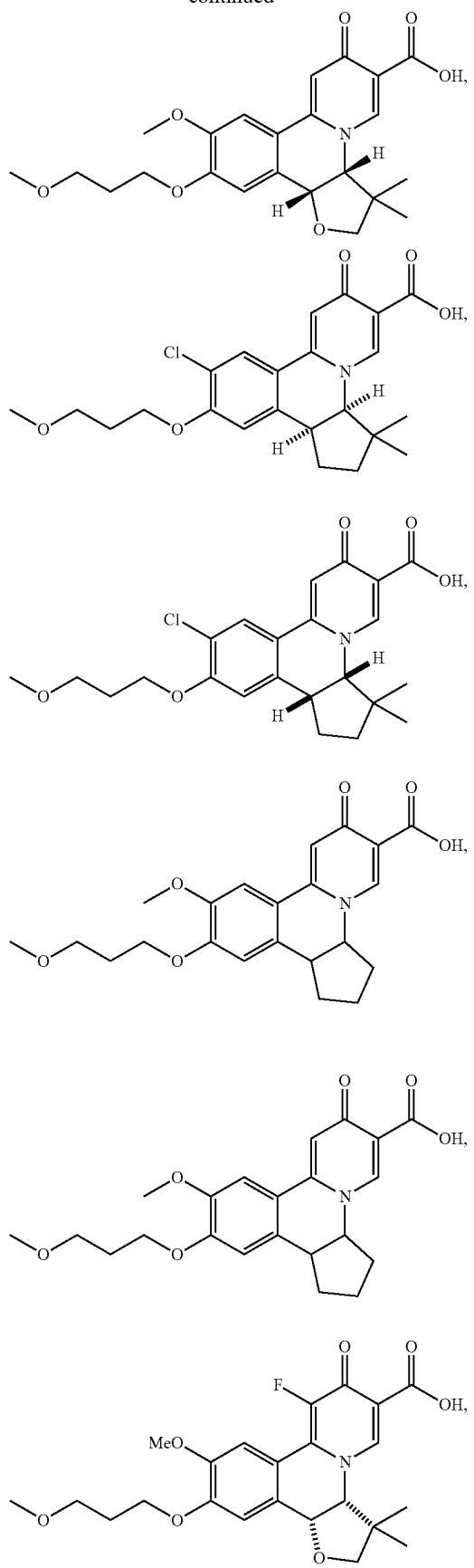

-continued

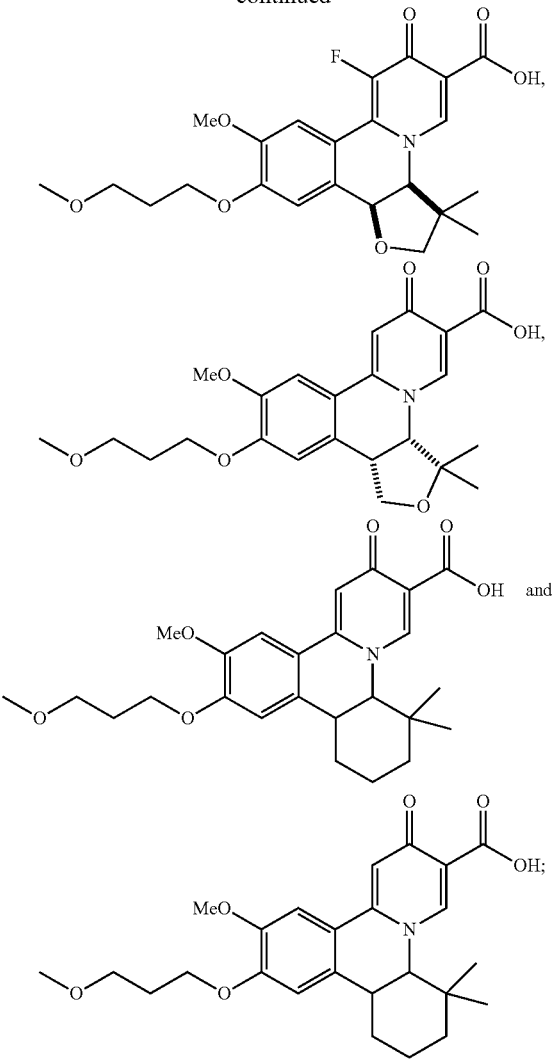

and the pharmaceutically acceptable salts of these.

14. A pharmaceutical composition, comprising a compound of any of the preceding embodiments admixed with at least one pharmaceutically acceptable carrier.

15. A method to treat a hepatitis B infection, which comprises administering to a patient having a hepatitis B infection a compound of any of embodiments 1-13 or a pharmaceutical composition of embodiment 14.

16. The method of embodiment 15, wherein the compound of any one of claims 1-13 or the pharmaceutical composition of claim 14 is used in combination with an additional therapeutic agent selected from an interferon or peginterferon, an HBV polymerase inhibitor, a viral entry inhibitor, a viral maturation inhibitor, a capsid assembly inhibitor, an HBV core modulator, a reverse transcriptase inhibitor, a TLR-agonist, or an immunomodulator.

17. A method to inhibit replication of hepatitis B virus, which comprises contacting the hepatitis B virus, either in vitro or in vivo, with a compound according to any one of embodiments 1-13.

18. A compound according to any one of embodiments 1-11, wherein $R^1$ is F.

Another embodiment of the invention provides a compound as described above, or a pharmaceutically acceptable salt thereof, as a medicament.

Also within the scope of this invention is the use of a compound of formula (I), or a pharmaceutically acceptable salt thereof, for the manufacture of a medicament for the treatment or prevention of a viral disease and/or infection in a human being, including HBV.

Included within the scope of this invention are pharmaceutical compositions comprising a compound of Formula (I), or a pharmaceutically acceptable salt thereof, and a pharmaceutically acceptable carrier, and optionally further including an additional pharmaceutically acceptable carrier or excipient.

According to a further aspect of this embodiment the pharmaceutical composition according to this invention further comprises a therapeutically effective amount of at least one other antiviral agent.

The invention also provides the use of a pharmaceutical composition as described hereinabove for the treatment of a HBV infection in a human being having or at risk of having the infection.

The invention also provides the use of a pharmaceutical composition as described hereinabove for the treatment of HBV infection in a human being having or at risk of having the disease.

Another aspect of the invention involves a method of treating or preventing a hepatitis B viral disease and/or infection in a human being by administering to the human being an antivirally effective amount of a compound of the invention, a pharmaceutically acceptable salt thereof, or a composition as described above, alone or in combination with at least one other antiviral agent, administered together or separately.

An additional aspect of this invention refers to an article of manufacture comprising a composition effective to treat a hepatitis B viral disease and/or infection; and packaging material comprising a label which indicates that the composition can be used to treat disease and/or infection by a hepatitis B virus; wherein the composition comprises a compound of formula (I) according to this invention or a pharmaceutically acceptable salt thereof.

Still another aspect of this invention relates to a method of inhibiting the replication of HBV, comprising exposing the virus to an effective amount of the compound of formula (I), or a salt thereof, under conditions where replication of the virus is inhibited. This method can be practiced in vitro or in vivo.

Further included in the scope of the invention is the use of a compound of formula (I), or a salt thereof, to inhibit the replication of HBV.

In some embodiments, the compound of Formula (I) is co-administered with or used in combination with at least one additional therapeutic agent selected from: an interferon or peginterferon, an HBV polymerase inhibitor, a viral entry inhibitor, a viral maturation inhibitor, a capsid assembly inhibitor, an HBV core modulator, a reverse transcriptase inhibitor, a TLR-agonist, or an immunomodulator. Some particular therapeutic agents that may be used in combination with the compounds of the invention include immunomodulators described herein, interferon alfa 2a, interferon alfa-2b, pegylated interferon alfa-2a, pegylated interferon alfa-2b, TLR-7 and TLR-9 agonists, entecavir, tenofovir, cidofovir, telbivudine, didanosine, zalcitabine, stavudine, lamivudine, abacavir, emtricitabine, apricitabine, atevirapine, ribavirin, acyclovir, famciclovir, valacyclovir, ganciclovir, adefovir, efavirenz, nevirapine, delavirdine, and etravirine. Suitable core modulators are disclosed in WO2013/096744; suitable HBV capsid inhibitors are described in US2015/0252057.

These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of a compound of the invention, or a pharmaceutically acceptable salt thereof. Alternatively, these additional therapeutic agents may be administered separately from and optionally by different routes of administration and on different dosing schedules from the compound of the invention, provided the compound of the invention and the additional therapeutic agent are used concurrently for treatment of an HBV infection or a disorder caused or complicated by an HBV infection.

The dose range of the compounds of the invention applicable per day is usually from 0.01 to 100 mg/kg of body weight, preferably from 0.1 to 50 mg/kg of body weight. In some embodiments, the total daily dosage is between 1 and 25 mg, and may be administered in a single dose or in divided doses at different times to maintain a suitable plasma concentration. Each dosage unit may conveniently contain from 5% to 95% active compound (w/w). Preferably such preparations contain from 20% to 80% active compound, which is typically admixed with one or more pharmaceutically acceptable carriers or excipients.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

When the composition of this invention comprises a combination of a compound of the invention and one or more additional therapeutic or prophylactic agent, both the compound and the additional agent may be used at lower dosages than would be used typically for the individual compound when used as a single-agent treatment. Thus in some embodiments, each component may be present at dosage levels of between about 10 to 100%, and more preferably between about 10 and 80% of the dosage normally administered in a monotherapy regimen.

It is anticipated that the compounds of the invention may be used in combination with other therapeutic agents, just as combinations of therapeutic agents are currently used for the treatment of hepatitis C virus (HCV) infections. Thus a compound of the invention may be used in combination with a different anti-HBV therapeutic agent such as a nucleoside or an immunomodulatory agent. These combination therapies provide complementary mechanisms to suppress HBV and thus their use in combination should enhance efficacy and also reduce the frequency of resistance development.

Antiviral agents contemplated for use in such combination therapy include agents (compounds or biologicals) that are effective to inhibit the formation and/or replication of a virus in a human being, including but not limited to agents that interfere with either host or viral mechanisms necessary for the formation and/or replication of a virus in a human being.

Such agents can be selected from entecavir, tenofovir, cidofovir, telbivudine, didanosine, zalcitabine, stavudine, lamivudine, abacavir, emtricitabine, apricitabine, atevirapine, ribavirin, acyclovir, famciclovir, valacyclovir, ganciclovir, adefovir, efavirenz, nevirapine, delavirdine, and etravirine, and immunomodulators described herein including interferons and pegylated interferons, TLR-7 agonists, and TLR-9 agonists. Current HBV treatments including immunomodulatory agents, such as interferon-α and pegylated interferon-α, and oral nucleoside/nucleotide analogues (NAs), including lamivudine, adefovir, telbivudine, entecavir and tenofovir, are known to suppress but not eliminate HBV. *J. Antimicrob. Chemother.* 2011, vol. 66(12), 2715-25, and thus those therapeutics may be used in combination with a compound of the invention.

Many compounds of the invention contain one or more chiral centers. These compounds may be made and used as single isomers or as mixtures of isomers. Methods for separating the isomers, including diastereomers and enantiomers, are known in the art, and examples of suitable methods are described herein. In certain embodiments, the compounds of the invention are used as a single substantially pure isomer, meaning at least 90% of a sample of the compound is the specified isomer and less than 10% of the sample is any other isomer or mixture of isomers. Preferably, at least 95% of the sample is a single isomer. Selection of a suitable isomer is within the ordinary level of skill, as one isomer will typically be more active in the in vivo or in vitro assay described herein for measuring HBV activity, and will be the preferred isomer. Where in vitro activity differences between isomers are relatively small, e.g. less than about a factor of 4, a preferred isomer may be selected based on activity level against viral replication in cell culture, using methods such as those described herein: the isomer having a lower MIC (minimum inhibitory concentration) or EC-50 is preferred.

The compounds of the invention may be synthesized by the general synthetic routes illustrated below, specific examples of which are described in more detail in the Examples.

The term "an optical isomer" or "a stereoisomer" refers to any of the various stereoisomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible stereoisomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any resulting mixtures of isomers can be separated on the basis of the physicochemical differences of the constituents, into the pure or substantially pure geometric or optical isomers or diastereomers, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

As used herein, the terms "salt" or "salts" refers to an acid addition or base addition salt of a compound of the present invention. "Salts" include in particular "pharmaceutically acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is intended to represent unlabeled forms as well as isotopically labeled forms of the compounds of the present invention having up to three atoms with non-natural isotope distributions, e.g., sites that are enriched in deuterium or $^{13}C$ or $^{15}N$. Isotopically labeled compounds have structures depicted by the formulas given herein except that one or more atoms are replaced by an atom having a selected atomic mass or mass number other than the natural-abundance mass distribution. Examples of isotopes that can be usefully over-incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds of the present invention, for example those into which radioactive isotopes, such as $^{3}H$ and $^{14}C$, or those in which non-radioactive isotopes, such as $^{2}H$ and $^{13}C$ are present at levels substantially above normal isotope distribution. Such isotopically labelled compounds are useful in metabolic studies (with $^{14}C$, for example), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound of the present invention may be particularly desirable for PET or SPECT studies. Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent typically employed. Labeled samples may be useful with quite low isotope incorporation, such as where a radiolabel is used to detect trace amounts of the compound.

Further, more extensive substitution with heavier isotopes, particularly deuterium (i.e., $^{2}H$ or D), may afford certain therapeutic advantages resulting from greater metabolic stability, for example increased in vivo half-life or reduced dosage requirements or an improvement in therapeutic index. It is understood that deuterium in this context is regarded as a substituent of a compound of the present invention, and typically a sample of a compound having deuterium as a substituent has at least 50% deuterium incorporation at the labeled position(s). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d^6$-acetone, $d^6$-DMSO.

Compounds of the present invention that contain groups capable of acting as donors and/or acceptors for hydrogen bonds may be capable of forming co-crystals with suitable co-crystal formers. These co-crystals may be prepared from compounds of the present invention by known co-crystal forming procedures. Such procedures include grinding, heating, co-subliming, co-melting, or contacting in solution compounds of the present invention with the co-crystal former under crystallization conditions and isolating co-crystals thereby formed. Suitable co-crystal formers include those described in WO 2004/078163. Hence the invention further provides co-crystals comprising a compound of the present invention.

Methods of Use

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The compounds of the invention can be administered by known methods, including oral, parenteral, inhalation, and the like. In certain embodiments, the compound of the invention is administered orally, as a pill, lozenge, troche, capsule, solution, or suspension. In other embodiments, a compound of the invention is administered by injection or infusion. Infusion is typically performed intravenously, often over a period of time between about 15 minutes and 4 hours. In other embodiments, a compound of the invention is administered intranasally or by inhalation; inhalation methods are particularly useful for treatment of respiratory infections. Compounds of the present invention exhibit oral bioavailability, so oral administration is sometimes preferred.

In certain embodiments of the present invention, a compound of the present invention is used in combination with a second antiviral agent, such as those named herein.

By the term "combination", is meant either a fixed combination in one dosage unit form, as separate dosage forms suitable for use together either simultaneously or sequentially, or as a kit of parts for the combined administration where a compound of the present invention and a combination partner may be administered independently at the same time or separately within time intervals that especially allow that the combination partners show a cooperative, e.g., synergistic, effect, or any combination thereof.

The second antiviral agent may be administered in combination with the compounds of the present inventions wherein the second antiviral agent is administered prior to, simultaneously, or after the compound or compounds of the present invention. When simultaneous administration of a compound of the invention with a second agent is desired and the route of administration is the same, then a compound of the invention may be formulated with a second agent into the same dosage form. An example of a dosage form containing a compound of the invention and a second agent is a tablet or a capsule.

In some embodiments, a combination of a compound of the invention and a second antiviral agent may provide synergistic activity. The compound of the invention and second antiviral agent may be administered together, separate but simultaneously, or sequentially.

An "effective amount" of a compound is that amount necessary or sufficient to treat or prevent a viral infection and/or a disease or condition described herein. In an example, an effective amount of a compound of Formula I is an amount sufficient to treat viral infection in a subject. In another example, an effective amount is an amount sufficient to treat HBV in a subject in need of such treatment. The effective amount can vary depending on such factors as the size and weight of the subject, the type of illness, or the particular compound of the invention. For example, the choice of the compound of the invention can affect what constitutes an "effective amount." One of ordinary skill in the art would be able to study the factors contained herein and make the determination regarding the effective amount of the compounds of the invention without undue experimentation.

The regimen of administration can affect what constitutes an effective amount. The compound of the invention can be administered to the subject either prior to or after the onset of a viral infection. Further, several divided dosages, as well as staggered dosages, can be administered daily or sequentially, or the dose can be continuously infused, or can be a bolus injection. Further, the dosages of the compound(s) of the invention can be proportionally increased or decreased as indicated by the exigencies of the therapeutic or prophylactic situation.

Compounds of the invention may be used in the treatment of states, disorders or diseases as described herein, or for the manufacture of pharmaceutical compositions for use in the treatment of these diseases. The invention provides methods of use of compounds of the present invention in the treatment of these diseases or for preparation of pharmaceutical compositions having compounds of the present invention for the treatment of these diseases.

The language "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of at least one compound of Formula (I) or any subgenus thereof as active ingredient in combination with a pharmaceutically acceptable carrier, or optionally two or more pharmaceutically acceptable carriers.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Typically, pharmaceutically acceptable carriers are sterilized and/or substantially pyrogen-free.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, inhalation, topical, transdermal, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored base, for example, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration may comprise one or more compounds of the invention in combination with one or more pharmaceutically acceptable carriers such as sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, glycol ethers, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc., administration by injection, infusion or inhalation; topical by lotion or ointment; and rectal by suppositories.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Intravenous infusion is sometimes a preferred method of delivery for compounds of the invention. Infusion may be used to deliver a single daily dose or multiple doses. In some embodiments, a compound of the invention is administered by infusion over an interval between 15 minutes and 4 hours, typically between 0.5 and 3 hours. Such infusion may be used once per day, twice per day or up to three times per day.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous and subcutaneous doses of the compounds of this invention for a patient, when used for the indicated effects, will range from about 0.0001 to about 100 mg per kilogram of body weight per day, more preferably from about 0.01 to about 50 mg per kg per day, and still more preferably from about 0.1 to about 20 mg per kg per day. An effective amount is that amount which prevents or treats a viral infection, such as HBV.

If desired, the effective daily dose of the active compound may be administered as a single dose per day, or as two, three, four, five, six or more sub-doses administered separately at appropriate intervals throughout the day, optionally, in unit dosage forms. Compounds delivered orally or by inhalation, are commonly administered in one to four doses per day. Compounds delivered by injection are typically administered once per day, or once every other day. Compounds delivered by infusion are typically administered in one to three doses per day. When multiple doses are administered within a day, the doses may be administered at intervals of about 4 hours, about 6 hours, about 8 hours or about 12 hours.

While it is possible for a compound of the present invention to be administered alone, it is preferable to administer the compound as a pharmaceutical composition such as those described herein. Thus methods of using the compounds of the invention include administering the compound as a pharmaceutical composition, wherein at least one compound of the invention is admixed with a pharmaceutically acceptable carrier prior to administration.

Use of Compounds of the Invention in Combination with Immunomodulators

The compounds and compositions described herein can be used or administered in combination with one or more therapeutic agents that act as immunomodulators, e.g., an activator of a costimulatory molecule, or an inhibitor of an immune-inhibitory molecule, or a vaccine. The Programmed Death 1 (PD-1) protein is an inhibitory member of the extended CD28/CTLA4 family of T cell regulators (Okazaki et al. (2002) Curr Opin Immunol 14: 391779-82; Bennett et al. (2003) J. Immunol. 170:711-8). PD-1 is expressed on activated B cells, T cells, and monocytes. PD-1 is an immune-inhibitory protein that negatively regulates TCR signals (Ishida, Y. et al. (1992) EMBO J. 11:3887-3895; Blank, C. et al. (Epub 2006 Dec. 29) Immunol. Immunother. 56(5):739-745), and is up-regulated in chronic infections. The interaction between PD-1 and PD-L1 can act as an immune checkpoint, which can lead to, e.g., a decrease in infiltrating lymphocytes, a decrease in T-cell receptor mediated proliferation, and/or immune evasion by cancerous or infected cells (Dong et al. (2003) J. Mol. Med. 81:281-7; Blank et al. (2005) Cancer Immunol. Immunother. 54:307-314; Konishi et al. (2004) Clin. Cancer Res. 10:5094-100). Immune suppression can be reversed by inhibiting the local interaction of PD-1 with PD-L1 or PD-L2; the effect is additive when the interaction of PD-1 with PD-L2 is blocked as well (Iwai et al. (2002) Proc. Nat'l. Acad. Sci. USA 99:12293-7; Brown et al. (2003) J. Immunol. 170:1257-66). Immunomodulation can be achieved by binding to either the immune-inhibitory protein (e.g., PD-1) or to binding proteins that modulate the inhibitory protein (e.g., PD-L1, PD-L2).

In one embodiment, the combination therapies of the invention include an immunomodulator that is an inhibitor or antagonist of an inhibitory molecule of an immune checkpoint molecule. In another embodiment the immunomodulator binds to a protein that naturally inhibits the immuno-inhibitory checkpoint molecule. When used in combination with antiviral compounds, these immunomodulators can enhance the antiviral response, and thus enhance efficacy relative to treatment with the antiviral compound alone.

The term "immune checkpoints" refers to a group of molecules on the cell surface of CD4 and CD8 T cells. These molecules can effectively serve as "brakes" to down-modulate or inhibit an adaptive immune response. Immune checkpoint molecules include, but are not limited to, Programmed Death 1 (PD-1), Cytotoxic T-Lymphocyte Antigen 4 (CTLA-4), B7H1, B7H4, OX-40, CD137, CD40, and LAG3, which directly inhibit immune cells. Immunotherapeutic agents which can act as immune checkpoint inhibitors useful in the methods of the present invention, include, but are not limited to, inhibitors of PD-L1, PD-L2, CTLA4, TIM3, LAG3, VISTA, BTLA, TIGIT, LAIR1, CD160, 2B4 and/or TGFR beta. Inhibition of an inhibitory molecule can be performed by inhibition at the DNA, RNA or protein level. In some embodiments, an inhibitory nucleic acid (e.g., a dsRNA, siRNA or shRNA), can be used to inhibit expression of an inhibitory molecule. In other embodiments, the inhibitor of an inhibitory signal is a polypeptide, e.g., a soluble ligand, or an antibody or antigen-binding fragment thereof, that binds to the inhibitory molecule.

By "in combination with," it is not intended to imply that the therapy or the therapeutic agents must be administered at the same time and/or formulated for delivery together, although these methods of delivery are within the scope described herein. The immunomodulator can be administered concurrently with, prior to, or subsequent to, one or more compounds of the invention, and optionally one or more additional therapies or therapeutic agents. The therapeutic agents in the combination can be administered in any order. In general, each agent will be administered at a dose and/or on a time schedule determined for that agent. It will further be appreciated that the therapeutic agents utilized in this combination may be administered together in a single composition or administered separately in different compositions. In general, it is expected that each of the therapeutic agents utilized in combination be utilized at levels that do not exceed the levels at which they are utilized individually. In some embodiments, the levels utilized in combination will be lower than those utilized individually.

In certain embodiments, the antiviral compounds described herein are administered in combination with one or more immunomodulators that are inhibitors of PD-1, PD-L1 and/or PD-L2. Each such inhibitor may be an antibody, an antigen binding fragment thereof, an immunoadhesin, a fusion protein, or an oligopeptide. Examples of such immunomodulators are known in the art.

In some embodiments, the immunomodulator is an anti-PD-1 antibody chosen from MDX-1106, Merck 3475 or CT-011.

In some embodiments, the immunomodulator is an immunoadhesin (e.g., an immunoadhesin comprising an extracellular or PD-1 binding portion of PD-LI or PD-L2 fused to a constant region (e.g., an Fc region of an immunoglobulin sequence).

In some embodiments, the immunomodulator is a PD-1 inhibitor such as AMP-224.

In some embodiments, the the immunomodulator is a PD-LI inhibitor such as anti-PD-LI antibody.

In some embodiments, the immunomodulator is an anti-PD-LI binding antagonist chosen from YW243.55.S70, MPDL3280A, MEDI-4736, MSB-0010718C, or MDX-1105. MDX-1105, also known as BMS-936559, is an anti-PD-LI antibody described in WO2007/005874. Antibody YW243.55.S70 is an anti-PD-LI described in WO 2010/077634.

In some embodiments, the immunomodulator is nivolumab (CAS Registry Number: 946414-94-4). Alternative names for nivolumab include MDX-1106, MDX-1106-04, ONO-4538, or BMS-936558. Nivolumab is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449, EP2161336 and WO2006/121168.

In some embodiments, the immunomodulator is an anti-PD-1 antibody Pembrolizumab. Pembrolizumab (also referred to as Lambrolizumab, MK-3475, MK03475, SCH-900475 or KEYTRUDA®; Merck) is a humanized IgG4 monoclonal antibody that binds to PD-1. Pembrolizumab and other humanized anti-PD-1 antibodies are disclosed in Hamid, O. et al. (2013) New England Journal of Medicine 369 (2): 134-44, U.S. Pat. No. 8,354,509, WO2009/114335, and WO2013/079174.

In some embodiments, the immunomodulator is Pidilizumab (CT-011; Cure Tech), a humanized IgG1k monoclonal antibody that binds to PD1. Pidilizumab and other humanized anti-PD-1 monoclonal antibodies are disclosed in WO2009/101611.

Other anti-PD1 antibodies useful as immunomodulators for use in the methods disclosed herein include AMP 514 (Amplimmune), and anti-PD1 antibodies disclosed in U.S. Pat. No. 8,609,089, US 2010028330, and/or US 20120114649. In some embodiments, the anti-PD-L1 antibody is MSB0010718C. MSB0010718C (also referred to as A09-246-2; Merck Serono) is a monoclonal antibody that binds to PD-L1.

In some embodiments, the immunomodulator is MDPL3280A (Genentech/Roche), a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906. Other anti-PD-L1 binding agents useful as immunomodulators for methods of the invention include YW243.55.S70 (see WO2010/077634), MDX-1105 (also referred to as BMS-936559), and anti-PD-L1 binding agents disclosed in WO2007/005874.

In some embodiments, the immunomodulator is AMP-224 (B7-DCIg; Amplimmune; e.g., disclosed in WO2010/027827 and WO2011/066342), is a PD-L2 Fc fusion soluble receptor that blocks the interaction between PD1 and B7-H1.

In some embodiments, the immunomodulator is an anti-LAG-3 antibody such as BMS-986016. BMS-986016 (also referred to as BMS986016) is a monoclonal antibody that binds to LAG-3. BMS-986016 and other humanized anti-LAG-3 antibodies are disclosed in US 2011/0150892, WO2010/019570, and WO2014/008218

In certain embodiments, the combination therapies disclosed herein include a modulator of a costimulatory molecule or an inhibitory molecule, e.g., a co-inhibitory ligand or receptor.

In one embodiment, the costimulatory modulator, e.g., agonist, of a costimulatory molecule is chosen from an agonist (e.g., an agonistic antibody or antigen-binding fragment thereof, or soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand.

In another embodiment, the combination therapies disclosed herein include an immunomodulator that is a costimulatory molecule, e.g., an agonist associated with a positive signal that includes a costimulatory domain of CD28, CD27, ICOS and/or GITR.

Exemplary GITR agonists include, e.g., GITR fusion proteins and anti-GITR antibodies (e.g., bivalent anti-GITR antibodies), such as, a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

In one embodiment, the immunomodulator used is a soluble ligand (e.g., a CTLA-4-Ig), or an antibody or antibody fragment that binds to PD-L1, PD-L2 or CTLA4. For example, the anti-PD-1 antibody molecule can be administered in combination with an anti-CTLA-4 antibody, e.g., ipilimumab, for example. Exemplary anti-CTLA4 antibodies include Tremelimumab (lgG2 monoclonal antibody available from Pfizer, formerly known as ticilimumab, CP-675,206); and Ipilimumab (CTLA-4 antibody, also known as MDX-010, CAS No. 477202-00-9).

In one embodiment, an anti-PD-1 antibody molecule is administered after treatment with a compound of the invention as described herein.

In another embodiment, an anti-PD-1 or PD-L1 antibody molecule is administered in combination with an anti-LAG-3 antibody or an antigen-binding fragment thereof. In another embodiment, the anti-PD-1 or PD-L1 antibody molecule is administered in combination with an anti-TIM-3 antibody or antigen-binding fragment thereof. In yet other embodiments, the anti-PD-1 or PD-L1 antibody molecule is administered in combination with an anti-LAG-3 antibody and an anti-TIM-3 antibody, or antigen-binding fragments thereof. The combination of antibodies recited herein can be administered separately, e.g., as separate antibodies, or linked, e.g., as a bispecific or trispecific antibody molecule. In one embodiment, a bispecific antibody that includes an anti-PD-1 or PD-L1 antibody molecule and an anti-TIM-3 or anti-LAG-3 antibody, or antigen-binding fragment thereof, is administered. In certain embodiments, the combination of antibodies recited herein is used to treat a cancer, e.g., a cancer as described herein (e.g., a solid tumor). The efficacy of the aforesaid combinations can be tested in animal models known in the art. For example, the animal models to test the synergistic effect of anti-PD-1 and anti-LAG-3 are described, e.g., in Woo et al. (2012) Cancer Res. 72(4):917-27).

Exemplary immunomodulators that can be used in the combination therapies include, but are not limited to, e.g., afutuzumab (available from Roche®); pegfilgrastim (Neulasta®); lenalidomide (CC-5013, Revlimid®); thalidomide (Thalomid®), actimid (CC4047); and cytokines, e.g., IL-21 or IRX-2 (mixture of human cytokines including interleukin 1, interleukin 2, and interferon γ, CAS 951209-71-5, available from IRX Therapeutics).

Exemplary doses of such immunomodulators that can be used in combination with the antiviral compounds of the invention include a dose of anti-PD-1 antibody molecule of about 1 to 10 mg/kg, e.g., 3 mg/kg, and a dose of an anti-CTLA-4 antibody, e.g., ipilimumab, of about 3 mg/kg.

Examples of embodiments of the methods of using the antiviral compounds of the invention in combination with an immunomodulator include these, which may be used along with a compound of Formula I or any subgenus or species thereof that is disclosed herein:

i. A method to treat a viral infection in a subject, comprising administering to the subject a compound of Formula (I) as described herein, and an immunomodulator.

ii. The method of embodiment i, wherein the immunomodulator is an activator of a costimulatory molecule or an inhibitor of an immune checkpoint molecule.

iii. The method of either of embodiments i and ii, wherein the activator of the costimulatory molecule is an agonist of one or more of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 and CD83 ligand.

iv. The method of any of embodiments i-iii above, wherein the inhibitor of the immune checkpoint molecule is chosen from PD-1, PD-L1, PD-L2, CTLA4, TIM3, LAG3, VISTA, BTLA, TIGIT, LAIR1, CD160, 2B4 and TGFR beta.

v. The method of any of any of embodiments i-iii, wherein the inhibitor of the immune checkpoint molecule is chosen from an inhibitor of PD-1, PD-L1, LAG-3, TIM-3 or CTLA4, or any combination thereof.

vi. The method of any of embodiments i-v, wherein the inhibitor of the immune checkpoint molecule is a soluble ligand or an antibody or antigen-binding fragment thereof, that binds to the immune checkpoint molecule.

vii. The method of any of embodiments i-vi, wherein the antibody or antigen-binding fragment thereof is from an IgG1 or IgG4 (e.g., human IgG1 or IgG4).

viii. The method of any of embodiments i-vii, wherein the antibody or antigen-binding fragment thereof is altered, e.g., mutated, to increase or decrease one or more of: Fc receptor binding, antibody glycosylation, the number of cysteine residues, effector cell function, or complement function.

ix. The method of any of embodiments i-viii, wherein the antibody molecule is a bispecific or multispecific antibody molecule that has a first binding specificity to PD-1 or PD-L1 and a second binding specifity to TIM-3, LAG-3, or PD-L2.

x. The method of any of embodiments i-ix, wherein the immunomodulator is an anti-PD-1 antibody chosen from Nivolumab, Pembrolizumab or Pidilizumab.

xi. The method of any of embodiments i-x, wherein the immunomodulator is an anti-PD-L1 antibody chosen from YW243.55.S70, MPDL3280A, MEDI-4736, MSB-0010718C, or MDX-1105.

xii. The method of any of embodiments i-x, wherein the immunomodulator is an anti-LAG-3 antibody molecule.

xiii. The method of embodiment xii, wherein the anti-LAG-3 antibody molecule is BMS-986016.

xiv. The method of any of embodiments i-x, wherein the immunomodulator is an anti-PD-1 antibody molecule administered by injection (e.g., subcutaneously or intravenously) at a dose of about 1 to 30 mg/kg, e.g., about 5 to 25 mg/kg, about 10 to 20 mg/kg, about 1 to 5 mg/kg, or about 3 mg/kg., e.g., once a week to once every 2, 3, or 4 weeks.

xv. The method of embodiment xiv, wherein the anti-PD-1 antibody molecule is administered at a dose from about 10 to 20 mg/kg every other week.

xvi. The method of embodiment xv, wherein the anti-PD-1 antibody molecule, e.g., nivolumab, is administered intravenously at a dose from about 1 mg/kg to 3 mg/kg, e.g., about 1 mg/kg, 2 mg/kg or 3 mg/kg, every two weeks.

xvii. The method of embodiment xv, wherein the anti-PD-1 antibody molecule, e.g., nivolumab, is administered intravenously at a dose of about 2 mg/kg at 3-week intervals.

The compounds of the invention share certain structural features with compounds reported to have the same utility as the compounds of the invention. For example, Example 132 in WO2015/113990 has this structure:

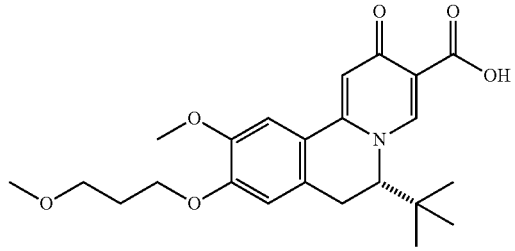 [SMILES: COCCCOc1cc2c(cc1OC)-c1cc(=O)c(C(=O)O)cn1[C@H](C(C)(C)C)C2]

and similar biological activity to the compounds of the invention. As illustrated herein, certain compounds of the invention have improved solubility and safety profiles when compared to the reference example in common screens that are used to predict suitability for development.

The compounds as described herein may be synthesized by the general synthetic routes below, specific examples of which are described in more detail in the Examples.

General Synthetic Procedures

All starting materials, building blocks, reagents, acids, bases, dehydrating agents, solvents, and catalysts utilized to synthesize the compounds of the invention are either commercially available or can be produced by organic synthesis methods known to one of ordinary skill in the art (Houben-Weyl 4th Ed. 1952, Methods of Organic Synthesis, Thieme, Volume 21). General methods for synthesis of compounds of the invention are illustrated by the Examples below, and by methods disclosed in published PCT applications WO2015/113990 and WO2015/173164.

List of Abbreviations

Ac acetyl
ACN Acetonitrile
AcOEt/EtOAc Ethyl acetate
AcOH acetic acid
aq aqueous
Bn benzyl
Bu butyl (nBu=n-butyl, tBu=tert-butyl)
CDI Carbonyldiimidazole
DBU 1,8-Diazabicyclo[5.4.0]-undec-7-ene
Boc2O di-tert-butyl dicarbonate
DCE 1,2-Dichloroethane
DCM Dichloromethane DIAD Diisopropyl azodicarboxylate
DiBAl-H Diisobutylaluminum Hydride
DIPEA N-Ethyldiisopropylamine
DMA N,N-dimethylacetamide
DMAP Dimethylaminopyridine
DMF N,N'-Dimethylformamide
DMSO Dimethylsulfoxide
EDC 1-Ethyl-3-(3-dimethylaminopropyl)carbodiimide
EI Electrospray ionisation
$Et_2O$ Diethylether
$Et_3N$ Triethylamine
Ether Diethylether
EtOAc Ethyl acetate
EtOH Ethanol
FA Formic acid
FC Flash Chromatography
h hour(s)
HCl Hydrochloric acid
HOBt 1-Hydroxybenzotriazole
HPLC High Performance Liquid Chromatography
$H_2O$ Water
IPA isopropanol
L liter(s)
LC-MS Liquid Chromatography Mass Spectrometry
LiHMDS Lithium bis(trimethylsilyl)amide
Me methyl
MeI Iodomethane
MeOH Methanol
mg milligram
min minute(s)
mL milliliter
MS Mass Spectrometry
Pd/C palladium on charcoal
PG protecting group
Ph phenyl
$Ph_3P$ triphenyl phosphine
Prep Preparative
Rf ratio of fronts
RP reverse phase
Rt Retention time
rt Room temperature
SFC Supercritical Fluid Chromatography
$SiO_2$ Silica gel
T3P® Propylphosphonic acid anhydride
TBAF Tetrabutylammonium fluoride
TBDMS t-Butyldimethylsilyl
TEA Triethylamine
TFA Trifluoroacetic acid
THF Tetrahydrofuran
TLC Thin Layer Chromatography
TsCl toluene sulfonyl chloride Within the scope of this text, a readily removable group that is not a constituent of the particular desired end product of the compounds of the present invention is designated a "protecting group," unless the context indicates otherwise. The protection of functional groups by such protecting groups, the protecting groups themselves, and their cleavage reactions are described for example in standard reference works, such as e.g., Science of Synthesis: Houben-Weyl Methods of Molecular Transformation. Georg Thieme Verlag, Stuttgart, Germany. 2005. 41627 pp. (URL: http://www.science-of-synthesis.com (Electronic Version, 48 Volumes)); J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosauren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide und Derivate" (Chemistry of Carbohydrates: Monosaccharides and Derivatives), Georg Thieme Verlag, Stuttgart 1974. A characteristic of protecting groups is that they can be removed readily (i.e., without the occurrence of undesired secondary reactions) for example by solvolysis, reduction, photolysis or alternatively under physiological conditions (e.g., by enzymatic cleavage).

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g., the sodium salt of 2-ethyl hexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g., by treating the compounds with an acid or a suitable anion exchange reagent. Internal salts of compounds of the present invention containing acid and basic salt-forming groups, e.g., a free carboxy group and a free amino group, may be formed, e.g., by the neutralization of salts, such as acid addition salts, to the isoelectric point, e.g., with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallization and/or chromatographic separation, for example over silica gel or by, e.g., medium pressure liquid chromatography over a reversed phase column, and racemates can be separated, for example, by the formation of salts with optically pure salt-forming reagents and separation of the mixture of diastereoisomers so obtainable, for example by means of fractional crystallization, or by chromatography over optically active column materials.

Intermediates and final products can be worked up and/or purified according to standard methods, e.g., using chromatographic methods, distribution methods, (re-) crystallization, and the like.

EXAMPLES

The invention is illustrated by the following examples, which should not be construed as limiting. The assays used throughout the Examples are well established in the art: demonstration of efficacy in these assays is generally regarded as predictive of efficacy in subjects.

General Conditions:

Mass spectra were run on LC-MS systems using electrospray ionization. These were WATERS Acquity Single Quard Detector. [M+H]+ refers to mono-isotopic molecular weights. NMR spectra were run on open access Varian 400 or Varian 500 NMR spectrometers. Spectra were measured at 298K and were referenced using the solvent peak. Chemical shifts for $^1$H NMR are reported in parts per million (ppm).

Mass spectra were run on LC-MS systems with one of the following conditions:

1. Waters Acquity UPLC-H class system equipped with SQD detector.
Column: ACQUITY UPLC HSS C18 (50*2.1) mm, 1.8u.
Column temperature: Ambient.
Mobile Phase: A) 0.1% FA+5 mM Ammonium Acetate in Water.
B) 0.1% FA in Acetonitrile.
Gradient: 5-5% solvent B in 0.40 min, 5-35% solvent B in 0.80 min, 35-55% solvent B in 1.2 min,
55-100% solvent B in 2.5 min.
Flow rate: 0.55 mL/min.
Compounds were detected by a Waters Photodiode Array Detector.

2. Waters LCMS system equipped with ZQ 2000 detector.
Column: X-BRIDGE C18 (50*4.6) mm, 3.5 u.
Column temperature: Ambient.
Mobile Phase: A) 0.1% NH$_3$ in Water.
B) 0.1% NH$_3$ in Acetonitrile.
Gradient: 5-95% solvent B in 5.00 min.
Flow rate: 1.0 mL/min.
Compounds were detected by a Waters Photodiode Array Detector.

3. Waters ACQUITY UPLC system and equipped with a ZQ 2000 MS system.
Column: Kinetex by Phenomenex, 2.6 um, 2.1×50 mm
Column temperature: 50° C.
Gradient: 2-88% (or 00-45%, or 65-95%) solvent B over a 1.29 min period Flow rate: 1.2 mL/min.
Compounds were detected by a Waters Photodiode Array Detector.

Example 1: Synthesis of racemic 10-methoxy-11-(3-methoxypropoxy)-3,3-dimethyl-7-oxo-1,2,3,3a,7,12b-hexahydrocyclopenta[c]pyrido[2,1-a]isoquinoline-6-carboxylic acid [rac-1]

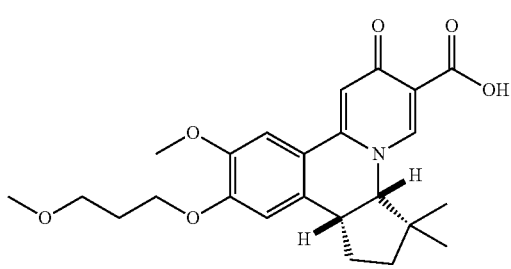

rac-1

Step 1: 5-(4-methoxy-3-(3-methoxypropoxy)phenyl)-2,2-dimethylcyclopentanone [1.1a]

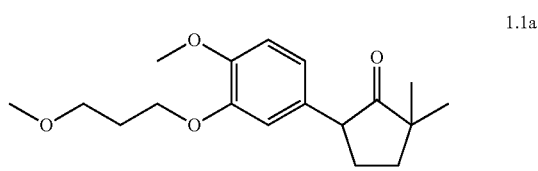

1.1a

A mixture of Pd(OAc)$_2$ (8.16 mg, 0.036 mmol), sodium tert-butoxide (0.454 g, 4.72 mmol), dicyclohexyl(2'-methyl-[1,1'-biphenyl]-2-yl)phosphane (32 mg), 2,2-dimethylcyclopentanone (0.547 ml, 4.36 mmol) and 4-bromo-1-methoxy-2-(3-methoxypropoxy)benzene (1 g, 3.63 mmol) in toluene (4.0 mL) was heated in a sealed vial at 50° C. for 18 hours. The mixture was diluted with EtOAc and filtered. The filtrate was concentrated and the remaining oil was purified by silica gel column chromatography, EtOAc/heptane 5 to 50%, to give product (500 mg, 45% yield). LC-MS (m/z): 307.2 [M+H]+. $^1$H NMR (400 MHz, CDCl$_3$): 7.72-7.28 (m, 1H), 6.94-6.61 (m, 2H), 4.10 (m, 2H), 3.91-3.77 (m, 4H), 3.65-3.49 (m, 2H), 3.41-3.27 (m, 3H), 2.36 (d, J=4.2 Hz, 1H), 2.19-1.88 (m, 4H), 1.88-1.71 (m, 1H), 1.21-1.11 (m, 3H), 1.07 (s, 3H)

Step 2: 5-(4-methoxy-3-(3-methoxypropoxy)phenyl)-2,2-dimethylcyclopentanamine [1.1 b]

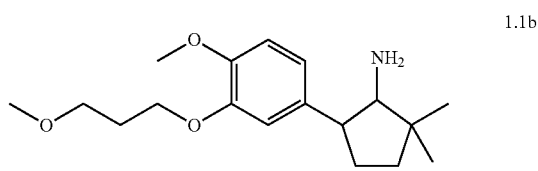

1.1b

To the mixture of 5-(4-methoxy-3-(3-methoxypropoxy)phenyl)-2,2-dimethylcyclopentanone (320 mg, 1.0 mmol) in MeOH (3 mL) was added acetic acid ammonia salt (1.6 g, 20.9 mmol) and sodium cyanoborohydride (656 mg, 10.4 mmol). The mixture was stirred at 80° C. for 8 hours and then was concentrated under reduced pressure. The remaining material was diluted with EtOAc, washed with water and brine, dried over Na$_2$SO$_4$ and concentrated. The crude material was used in the next step with no further purification. LCMS (m/z): 308.0 [M+H]+.

Step 3: N-(5-(4-methoxy-3-(3-methoxypropoxy)phenyl)-2,2 dimethylcyclopentyl)formamide [1.1c]

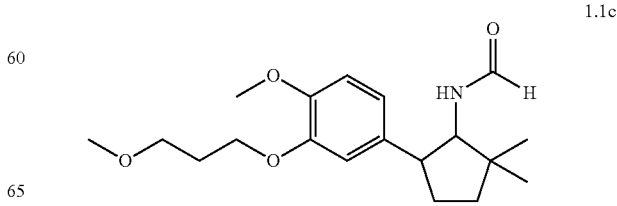

1.1c

To the mixture of 5-(4-methoxy-3-(3-methoxypropoxy)phenyl)-2,2-dimethylcyclopentanamine (320 mg, 1.041 mmol) in dioxane (3 ml) was added formic acid (0.160 mL, 4.16 mmol). The mixture was stirred at 100° C. for 6 hours. The mixture was concentrated to afford the crude product which was used in the next step with no further purification. LCMS (m/z): 336.2 [M+H]+.

Step 4: 7-methoxy-8-(3-methoxypropoxy)-3,3-dimethyl-2,3,3a,9b-tetrahydro-1H-cyclopenta[c]isoquinoline [1.1d-I] and [1.1d-II]

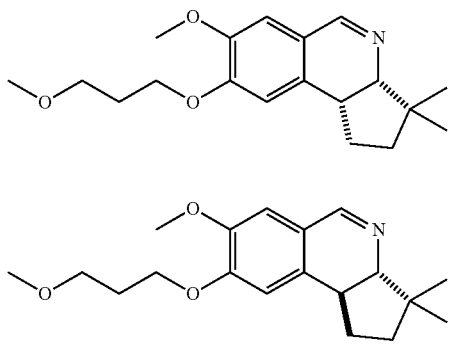

To a mixture of N-(5-(4-methoxy-3-(3-methoxypropoxy)phenyl)-2,2-dimethylcyclopentyl)formamide (349 mg, 1.04 mmol) in acetonitrile (1.8 ml) was added POCl₃ (140 μl, 1.50 mmol). The mixture was stirred at 85° C. for 2 hours and then concentrated. The residue was dissolved in EtOAc and basified by adding ammonium hydroxide solution. The phases were separated and the organic layer was washed with brine, dried over Na₂SO₄ and concentrated. The remaining material was purified by silica gel chromatography, acetone/heptane 5 to 50% to give product rac-1.1d-I and rac-1.1d-II.

Trans isomer rac-1.1d-II: (70 mg, 21% yield). LCMS (m/z): 318.3 [M+H]+. ¹H NMR (400 MHz, CDCl₃): 8.22 (s, 1H), 6.93-6.83 (m, 1H), 6.70 (s, 1H), 4.16 (t, J=6.4 Hz, 2H), 3.94-3.83 (m, 3H), 3.57 (q, J=4.7 Hz, 2H), 3.35 (d, J=1.5 Hz, 4H), 2.84 (s, 2H), 2.21-1.98 (m, 4H), 1.84-1.70 (m, 3H), 1.68-1.53 (m, 3H), 1.22 (s, 4H), 1.06 (s, 4H)

Cis isomer rac-1.1d-I: (54 mg, 16% yield). LCMS (m/z): 318.3 [M+H]+. 1H NMR (400 MHz, CDCl₃): 8.17 (s, 1H), 6.75 (s, 1H), 6.67 (s, 1H), 4.14 (t, J=6.2 Hz, 3H), 3.92-3.83 (m, 3H), 3.77 (d, J=10.3 Hz, 1H), 3.57 (t, J=5.4 Hz, 3H), 3.35 (d, J=1.6 Hz, 3H), 3.25 (q, J=9.4 Hz, 1H), 2.42-2.21 (m, 2H), 2.19-2.01 (m, 3H), 1.64 (dd, J=20.6, 7.8 Hz, 4H), 1.45 (t, J=8.0 Hz, 2H), 1.24 (d, J=6.1 Hz, 4H), 0.89 (s, 4H).

The relative configuration of rac-1.1d-I and rac-1.1d-II were confirmed by nuclear Overhauser effect (nOe) experiments.

Step 5: Ethyl 10-methoxy-11-(3-methoxypropoxy)-3,3-dimethyl-7-oxo-1,2,3,3a,7,8,8a,12b-octahydro-cyclopenta[c]pyrido[2,1-a]isoquinoline-6-carboxylate [rac-1.1 e]

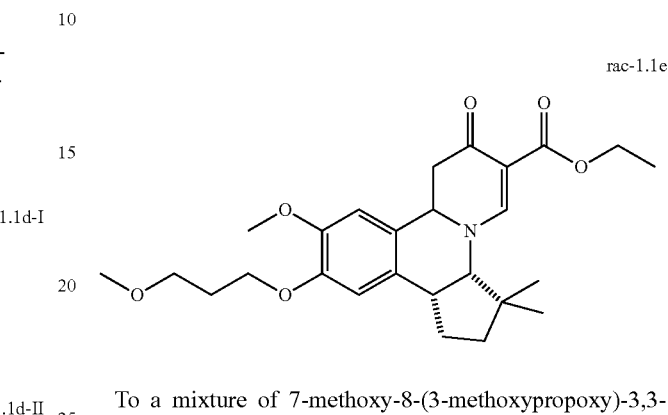

To a mixture of 7-methoxy-8-(3-methoxypropoxy)-3,3-dimethyl-2,3,3a,9b-tetrahydro-1H-cyclopenta[c]isoquinoline (cis isomer, rac-1.1d-I) (51 mg, 0.161 mmol) in EtOH (0.6 ml) was added (Z)-ethyl 2-(ethoxymethylene)-3-oxobutanoate (90 mg, 0.482 mmol). The mixture was stirred at 110° C. for 16 hours. After cooling, the mixture was concentrated and the crude material was used in the next step with no further purification. LCMS (m/z): 458.0 [M+H]+.

Step 6: Ethyl 10-methoxy-11-(3-methoxypropoxy)-3,3-dimethyl-7-oxo-1,2,3,3a,7,12b-hexahydrocyclopenta[c]pyrido[2,1-a]isoquinoline-6-carboxylate [rac-1.1f]

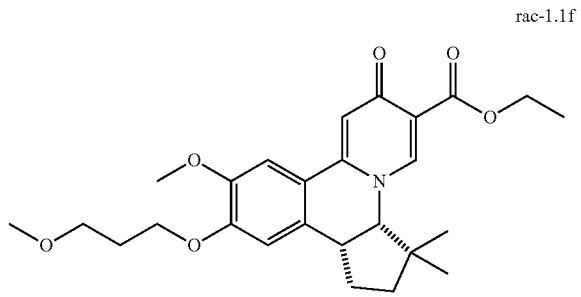

To a mixture of ethyl 10-methoxy-11-(3-methoxypropoxy)-3,3-dimethyl-7-oxo-1,2,3,3a,7,8,8a, 12b-octahydrocyclopenta[c]pyrido[2,1-a]isoquinoline-6-carboxylate (73.7 mg, 0.161 mmol) in DME (0.3 ml) was added p-chloranil (39.6 mg, 0.161 mmol). The mixture was stirred at 110° C. for 2 hours. After cooling to rt, the mixture was filtered and the solid was washed with cold DME. After drying, the desired product (28 mg, 38% yield) was a light yellow solid. LCMS (m/z): 456.0 [M+H]+.

Step 7: racemic 10-methoxy-11-(3-methoxy-propoxy)-3,3-dimethyl-7-oxo-1,2,3,3a,7,12b-hexahydrocyclopenta[c]pyrido[2,1-a]isoquinoline-6-carboxylic acid [rac-1]

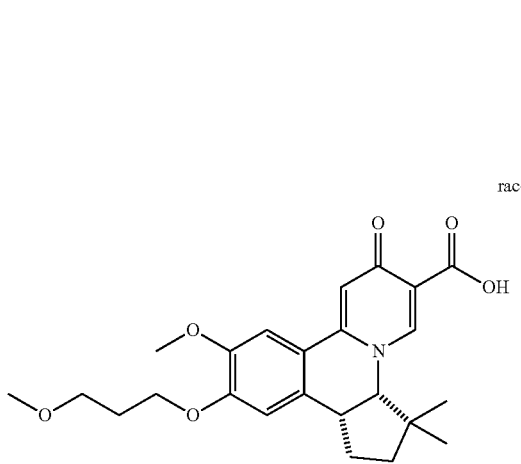

rac-1

To a mixture of ethyl 10-methoxy-11-(3-methoxypropoxy)-3,3-dimethyl-7-oxo-1,2,3,3a,7,12b-hexahydrocyclopenta[c]pyrido[2,1-a]isoquinoline-6-carboxylate (28 mg, 0.061 mmol) in THF (0.4 ml), MeOH (0.4 ml) and water (0.4 ml) was added LiOH (4.42 mg, 0.184 mmol). After stirring at rt for 2 hours, the mixture was concentrated and then acidified by adding 3.0 N HCl aq solution. To the mixture was added EtOAc. The organic layer was washed with water and brine, dried, and concentrated. The crude residue was purified by reverse phase HPLC to give product (5 mg, 19% yield). LCMS (m/z): 428.2 [M+H]$^+$. 1H NMR (400 MHz, CD$_3$CN): 8.41 (s, 1H), 7.33 (d, J=22.5 Hz, 2H), 6.97 (s, 1H), 4.38 (d, J=8.5 Hz, 1H), 4.17 (dtd, J=13.1, 9.6, 4.8 Hz, 2H), 3.91 (s, 3H), 3.80 (t, J=8.9 Hz, 1H), 3.53 (t, J=6.2 Hz, 3H), 3.32 (s, 3H), 2.32 (q, J=7.7 Hz, 4H), 2.13-2.00 (m, 3H), 1.65 (dt, J=13.2, 6.8 Hz, 2H), 1.45 (dt, J=12.9, 7.9 Hz, 1H), 1.22 (s, 3H), 0.48 (s, 3H).

Chiral Separation: (3aS,12bR)-10-methoxy-11-(3-methoxypropoxy)-3,3-dimethyl-7-oxo-1,2,3,3a,7,12b-hexahydrocyclopenta[c]pyrido[2,1-a]isoquinoline-6-carboxylic acid [1.1] and (3aR,12bS)-10-methoxy-11-(3-methoxypropoxy)-3,3-dimethyl-7-oxo-1,2,3,3a,7,12b-hexahydrocyclopenta[c]pyrido[2, 1-a]isoquinoline-6-carboxylic acid [1.2]

1.1

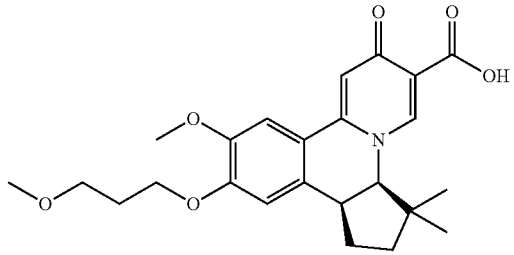

1.2

Compound rac-1 (40 mg, 0.090 mmol) was separated by chiral HPLC (Column: AD 21×250 mm, Heptane/IPA=30/70, flow rate 20 ml/min) to afford the two enantiomers 1.1 and 1.2.

Compound 1.1: tR 9.55 min; 8 mg 20% yield. LCMS (m/z): 428.2 [M+H]$^+$. 1H NMR (400 MHz, CD$_3$CN): 8.41 (s, 1H), 7.33 (d, J=22.5 Hz, 2H), 6.97 (s, 1H), 4.38 (d, J=8.5 Hz, 1H), 4.17 (dtd, J=13.1, 9.6, 4.8 Hz, 2H), 3.91 (s, 3H), 3.80 (t, J=8.9 Hz, 1H), 3.53 (t, J=6.2 Hz, 3H), 3.32 (s, 3H), 2.32 (q, J=7.7 Hz, 4H), 2.13-2.00 (m, 3H), 1.65 (dt, J=13.2, 6.8 Hz, 2H), 1.45 (dt, J=12.9, 7.9 Hz, 1H), 1.22 (s, 3H), 0.48 (s, 3H).

Compound 1:2: tR18.90 min, 8 mg, 20% yield. LCMS (m/z): 428.2 [M+H]$^+$. 1H NMR (400 MHz, CD$_3$CN): 8.41 (s, 1H), 7.33 (d, J=22.5 Hz, 2H), 6.97 (s, 1H), 4.38 (d, J=8.5 Hz, 1H), 4.17 (dtd, J=13.1, 9.6, 4.8 Hz, 2H), 3.91 (s, 3H), 3.80 (t, J=8.9 Hz, 1H), 3.53 (t, J=6.2 Hz, 3H), 3.32 (s, 3H), 2.32 (q, J=7.7 Hz, 4H), 2.13-2.00 (m, 3H), 1.65 (dt, J=13.2, 6.8 Hz, 2H), 1.45 (dt, J=12.9, 7.9 Hz, 1H), 1.22 (s, 3H), 0.48 (s, 3H).

Example 2: Synthesis of racemic 10-methoxy-11-(3-methoxypropoxy)-3,3-dimethyl-7-oxo-1,2,3,3a,7,12b-hexahydrocyclopenta[c]pyrido[2,1-a]isoquinoline-6-carboxylic acid [rac-2]

rac-2

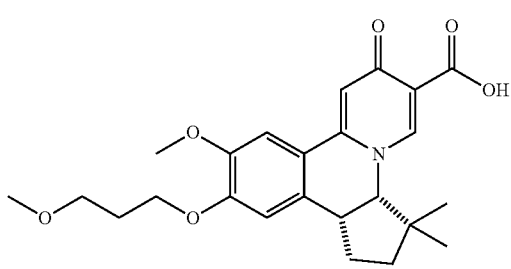

Using the trans-fused isomer from Step 4 of Example 1, the title compound was prepared by the same method used to make Example 1. LCMS (m/z): 428.2 [M+H]$^+$. 1H NMR (400 MHz, CD$_3$CN): δ 8.72 (s, 1H), 7.34 (s, 1H), 7.23 (s, 1H), 6.84 (s, 1H), 4.17 (q, J=6.4 Hz, 2H), 3.90 (s, 3H), 3.74 (d, J=13.5 Hz, 1H), 3.60-3.42 (m, 4H), 3.32 (s, 4H), 2.31 (dq, J=17.6, 7.9, 6.3 Hz, 2H), 2.10-2.00 (m, 3H), 1.52 (s, 4H), 1.29 (s, 4H)

Example 3.1: Synthesis of (3aS,12bR)-8-fluoro-10-methoxy-11-(3-methoxypropoxy)-3,3-dimethyl-7-oxo-1,2,3,3a,7,12b-hexahydrocyclopenta[c]pyrido[2,1-a]isoquinoline-6-carboxylic acid Step 1: ethyl (Z)-2-(ethoxymethylene)-4,4-difluoro-3-((trimethylsilyl)oxy)but-3-enoate [3.1a]

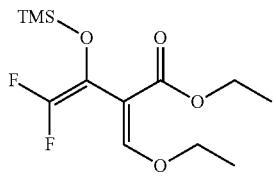

3.1a

Under an argon atmosphere, a mixture of Mg (3.69 g, 152 mmol)) and TMSCl (19.43 mL, 152 mmol) was treated with ultrasound irradiation for 15 min. To the mixture was added DMF (30 mL)), ethyl (Z)-2-(ethoxymethylene)-4,4-trifluoro-3-oxobutanoate (4.56 g, 19 mmol) was added dropwise at 50° C. under an argon atmosphere. The reaction mixture was stirred for additional 3 min. at 50° C. After removal of excess TMSCl in vacuo, the crude mixture was filtered and the filtrate (containing 3.1a and DMF) was used in the next step without further purification.

Step 2: ethyl 8-fluoro-10-methoxy-11-(3-methoxypropoxy)-3,3-dimethyl-7-oxo-1,2,3,3a,7,12b-hexahydrocyclopenta[c]pyrido[2,1-a]isoquinoline-6-carboxylate [3.1b-1] and [3.1b-2]

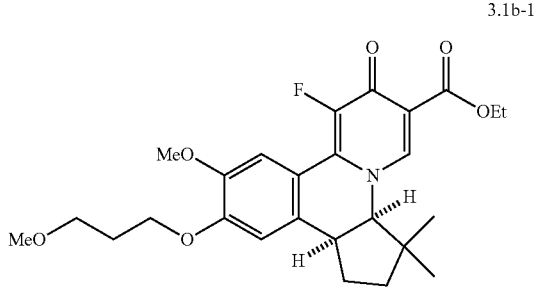 [SMILES: COCCCOc1cc2c(cc1OC)-c1c(F)c(=O)c(C(=O)O)cn1[C@H]1[C@@H]2CCC1(C)C]

3.1b-1

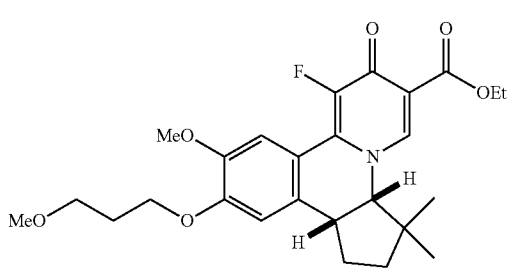

3.1b-2

To a suspension of ZnI$_2$ (920 mg, 2.88 mmol)) and 1.1d-I (915 mg, 2.88 mmol) in dry MeCN (10 mL), a solution of crude 3.1a (5091 mg, 17.30 mmol) in dry DMF (30 mL) was added dropwise at 50° C., and the reaction mixture was stirred overnight. The reaction mixture was poured into 10% HCl and extracted with DCM. The organic layer was washed with brine, and dried over MgSO$_4$. After filtration, the organic layer was concentrated and the crude oil purified by silica gel chromatography (0-10% MeOH/EtOAc) to afford rac-3.1b (1.2 g, 2.53 mmol, 88% yield)) as a pale yellow solid. The material was then purified by chiral SFC (AD column, flow rate 100 ml/min, CO$_2$/EtOH=70/30, 256 bar) to provide to provide products 3.1b-1 (tR 2.4 min) and 3.1b-2 (tR 4.4 min, 280 mg). LC-MS (m/z): 474.2 [M+H]$^+$.

Step 3: (3aS,12bR)-8-fluoro-10-methoxy-11-(3-methoxypropoxy)-3,3-dimethyl-7-oxo-1,2,3,3a,7,12b-hexahydrocyclopenta[c]pyrido[2,1-a]isoquinoline-6-carboxylic acid [3.1]

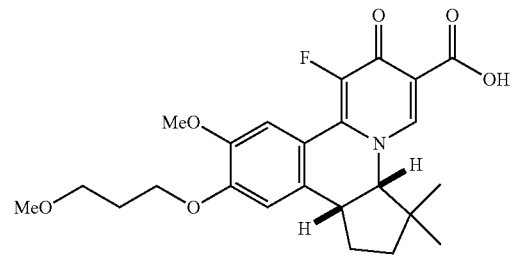

3.1

To the solution of 3.1b-2 (330 mg, 0.697 mmol) in THF (1 mL) was added NaOH (1.394 mL, 1.394 mmol). The reaction mixture was stirred for 2 h, then the reaction was acidified with 1.5 ml 1N HCl and extracted with dichloromethane. The organic layer was washed with brine, and dried over MgSO$_4$. After filtration and concentration, the resultant solid was recrystallized from hot EtOH/Water (5 ml; 5 ml) and the solids collected by vacuum filtration. The material was further lyophilized from MeCN and water to give product (230 mg, 0.511 mmol, 73.3%) as a tan solid. LC-MS (m/z): 446.4 [M+H]$^+$. $^1$H NMR (500 MHz, DMSO-d$^6$) 8.82 (s, 1H), 7.56 (s, 1H), 7.20 (s, 1H), 4.52 (d, J=5.5 Hz, 1H), 4.20-4.06 (m, 2H), 3.82 (s, 3H), 3.31 (dd, J=15.9, 4.8 Hz, 2H), 3.26 (s, 3H), 3.18 (d, J=15.9 Hz, 1H), 2.01 (p, J=6.3 Hz, 2H), 1.57-1.50 (m, 1H), 0.87 (d, J=6.6 Hz, 3H), 0.73 (d, J=6.7 Hz, 3H).

Compound 3.2 was synthesized from 3.1b-1 following step 3 procedure. LC-MS (m/z): 446.2 [M+H]$^+$.

Example 4.1: Synthesis of (3aR,12bR)-10-methoxy-11-(3-methoxypropoxy)-3,3-dimethyl-7-oxo-3,3a,7,12b-tetrahydro-2H-furo[3,2-c]pyrido[2,1-a]isoquinoline-6-carboxylic acid

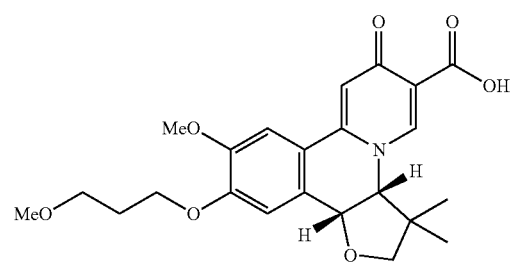

4.1

Step 1: 4-(benzyloxy)-1-(4-methoxy-3-(3-methoxypropoxy)phenyl)-3,3-dimethylbutan-2-one

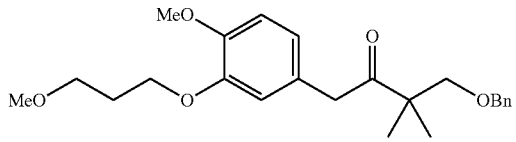

4.1a

A 250 mL oven-dried round-bottomed flask was charged with 4-bromo-1-methoxy-2-(3-methoxypropoxy)benzene (6.7 g, 24.35 mmol), XPhos (0.348 g, 0.731 mmol), Pd(OAc)$_2$ (0.082 g, 0.365 mmol) and purged with nitrogen. Dioxane (Volume: 32.5 ml) was added and the mixture stirred until homogeneous. LiHMDS (1.0 M in THF, 70.6 ml, 70.6 mmol) was added. 4-(Benzyloxy)-3,3-dimethylbutan-2-one (10.05 g, 48.7 mmol) in 4 mL dioxane was added slowly. The flask was fitted with a nitrogen-purged reflux condenser and then heated to 71° C. for 90 min. After cooling, the mixture was poured into water and the pH brought to 3 with 4 N HCl. The aqueous layer was extracted thrice with EtOAc, the combined organic layers were dried over Na$_2$SO$_4$, and then concentrated onto 16 g diatomaceous earth. The material was purified on a 120 g SiO$_2$ Combiflash cartridge (0->50% EtOAc in heptanes). The major UV active peak was concentrated to provide 4.1a (8.8 g, 21.97 mmol, 90% yield) as a yellow oil. LC-MS (m/z): 401.3 [M+H]$^+$. $^1$H NMR (400 MHz, CDCl$_3$): 7.28-7.36 (m, 5H), 6.79 (d, J=8.2 Hz, 1H) 6.6-6.7 (m, 2H), 4.51 (s, 2H), 4.04 (t, J=6.5 Hz), 2H), 3.83 (s, 3H), 3.75 (s, 2H), 3.55 (t, J=6.2 Hz, 2H), 3.51 (s, 2H), 3.34 (s, 3H), 2.07 (quint, J=6.3 Hz, 2H), 1.20 (s, 6H).

Step 2: 4-(benzyloxy)-1-(4-methoxy-3-(3-methoxypropoxy)phenyl)-3,3-dimethylbutan-2-amine [4.1b]

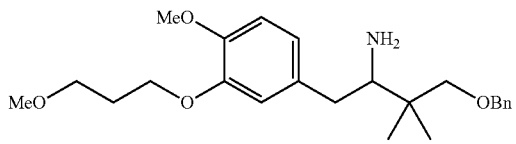

4.1b

A round-bottomed flask was charged with 4.1a (600. mg, 1.498 mmol) and methanol (1.5 mL). Ammonium acetate (1.732 g, 22.47 mmol) was added and the mixture was stirred at rt for 30 mins then sodium cyanoborohydride (471 mg, 7.49 mmol) was added. The mixture was heated at 60° C. until the reaction for 18 h. The reaction was quenched by adding 6 N NaOH and stirring for 30 min. The mixture was extracted twice with 2-Me-THF, the combined organic layers dried over Na$_2$SO$_4$, and then filtered and concentrated to provide crude 4.1b (602 mg, 1.498 mmol, 100% yield) that was used without further purification. LC-MS (m/z): 402.4 [M+H]$^+$.

Step 3: N-(4-(benzyloxy)-1-(4-methoxy-3-(3-methoxypropoxy)phenyl)-3,3-dimethylbutan-2-yl) formamide [4.1c]

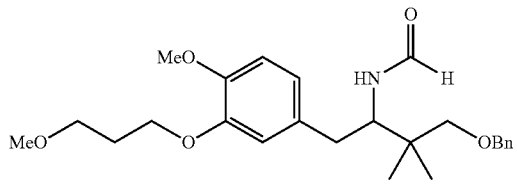

4.1c 4.1b (600 mg, 1.494 mmol) was taken up in DMF (2.3 ml) and cooled to 0° C. Triethylamine (1.04 mL, 7.5 mmol), was added followed by EDC (573 mg, 2.99 mmol) and formic acid (229 µl, 5.98 mmol). The mixture was stirred at rt for 2 hours. Water was added and the mixture was extracted with EtOAc. The combined organic layers were washed with 1.0 H aq HCl solution, brine, then dried over Na$_2$SO$_4$ and concentrated. The crude material was purified by silica gel (0->70% acetone in heptane) to give 4.1c (520 mg, 1.211 mmol, 81% yield) as a yellow oil. LC-MS (m/z): 430.3 [M+H]$^+$.

Step 4: 3-(1-(benzyloxy)-2-methylpropan-2-yl)-7-methoxy-6-(3-methoxypropoxy)-3,4-dihydroisoquinoline [4.1d]

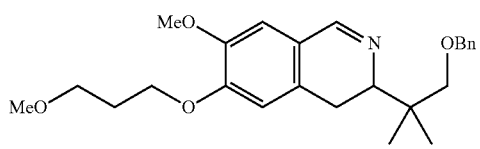

4.1d

A 200 mL round-bottomed flask was charged with 4.1c (4.71 g, 10.96 mmol) and purged with nitrogen. Acetonitrile (Volume: 43.8 ml) was added, and the flask cooled to 0-5° C. POCl$_3$ (1.532 ml, 16.44 mmol) was added dropwise. The flask was fitted with a dry condenser and the mixture was heated to 70° C. for 1 hr. The mixture was cooled to rt and the volatiles were removed on the rotary evaporator. The resultant oil was diluted with EtOAc and water, then basified with sat. NH$_4$OH until the aqueous layer reached pH 11. The layers were separated and the aqueous layer was extracted with EtOAc twice. The organic phases were combined, dried over Na$_2$SO$_4$, filtered and concentrated onto 6 g diatomaceous earth and purified on a 40 g SiO2 Combiflash column (0->60% acetone/heptane) to provide 4.1d (3.8 g, 84% yield) as an oil. LC-MS (m/z): 412.5 [M+H]$^+$.

Step 5: ethyl 6-(1-(benzyloxy)-2-methylpropan-2-yl)-10-methoxy-9-(3-methoxypropoxy)-2-oxo-6,7-dihydro-2H-pyrido[2,1-a]isoquinoline-3-carboxylate [4.1e]

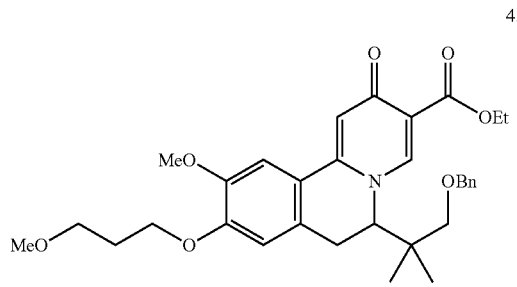

4.1e

To a solution of 4.1d (3.5 g, 8.50 mmol) in EtOH (Volume: 8.50 ml, Ratio: 1.000) was added (Z)-ethyl 2-(ethoxymethylene)-3-oxobutanoate (5.92 ml, 34.0 mmol) in a 20 mL microwave vial. The mixture was then sealed and flushed with nitrogen. The vial was heated at 110° C. for 18 hours. The reaction mixture was concentrated to dryness under vacuum. To the residue was added DME (Volume: 8.50 ml, Ratio: 1.000) and P-CHLORANIL (2.509 g, 10.21 mmol). The vial was sealed and heated at 100° C. for 1 hour. The solvent was removed and the residue loaded onto 12 g diatomaceous earth and purified by silica gel column chromatography (IPA/EtOAc 0->70%) to provide 4.1e (3.5 g, 75%) as a clear oil. LC-MS (m/z): 550.5 [M+H]$^+$.

Step 6: ethyl 6-(1-hydroxy-2-methylpropan-2-yl)-10-methoxy-9-(3-methoxypropoxy)-2-oxo-6,7-dihydro-2H-pyrido[2,1-a]isoquinoline-3-carboxylate [4.1f]

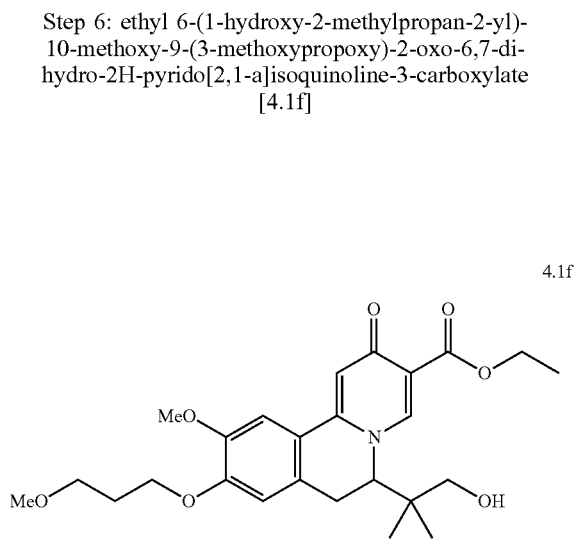

4.1f

A mixture of 4.1e (600 mg, 1.092 mmol) and 10% Pd/C (349 mg, 0.327 mmol) in EtOH (Volume: 10 mL) was purged with H$_2$ and stirred for 4 h. After filtration, the filtrate was concentrated to dryness to give the crude material which was purified by silica gel chromatography (0-50% MeOH/EtOAc) to give 4.1f (353 mg, 0.768 mmol, 70.4% yield) as an oil. LC-MS (m/z): 460.3 [M+H]$^+$.

Step 7: ethyl (3aR*, 12bR*)-10-methoxy-11-(3-methoxypropoxy)-3,3-dimethyl-7-oxo-3,3a,7,12b-tetrahydro-2H-furo[3,2-c]pyrido[2,1-a]isoquinoline-6-carboxylate [4.1 g]

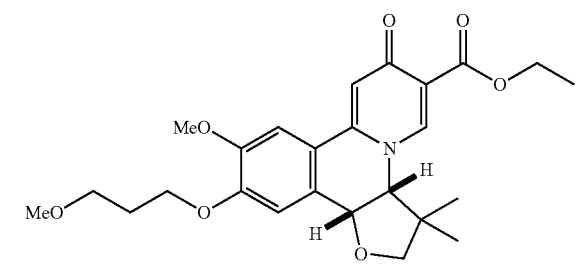

4.1g

To a solution of 4.1f (311 mg, 0.677 mmol) in acetonitrile (9 mL) was added a solution of CuSO$_4$ (108 mg, 0.677 mmol) and K$_2$S$_2$O$_8$ (366 mg, 1.354 mmol) in water (Volume: 1.9 mL). The resulting mixture was stirred at reflux for 1 hour. The mixture was added 100 mL ethyl acetate, washed with water, brine and dried over Na$_2$SO$_4$. The organic phase was concentrated and the residue was used in the next step without further purification. The crude residue was treated with a mixture of 2 mL AcOH/0.1 mL H$_2$SO$_4$. After stirred for 20 mins at room temperature, the mixture was added 100 ml DCM, washed with saturated NaHCO$_3$, dried over Na$_2$SO$_4$. The organic phase was concentrated and the residue was purified by silica get chromatography (0-70% IPA/EA) to give product 4.1g (180 mg, 60.4%).

Step 8: (3aR,12bR)-10-methoxy-11-(3-methoxypropoxy)-3,3-dimethyl-7-oxo-3,3a,7,12b-tetrahydro-2H-furo[3,2-c]pyrido[2,1-a]isoquinoline-6-carboxylic acid [4.1]

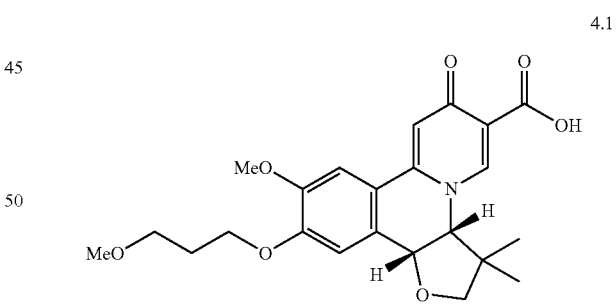

4.1

LiOH (3.28 ml, 6.56 mmol) in water was added to a solution of 4.1g (1.2 g, 2.62 mmol) in THF (8.74 ml) and the mixture was stirred for 30 min. The solution was then acidified by adding 4.0 N HCl, diluted with water, and extracted thrice with DCM. The combined organic layers were dried over Na$_2$SO$_4$, filtered and concentrated. The material was purified by chiral chromatography (AD column, SFC 5 mL/min, CO$_2$/IPA=70/30), and returned as 4.1 (1.36 min) and 4.2 (1.86 min). 4.1 (348 mg, 0.802 mmol, 30.6% yield) was a fluffy solid after lyophilization from MeCN/H$_2$O. LC-MS (m/z): 430.4 [M+H]$^+$. $^1$H NMR (500 MHz, DMSO-d6): 8.60 (s, 1H), 7.66 (s, 1H), 7.56 (s, 1H), 7.06 (s, 1H), 5.54 (d, J=8.8 Hz, 1H), 4.96 (d, J=8.5 Hz, 1H), 4.11 (m, 2H), 3.91 (s, 3H), 3.70 (d, J=8.8 Hz, 1H), 3.48 (t, J=6.4 Hz, 2H), 3.37 (d, J=9.0 Hz, 1H), 3.25 (s, 3H), 1.99 (quint, J=6.6 Hz, 2H), 1.25 (s, 3H), 0.46 (s, 3H).

Example 5: Synthesis 10-chloro-11-(3-methoxypropoxy)-3,3-dimethyl-7-oxo-1,2,3,3a,7,12b-hexahydrocyclopenta[c]pyrido[2,1-a]isoquinoline-6-carboxylic acid [5.1] and [5.2]

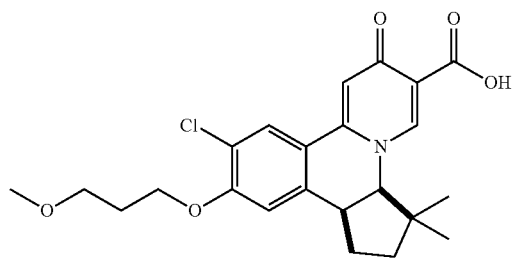

Step 1:
4-bromo-1-chloro-2-(3-methoxypropoxy)benzene [5a]

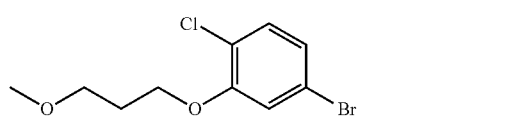

To a mixture of 5-bromo-2-chlorophenol (15 g, 72.3 mmol), and 1-bromo-3-methoxypropane (9.7 ml, 87 mmol) in DMF (40 ml) at rt was added K$_2$CO$_3$ (20 g, 145 mmol), and the resultant mixture was stirred at 50° C. for 16 hours. The mixture was then filtered, and the filtrate was concentrated. The residue was purified by silica gel column chromatography, EtOAc/heptane 0 to 30% to give product (18.4 g, 91% yield). $^1$H NMR (400 MHz, Acetonitrile-d3): 7.38-7.20 (m, 2H), 7.10 (dd, J=8.4, 2.1 Hz, 1H), 4.13 (t, J=6.3 Hz, 2H), 3.54 (t, J=6.2 Hz, 2H), 3.31 (s, 3H), 2.09-1.98 (m, 2H).

Step 2: 5-(4-chloro-3-(3-methoxypropoxy)phenyl)-2,2-dimethylcyclopentanone [5b]

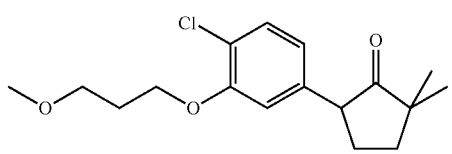

A mixture of Pd(OAc)$_2$ (60 mg, 0.268 mmol), sodium tert-butoxide (3.35 g, 34.9 mmol), dicyclohexyl(2'-methyl-[1,1'-biphenyl]-2-yl)phosphane (230 mg), 2,2-dimethylcyclopentanone (4.04 ml, 32.2 mmol) and 4-bromo-1-methoxy-2-(3-methoxypropoxy)benzene (7.5 g, 26.8 mmol) in toluene (30.0 mL) was heated in a sealed vial at 50° C. under nitrogen atmosphere for 6 hours. The mixture was diluted with EtOAc and filtered. The filtrated solution was concentrated and the remaining oil was purified by silica gel column chromatography, EtOAc/heptane 5 to 50%, to give product (3 g, 36% yield). LC-MS (m/z): 311.2 [M+H]$^+$.

Step 3: 5-(4-Chloro-3-(3-methoxypropoxy)phenyl)-2,2-dimethylcyclopentanamine [5c]

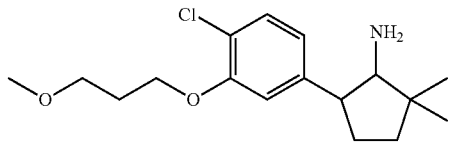

To the mixture of 5-(4-chloro-3-(3-methoxypropoxy)phenyl)-2,2-dimethylcyclopentanone (3 g, 9.65 mmol) in MeOH (30 mL) was added acetic acid ammonia salt (14.8 g, 192 mmol) and sodium cyanoborohydride (6.06 g, 97 mmol). The mixture was stirred at 70° C. for 16 hours and then was concentrated under reduced pressure. The remaining material was diluted with EtOAc, washed with water and brine, dried over Na$_2$SO$_4$ and concentrated. The crude material was used in the next step with no further purification. LCMS (m/z): 312.0 [M+H]$^+$.

Step 4: N-(5-(4-chloro-3-(3-methoxypropoxy)phenyl)-2,2 dimethylcyclopentyl)formamide [5d]

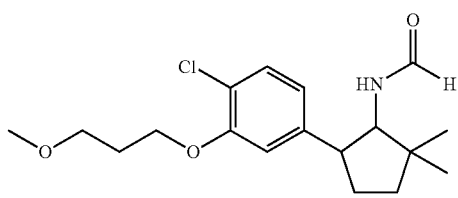

To the mixture of 5-(4-chloro-3-(3-methoxypropoxy)phenyl)-2,2-dimethylcyclopentanamine (3 g, 9.65 mmol) in dioxane (25 ml) was added formic acid (1.48 ml, 38.6 mmol). The mixture was stirred at 100° C. for 6 hours. The

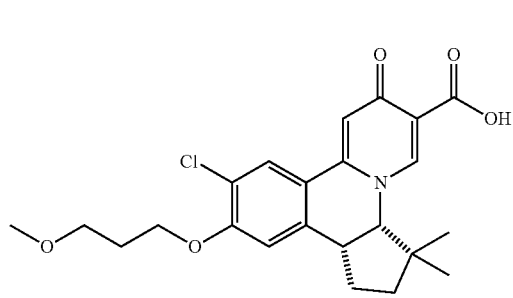

mixture was concentrated to afford the crude product which was used in the next step with no further purification. LCMS (m/z): 340.2 [M+H]+.

Step 5: 7-chloro-8-(3-methoxypropoxy)-3,3-dimethyl-2,3,3a,9b-tetrahydro-1H-cyclopenta[c]isoquinoline [rac-5e-1 and rac-5e-2]

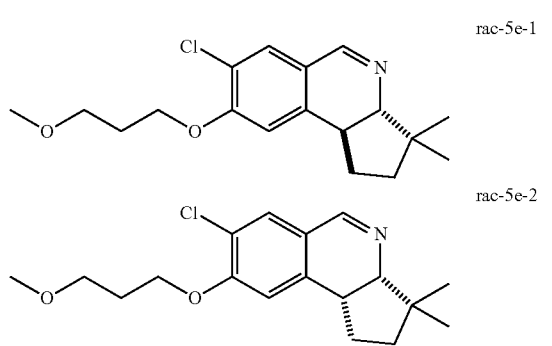

To a mixture of N-(5-(4-chloro-3-(3-methoxypropoxy)phenyl)-2,2-dimethylcyclopentyl)formamide (3.28 g, 9.65 mmol) in acetonitrile (17 ml) was added POCl₃ (1.35 ml, 14.5 mmol). The mixture was stirred at 85° C. for 2 hours and then concentrated. The residue was dissolved in EtOAc and basified by adding ammonium hydroxide solution. The phases were separated and the organic layer was washed with brine, dried over Na₂SO₄ and concentrated. The remaining material was purified by silica gel chromatography, acetone/heptane 5 to 50% to give product rac-5e-1 and rac-5e-2.

Less polar product: rac-5e-1 trans isomer (590 mg, 19% yield). LCMS (m/z): 322.3 [M+H]+.

More polar product: rac-5e-2 cis isomer (470 mg, 15% yield). LCMS (m/z): 322.3 [M+H]+. ¹H NMR (400 MHz, Chloroform-d) δ 8.15 (s, 1H), 7.25 (s, 2H), 6.69 (s, 1H), 4.14 (s, 3H), 3.78 (d, J=10.1 Hz, 1H), 3.60 (s, 3H), 3.43-3.32 (m, 4H), 3.26 (q, J=9.5, 9.1 Hz, 2H), 2.47-2.19 (m, 3H), 2.16-2.02 (m, 4H), 1.66 (d, J=10.1 Hz, 4H), 1.46 (t, J=8.6 Hz, 3H), 1.23 (s, 4H), 1.16-1.00 (m, 3H), 0.88 (s, 4H)

The relative configuration of rac-5e-1 and rac-5e-2 was established by nuclear Overhauser effect (NOE) experiments.

Step 6: Ethyl 10-chloro-11-(3-methoxypropoxy)-3,3-dimethyl-7-oxo-1,2,3,3a,7,8,8a,12b-octahydrocyclopenta[c]pyrido[2,1-a]isoquinoline-6-carboxylate [rac-5f]

rac-5f

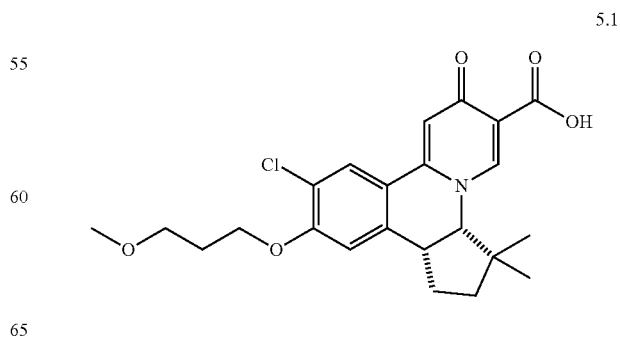

To a mixture of 7-chloro-8-(3-methoxypropoxy)-3,3-dimethyl-2,3,3a,9b-tetrahydro-1H-cyclopenta[c]isoquinoline (cis isomer, rac-5e-2) (470 mg, 1.46 mmol) in EtOH (5 ml) was added (Z)-ethyl 2-(ethoxymethylene)-3-oxobutanoate (816 mg, 4.38 mmol). The mixture was stirred at 110° C. for 16 hours. After cooling, the mixture was concentrated and the crude material was used in the next step with no further purification. LCMS (m/z): 462.0 [M+H]+.

Step 7: Ethyl (3aS,12bR)-10-chloro-1-(3-methoxypropoxy)-3,3-dimethyl-7-oxo-1,2,3,3a,7,12b-hexahydrocyclopenta[c]pyrido[2,1-a]isoquinoline-6-carboxylate [5g-1] and [5g-2]

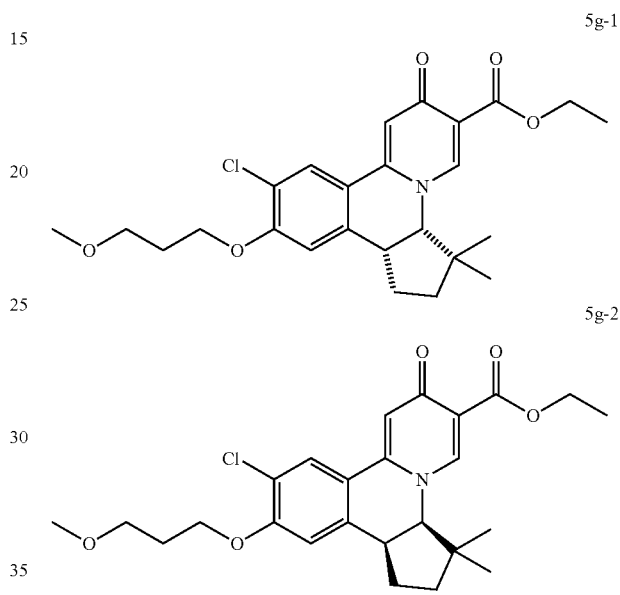

To a mixture of rac-5f ((673.7 mg, 1.461 mmol) in DME (3.5 ml) was added p-chloranil (359.6 mg, 1.461 mmol) and the mixture was stirred at 110° C. for 2 hours. After cooling to rt, the mixture was concentrated and the residue was purified by silica gel column chromatography, MeOH/DCM 0 to 6%, to give product (180 mg). LCMS (m/z): 460.0 [M+H]+. This product was separated by chiral SFC (AD column, flow rate 100 ml/min, CO₂/MeOH=75/25) to give two enantiomers: 5g-1 (tR 3.55 min, 70 mg, 11% yield) and 5g-2 (tR 4.91 min, 70 mg, 11% yield).

Step 8: (3aS,12bR)-10-chloro-11-(3-methoxypropoxy)-3,3-dimethyl-7-oxo-1,2,3,3a,7,12b-hexahydrocyclopenta[c]pyrido[2,1-a]isoquinoline-6-carboxylic acid [5.1]

5.1

To a mixture of 5g-1 (70 mg, 0.152 mmol) in EtOH (1 ml) was added NaOH (5 M, 0.152 ml, 0.761 mmol). After stirring at rt for 2 hours, the mixture was concentrated and then acidified by adding 3.0 N HCl aq solution. To the mixture was added EtOAc. The organic layer was washed with water and brine, dried, and concentrated. The crude residue was purified by silica gel column chromatography, MeOH in DCM 0 to 5%, to give product (50 mg, 75% yield). LCMS (m/z): 432.2 [M+H]+. 1H NMR (400 MHz, Acetonitrile-d3): 8.40 (s, 1H), 8.01 (s, 1H), 7.22 (s, 1H), 7.09 (s, 1H), 4.39 (d, J=8.6 Hz, 1H), 4.24 (ddt, J=15.9, 9.6, 4.8 Hz, 2H), 4.08 (q, J=7.1 Hz, 4H), 3.83 (t, J=6.8 Hz, 1H), 3.57 (t, J=6.1 Hz, 2H), 3.32 (s, 3H), 2.48-2.24 (m, 3H), 2.15 (s, 2H), 2.07 (p, J=6.2 Hz, 3H), 1.66 (ddd, J=13.9, 8.1, 6.0 Hz, 1H), 1.56-1.40 (m, 1H), 1.28-1.16 (m, 8H), 0.47 (s, 3H).

Step 9: (3aR,12bS)-10-chloro-11-(3-methoxypropoxy)-3,3-dimethyl-7-oxo-1,2,3,3a,7,12b-hexahydrocyclopenta[c]pyrido[2,1-a]isoquinoline-6-carboxylic acid [5.2]

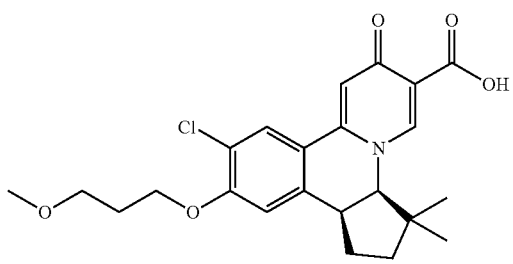

5.2

To a mixture of 5g-2 (70 mg, 0.152 mmol) in EtOH (1 ml) was added NaOH (5 M, 0.152 ml, 0.761 mmol). After stirring at rt for 2 hours, the mixture was concentrated and then acidified by adding 3.0 N HCl aq solution. To the mixture was added EtOAc. The organic layer was washed with water and brine, dried, and concentrated. The crude residue was purified by silica gel column chromatography, MeOH in DCM 0 to 5%, to give product (59 mg, 79% yield). LCMS (m/z): 432.2 [M+H]+. 1H NMR (400 MHz, Acetonitrile-d3): 8.40 (s, 1H), 8.01 (s, 1H), 7.22 (s, 1H), 7.09 (s, 1H), 4.39 (d, J=8.6 Hz, 1H), 4.24 (ddt, J=15.9, 9.6, 4.8 Hz, 2H), 4.08 (q, J=7.1 Hz, 4H), 3.83 (t, J=6.8 Hz, 1H), 3.57 (t, J=6.1 Hz, 2H), 3.32 (s, 3H), 2.48-2.24 (m, 3H), 2.15 (s, 2H), 2.07 (p, J=6.2 Hz, 3H), 1.66 (ddd, J=13.9, 8.1, 6.0 Hz, 1H), 1.56-1.40 (m, 1H), 1.28-1.16 (m, 8H), 0.47 (s, 3H).

Example 6: 10-methoxy-11-(3-methoxypropoxy)-7-oxo-1,2,3,3a,7,12b-hexahydrocyclopenta[c]pyrido[2,1-a]isoquinoline-6-carboxylic acid [6.1 and 6.2]

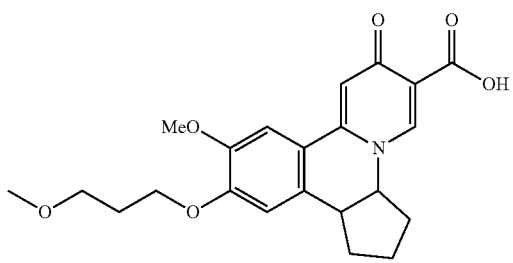

6.1 and 6.2

Step 1. 2-(4-methoxy-3-(3-methoxypropoxy)phenyl)cyclopentan-1-one. [6a]

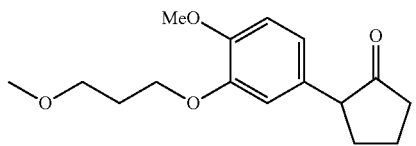

6a

To a solution of 4-bromo-1-methoxy-2-(3-methoxypropoxy)benzene (5 g, 18.24 mmol) in 1,4-Dioxane (100.0 mL) was added NaOAc (1.49 g 18.24 mmol), cyclopentanone (4.59 g, 54.74 mmol), pyrrolidine (0.259 g, 3.64 mmol), P(O-Tol)₃ (0.222 g, 0.72 mmol.) and 1,1,3,3-Tetramethylbutylamine (0.471 g, 3.64 mmol) at room temperature under nitrogen atmosphere. The reaction mixture was purged with nitrogen. To the above reaction mixture, Pd(OAc)₂ (0.0817 g, 0.364 mmol) was added and the mixture was again purged with nitrogen and then heated at 110° C. for 15 hs. After cooled at rt, the reaction mixture was filtered through celite bed, the bed was further washed with ethyl acetate. The filtrate was washed with water, brine, and dried over sodium sulfate, filtered, and concentrated. The residue was purified by silica gel column chromatography, (EtOAc/Hexane, 20-30%) to give product. LCMS(m/z): 279.35 [M+H]+

Step 2. 1-(4-methoxy-3-(3-methoxypropoxy)phenyl)-3,3-dimethylbutan-2-amine. [6b]

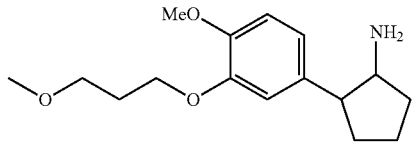

6b

NH₄OAc (8.73 g, 113 mmol) and NaBH₃CN (0.949 g, 15.1 mmol) were added temperature to a solution of 6a (2.1 g, 7.55 mmol) in MeOH (15.1 mL) at rt and the resulting mixture was stirred at room temperature for 18 hours. The reaction was then quenched by adding 20% NaOH aqueous solution and stirred at rt for 20 minutes. The reaction mixture was extracted with EtOAc. The organic layer was washed with water, brine, dried over sodium sulfate and concentrated to give product 6b (2.1g crude). LCMS(m/z):281.2 [M+H]+

Step 3. N-(1-(4-methoxy-3-(3-methoxypropoxy)phenyl)-3,3-dimethylbutan-2-yl)formamide [6c]

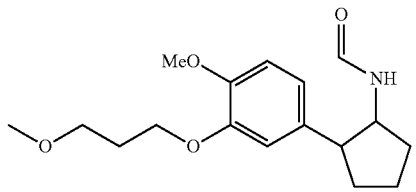

6c

To a solution of 6b (2.0g, 7.16 mmol) in DMF (11.9 mL) at 0° C. was added EDC.HCl (2.73g, 14.3 mmol), DIPEA (2.77g, 21.5 mmol), followed by formic acid (1.31g, 28.6 mmol). After stirred at rt for 1 h, cold water was added to above reaction mixture and the mixture was extracted with EtOAc. The organic layer was washed with 10% NaHCO₃ aq. solution, 10% HCl aq. solution, water and brine. The separated organic layer was dried over sodium sulfate, filtered and concentrated to give product. 6c (1.4 g). The crude material was used in the next step with no further purification. LCMS (m/z): 308.1 [M+H]⁺

Step 4. 7-methoxy-8-(3-methoxypropoxy)-2,3,3a, 9b-tetrahydro-1H-cyclopenta[c]isoquinoline. [6d-1] and [6d-2]

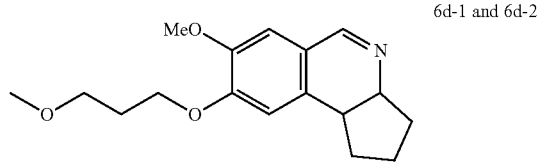 [SMILES: COCCCOc1cc2c(cc1OC)C=NC1CCCC21]

6d-1 and 6d-2

POCl₃ (0.778 g, 5.07 mmol) was added to a solution of 6c (1.30 g, 4.23 mmol) in CH₃CN (21.15 mL) at 0° C. and the reaction mixture was heated at 80° C.) for 3 hours. The reaction mixture was concentrated under vacuum and the residue was dissolved in ethyl acetate. Ammonia solution (27% in water) was added under stirring until the pH=11. The mixture was then extracted with ethyl acetate. The combined ethyl acetate layers was washed with water, brine, dried over sodium sulfate and concentrated. The residue was purified by silica gel column chromatography gave two isomers. 6d-1 (0.425 g, less polar product) and 6d-2 (0.3 g, more polar isomer).

6d-1: LCMS (m/z): 290.1 [M+H]⁺. ¹H NMR (400 MHz, CDCl₃): 8.23 (d, J=3.1 Hz, 1H), 6.92 (s, 1H), 6.75 (d, J=8.8 Hz, 1H), 4.19 (t, J=6.5 Hz, 2H), 3.90 (s, 3H), 3.60 (t, J=6.0 Hz, 3H), 3.39 (d, J=9.1 Hz, 4H), 3.21-3.15 (m, 1H), 2.60-2.51 (m, 1H), 2.30-2.11 (m, 5H), 1.98-1.90 (m, 2H), 1.82 (dt, J=19.6, 11.4 Hz, 2H).

6d-2: LCMS (m/z): 290.1 [M+H]⁺. ¹H NMR (400 MHz, CDCl₃): 8.16 (s, 1H), 6.84 (s, 1H), 6.75 (s, 1H), 4.18 (t, J=6.4 Hz, 2H), 3.90 (s, 3H), 3.60 (t, J=6.0 Hz, 2H), 3.38 (s, 3H), 2.91 (dd, J=17.4, 8.6 Hz, 1H), 2.34 (dd, J=14.8, 7.0 Hz, 1H), 2.20-2.10 (m, 3H), 2.08-1.95 (m, 3H), 1.67-1.55 (m, 3H), 1.60-1.44 (m, 2H), 0.97-0.82 (m, 2H).

Step 5. Ethyl 10-methoxy-11-(3-methoxypropoxy)-7-oxo-1,2,3,3a,7,12b-hexahydrocyclopenta[c]pyrido [2,1-a]isoquinoline-6-carboxylate [6e-1]

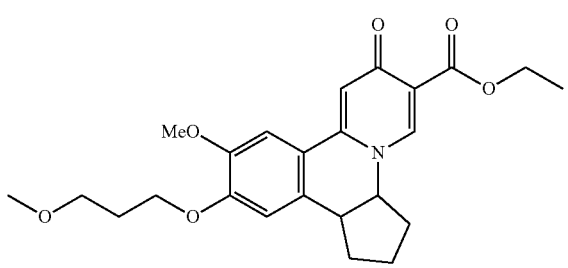

6e-1

A solution of 6d-1 (0.425 g, 1.45 mmol) and ethyl (E)-2-(ethoxymethylene)-3-oxobutanoate (0.810g, 4.35 mmol) in EtOH (9 ml) was heated at 110° C. for 18 hours. The mixture was then concentrated under vacuum and the residue was dissolved in DME (20.0 mL). p-chloranil (0.426 g, 1.73 mmol) was added and the reaction mixture was heated to reflux for 2 hours. After volatile solvent was removed under vacuum, diethyl ether was added. The precipitate was collected by filtration to afford product. LCMS (m/z):428.3 [M+H]⁺.

Step 6. 10-methoxy-11-(3-methoxypropoxy)-7-oxo-1,2,3,3a,7,12b-hexahydrocyclopenta[c]pyrido[2,1-a] isoquinoline-6-carboxylic acid [6.1] and [6.2]

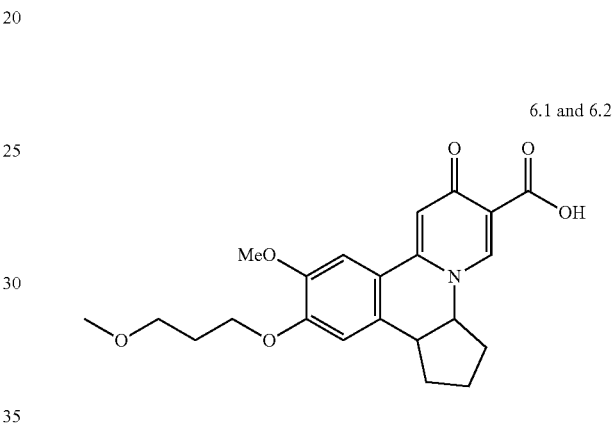

6.1 and 6.2

To a solution of 6e-1 (0.075 g, 0.175 mmol) in MeOH (6.0 mL), LiOH.2H₂0 (0.014 g, 0.35 mmol) was added followed by the addition of water (2.0 mL) at rt. The reaction mixture was then stirred at rt for 2 hours. After completion of reaction, the reaction mixture was concentrated under vacuum. The residue was dissolved into cold water and was acidified to pH 4-5 using dil. HCl. The obtained solid was filtered, washed with cold water and diethyl ether. The solid was dried well under vacuum to give off white solid as the desired product 6.1 (0.029g, 41% yield). LCMS (m/z):[M+H]+ 400.0. ¹H NMR (400 MHz, DMSO): 16.83 (s, 1H), 8.80 (s, 1H), 7.54 (d, J=3.3 Hz, 2H), 7.07 (s, 1H), 5.01-4.74 (m, 1H), 4.29-4.00 (m, 2H), 3.89 (s, 3H), 3.57 (s, 1H), 3.48 (t, J=6.2 Hz, 2H), 3.34 (s, 3H), 2.37 (s, 1H), 2.23 (d, J=8.5 Hz, 1H), 2.08 (d, J=6.6 Hz, 1H), 2.01-1.90 (m, 2H), 1.64 (s, 1H), 1.49 (s, 2H).

Compound 6.2 was synthesized from compound 6d-2 following the procedures Step 5-6 described for the synthesis of 6.1. LCMS (m/z): [M+H]+ 400.0. ¹H NMR (400 MHz, DMSO): 16.77 (s, 1H), 8.38 (s, 1H), 7.52 (d, J=20.7 Hz, 2H), 6.85 (s, 1H), 4.13 (t, J=6.4 Hz, 2H), 3.89 (s, 3H), 3.48 (t, J=6.2 Hz, 2H), 3.26 (s, 3H), 3.09 (dd, J=19.7, 12.1 Hz, 1H), 2.38 (s, 1H), 2.10-1.92 (m, 5H), 1.70 (s, 1H).

Note: isomers 6.1 and 6.2 were isolated and tested separately, but the stereochemistry of the isomers was not apparent from their nmr data.

Example 7: (3aR,12bR)-8-fluoro-10-methoxy-11-(3-methoxypropoxy)-3,3-dimethyl-7-oxo-3,3a,7,12b-tetrahydro-2H-furo[3,2-c]pyrido[2,1-a]isoquinoline-6-carboxylic acid [7.1]

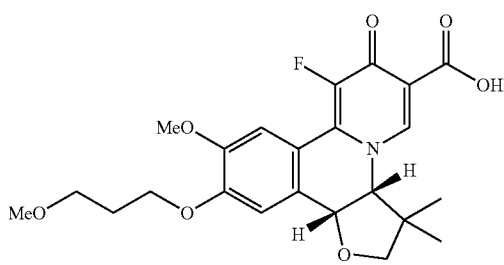

Step 1: 4-hydroxy-1-(4-methoxy-3-(3-methoxypropoxy)phenyl)-3,3-dimethylbutan-2-one [7.1a]

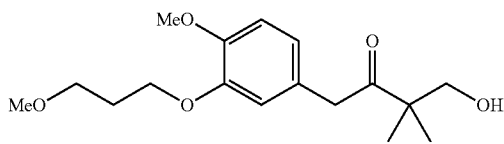

A mixture of 4.1a (8.8g, 21.97 mmol) and 10% Pd/C (2.1 g, 1.973 mmol) in MeOH (110 ml) was purged with vacuum and $H_2$ was stirred for 2 days. The atmosphere was purged with vacuum, and the mixture was filtered through diatomaceous earth with MeOH washes, and concentrated to provide a grey oil that was taken up in EtOAc and passed through a small pad of $SiO_2$, and the concentrated to provide 7.1a (6.66g, 21.46 mmol, 98% yield) as a yellow oil. LC-MS (m/z): 311.3 [M+H]$^+$. $^1$H NMR (500 MHz, CDCl$_3$): 6.82 (d, J=8.24 Hz, 1H), 6.73 (s, 1H), 6.70 (d, J=8.10 Hz, 1H), 4.10 (t, J=6.41 Hz, 2H), 3.84 (s, 3H), 3.74 (s, 2H), 3.55-3.60 (m, 4H), 3.35 (s, 3H), 2.36 (br, 1H), 2.10 (quin, J=6.33 Hz, 2H), 1.23 (s, 6H).

Step 2: 2-(4-methoxy-3-(3-methoxypropoxy)phenyl)-4,4-dimethyldihydrofuran-3(2H)-one [7.1b]

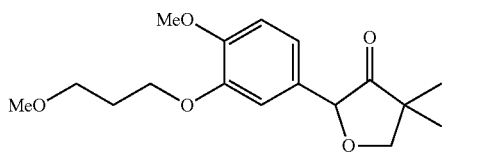

A 2-neck, oven dried 250 mL round-bottomed flask was fitted a pressure-equalizing addition funnel and with charged with 7.1a (6.63 g, 21.36 mmol) and 50 mL DCM. The flask was cooled to 0° C. The addition funnel was charged with Br$_2$ (1.045 ml, 20.29 mmol) in 485 mL DCM, which was added dropwise over ~25 min. Immediately after complete addition, the mixture was poured in to 200 mL sat aq. Na$_2$S$_2$O$_3$ and stirred for 20 min. The mixture was extracted thrice with EtOAc. The combined organic layers were dried over Na$_2$SO$_4$, filtered, and concentrate onto 13 g diatomaceous earth. The crude material was purified on a 80 g RediSep SiO$_2$ cartridge (0-60% EtOAc in heptanes) to provide 7.1b (3.89g, 12.61 mmol, 59.1% yield) as a yellow oil from the first major UV-active peak. LC-MS (m/z): 309.3 [M+H]$^+$. $^1$H NMR (400 MHz, CDCl$_3$): 6.97 (s, 1H), 6.96 (d, J=7.96 Hz, 1H), 6.87 (br d, J=8.12 Hz, 1H), 4.76 (s, 1H), 4.08-4.17 (m, 3H), 3.96 (d, J=9.2 Hz, 1H), 3.85 (s, 3H), 3.57 (t, J=6.13 Hz, 2H), 3.35 (s, 3H), 2.10 (quint, J=6.3 Hz, 2H), 1.20 (s, 3H), 1.16 (s, 3H).

Step 3: N-(2-(4-methoxy-3-(3-methoxypropoxy)phenyl)-4,4-dimethyltetrahydrofuran-3-yl)formamide [7.1c]

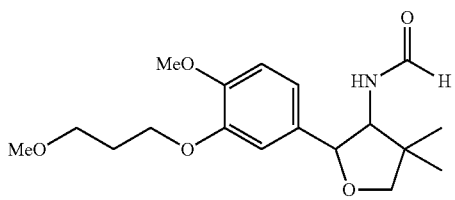

A 250 mL round-bottomed flask was charged with 7.1b (3.7 g, 12.00 mmol) and MeOH (30.0 ml). NH$_4$OAc (18.50 g, 240 mmol), was added, followed by NaBH$_3$CN (2.262 g, 36.0 mmol). The flask was fitted with a condenser and refluxed overnight. At 20 h, the mixture was cooled to rt and 30 mL 20 wt % NaOH (aq) was added. After stirring for 1 h, diluted slightly with water, extracted thrice with 2-MeTHF. The combined organic layers were dried over Na$_2$SO$_4$, filtered and concentrated to provide a heterogenous mixture. The mixture was taken up in DCM (30.0 ml). NEt$_3$ (10.03 ml, 71.9 mmol) was added, followed by formic acid (1.840 ml, 48.0 mmol) and EDC (9.19 g, 48.0 mmol). At 1 h complete, the mixture was poured into 20 mL water, 60 mL EtOAc and the layer separated. The organic layer was washed twice with N NaHSO$_4$, once with brine, dried over Na$_2$SO$_4$, filtered and concentrated onto diatomaceous earth. The crude material was purified on a 40 g RediSep SiO$_2$ cartridge (0->70% acetone in heptane) to provide 7.1c (2.58g, 7.65 mmol, 63.8% yield) as a yellow oil. LC-MS (m/z): 338.3 [M+H]$^+$.

Step 4: rac-(3aR,9bR)-7-methoxy-8-(3-methoxypropoxy)-3,3-dimethyl-2,3,3a,9b-tetrahydrofuro[3,2-c]isoquinoline [7.1d]

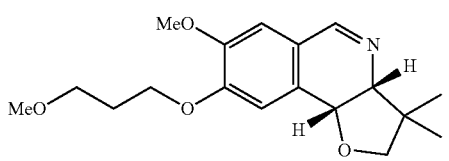

A 200 mL round-bottomed flask was charged with 7.1c (2.6 g, 7.71 mmol) and purged with N$_2$. MeCN (30.8 ml), followed by POCl₃ (1.077 ml, 11.56 mmol). The flask was fitted with a condenser and then heated to 70° C. At 30 min, the mixture was cooled to rt and the volatiles were removed under reduced pressure. The oil was diluted with EtOAc and water, and basisified with sat. aq. NH₄OH to pH 11. The layers were separated, and the aqueous layer extracted twice with EtOAc. The combined organic layers were dried over Na₂SO₄, filtered, and concentrate onto 6g diatomaceous earth. The crude material was purified on a 40 g RediSep SiO₂ cartridge (0->70% acetone in heptane). The most polar UV-active peak was isolated as 7.1d (900 mg, 2.82 mmol, 36.6% yield), which was shown to be the cis isomer by 2D NMR. LC-MS (m/z): 320.3 [M+H]⁺. ¹H NMR (500 MHz, CDCl₃) δ 8.27 (s, 1H), 6.98 (s, 1H), 6.86 (s, 1H), 4.97 (d, J=7.33 Hz, 1H), 4.14-4.23 (m, 2H), 3.87-3.94 (m, 4H), 3.48-3.60 (m, 3H), 3.39 (d, J=7.80 Hz, 1H), 3.35 (s, 3H), 2.12 (quin, J=6.33 Hz, 2H), 1.37 (s, 3H), 1.14 (s, 3H).

Step 5: rac-ethyl (3aR,12bR)-8-fluoro-10-methoxy-11-(3-methoxypropoxy)-3,3-dimethyl-7-oxo-3,3a,7,12b-tetrahydro-2H-furo[3,2-c]pyrido[2,1-a]isoquinoline-6-carboxylate [7.1e]

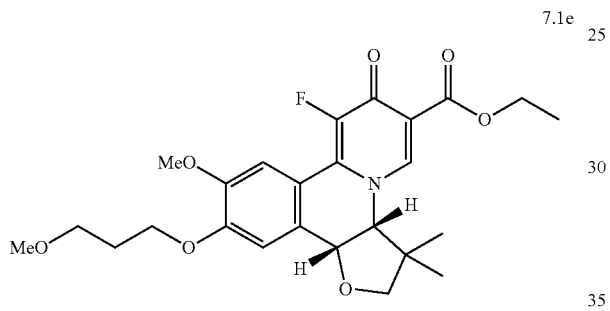

7.1e

To a suspension of ZnI₂ (200 mg, 0.626 mmol) and 7.1d (200 mg, 0.626 mmol) in dry MeCN (2 mL), was added a solution of 3.1a (553 mg, 1.879 mmol) in dry DMF (3 mL), dropwise, at 50° C., and the reaction mixture was stirred overnight. The reaction mixture was poured into 10% HCl and extracted with DCM. The organic layer was washed with brine, and dried over MgSO₄. After filtration, the organic layer was concentrated onto diatomaceous earth and purified on a 4 g RediSep SiO₂ cartridge (0->60 IPA in EtOAc) to provide 7.1e (90 mg, 0.184 mmol, 30.6% yield) as a brown solid. LC-MS (m/z): 476.3 [M+H]⁺.

Step 6: (3aR,12bR)-8-fluoro-10-methoxy-11-(3-methoxypropoxy)-3,3-dimethyl-7-oxo-3,3a,7,12b-tetrahydro-2H-furo[3,2-c]pyrido[2,1-a]isoquinoline-6-carboxylic acid [7.1]

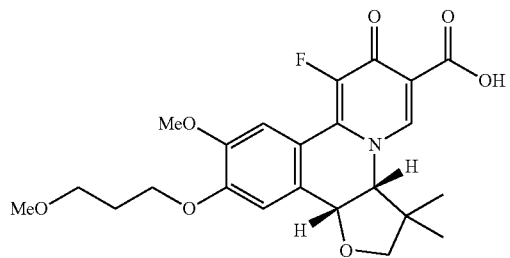

7.1

7.1g (90 mg, 0.189 mmol) was suspended in THF (1.5 ml). Aq. LiOH (500 μl, 1.000 mmol) was added and the mixture was stirred overnight. The pH was adjusted to 1 with 4 N HCl. The mixture was extracted thrice with EtOAc. The combined organic layers were dried over Na₂SO₄, filtered and concentrated to provide a light brown solid. The material was purified by chiral SFC (AD column, flow rate 100 ml/min, CO₂/MeOH=80/20, 250 bar) to give two enantiomers 7.1 (tR 4.56, 17.7 mg, 21%) and 7.2 (tR 2.89 min, 17.3 mg, 21%). Compound 7.1: LC-MS (m/z): 448.3 [M+H]⁺. ¹H NMR (500 MHz, CDCl₃): 8.36 (s, 1H), 7.72 (s, 1H), 7.21 (s, 1H), 5.54 (d, J=7.6 Hz, 1H) 4.42 (d, J=6.4 Hz, 1H), 4.16-4.31 (m, 2H) 3.92 (s, 3H), 3.78 (d, J=8.5 Hz, 1H), 3.52-3.69 (m, 2H), 3.42 (br d, J=9.22 Hz, 1H), 3.37 (s, 3H), 2.10-2.22 (m, 2H), 1.40 (s, 3H) 0.58 (s, 3H)

Example 8: (3aS,12bR)-10-methoxy-11-(3-methoxypropoxy)-3,3-dimethyl-7-oxo-3,3a,7,12b-tetrahydro-1H-furo[3,4-c]pyrido[2,1-a]isoquinoline-6-carboxylic acid [8.1]

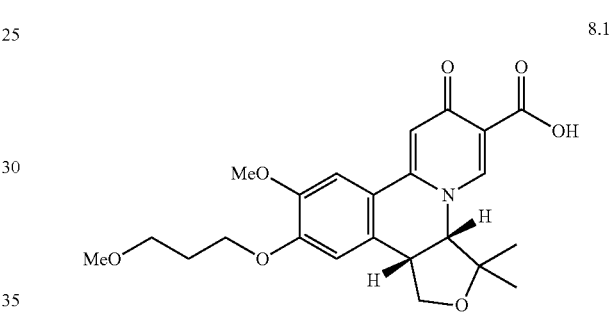

8.1

Step 1: 3-hydroxy-1-(4-methoxy-3-(3-methoxypropoxy)phenyl)-3-methylbutan-2-one [8.1a]

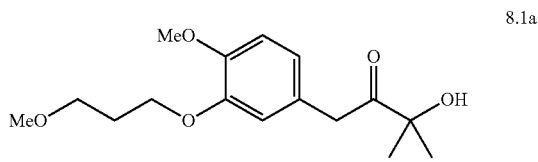 [SMILES: COCCCOc1cc(CC(=O)C(C)(C)O)ccc1OC]

8.1a

A 200 mL round-bottomed flask was charged with 4-bromo-1-methoxy-2-(3-methoxypropoxy)benzene (13.0 g, 47.2 mmol), NaOt-Bu (13.62 g, 142 mmol), xantphos (0.820 g, 1.417 mmol), Pd₂dba₃ (0.649 g, 0.709 mmol) and THF (Volume: 140 mL). To the mixture was added 3-hydroxy-3-methylbutan-2-one (9.65 g, 94 mmol). The flask was fitted with a reflux condenser and the mixture was heated to 65° C. in an aluminum chip bath for 3.5 h. After cooling, the mixture was filtered through diatomaceous earth with EtOAc and water washes. The pH of the aqueous layer was adjusted to 2, the layers were separated, and the aqueous layer extracted twice with EtOAc. The combined organic layers were dried over Na₂SO₄, filter, and concentrated onto 6 g diatomaceous earth. The material was purified by silica gel column chromatography, EtOAc/heptane 0 to 70% to give product (5.7g, 19.23 mmol, 40.7% yield). LC-MS (m/z): 297.3 [M+H]⁺.

Step 2: 4-(4-methoxy-3-(3-methoxypropoxy)phenyl)-2,2-dimethylfuran-3(2H)-one [8.1b]

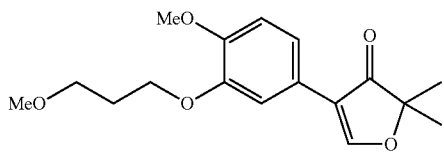

8.1a (1.43 g, 4.83 mmol) was dissolved in toluene (19.30 ml). Bredereck's reagent (1.993 ml, 8.69 mmol) was added, and the flask fitted with reflux condenser and heated to 100° C. for 1 h. After cooling to rt, 3 g of diatomaceous earth was added and the volatiles were removed. The material was purified by silica gel column chromatography, EtOAc/heptane 0 to 50% to provide product 8.1b (1.26g, 85% yield) as a yellow oil. LC-MS (m/z): 307.2 [M+H]$^+$. $^1$H NMR (500 MHz, CHLOROFORM-d): 8.39 (s, 1H), 7.31 (d, J=1.89 Hz, 1H), 7.22 (dd, J=8.35, 2.05 Hz, 1H), 6.88 (d, J=8.20 Hz, 1H), 4.16 (s, 2H), 3.87 (s, 3H), 3.58 (s, 2H), 3.36 (s, 3H), 2.13 (quin, J=6.38 Hz, 2H), 1.46 (s, 6H).

Step 3: 4-(4-methoxy-3-(3-methoxypropoxy)phenyl)-2,2-dimethyldihydrofuran-3(2H)-one [8.1c]

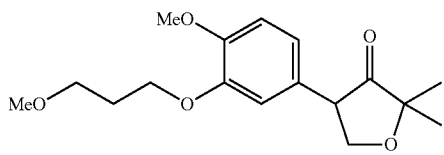

8.1b (1.26g, 4.11 mmol) was taken up in EtOH (10.28 ml) and THF (10.28 ml). The mixture was cooled to 0° C. and NaBH$_4$ (0.202 g, 5.35 mmol) was added. After 2 h, the reaction was quenched with saturated aq. NH$_4$Cl and extracted with EtOAc. The combined organic layers were dried over Na$_2$SO$_4$, filtered and concentrated to provide an oil. The oil was charged to a 100 mL round-bottomed flask and dissolved in DCM (32 mL). The mixture was cooled to 0° C. and DMP (4104 mg, 9.68 mmol) was added as a single portion. After 2 h, the reaction mixture was filter through diatomaceous earth with DCM and sat. aq. NaHCO$_3$. The layers were separated. The aqueous layer was extract twice with DCM. The combined organic layers were dried over Na$_2$SO$_4$, filtered and concentrated to provide a yellow oil which was purified by silica gel column chromatography, EtOAc/heptane 0 to 70% to give product 8.1c (841 mg, 42.3% yield). LC-MS (m/z): 309.2 [M+H]$^+$.

Step 4: N-(4-(4-methoxy-3-(3-methoxypropoxy)phenyl)-2,2-dimethyltetrahydrofuran-3-yl)formamide [8.1d]

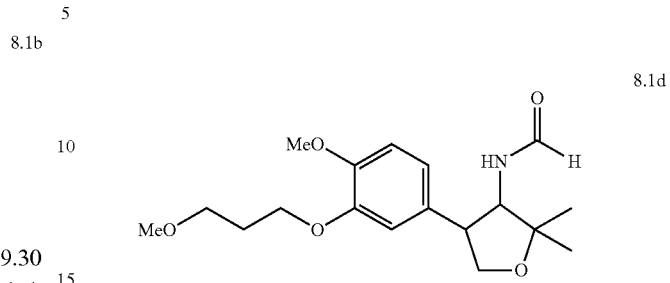

A 20 mL vial was charged with 8.1c (840 mg, 2.72 mmol) and methanol (8 ml). Ammonium acetate (3.15 g, 40.9 mmol) was added and the mixture stirred until homogeneous. Sodium cyanoborohydride (0.342 g, 5.45 mmol) was added as a single portion. The yellow solution was stirred overnight at 60° C. At 20 h, The mixture was cool to rt and quenched with 6 mL 5 M NaOH (20 wt %). After 1 h, the mixture was extracted with EtOAc twice, dried over Na$_2$SO$_4$, filtered and concentrated to provide a yellow oil. The oil was taken up in formic acid (5.0 ml, 130 mmol) and dioxane (7 ml) in an 8 mL vial. The vial was sealed and heated to 98° C. 18 h. The volatiles were removed under reduced pressure ° (50 C, 18 mbar) and the resultant oil azeotroped twice with 30 mL toluene before a final concentration onto diatomaceous earth with MeOH and DCM. The crude material was purified by silica gel column chromatography, acetone/heptane 0->50% to give product 8.1d (230 mg, 25.1% yield) as a white solid. LC-MS (m/z): 338.1 [M+H]$^+$.

Step 5: 7-methoxy-8-(3-methoxypropoxy)-3,3-dimethyl-1,3,3a,9b-tetrahydrofuro[3,4-c]isoquinoline [8.1e]

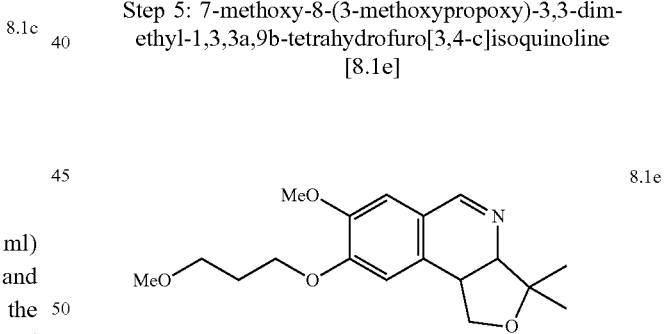

A 50 mL round-bottomed flask was charged with 8.1d (230 mg, 0.682 mmol) and purged with vacuum and back-filled with nitrogen. MeCN (3.41 ml) was added, followed by POCl$_3$ (0.095 ml, 1.022 mmol). The flask was fitted with a condenser and heated to 70° C. At 2 h, cooled to rt and the volatiles were removed under vacuum. The remaining oil was diluted with 40 mL EtOAc, and 10 mL water, and then basified with ammonium hydroxide solution until pH 11. The layers were separated, and the aqueous layer extracted EtOAc. The combined organic layers were dried over Na$_2$SO$_4$, filtered and concentrated onto diatomaceous earth. The crude material was purified by silica gel column chromatography, acetone/heptane 0 to 50%, to give product 8.1e (202 mg, 93% yield). LC-MS (m/z): 320.2 [M+H]$^+$.

Step 6: ethyl (3aS,12bR)-10-methoxy-11-(3-methoxypropoxy)-3,3-dimethyl-7-oxo-3,3a,7,12b-tetrahydro-1H-furo[3,4-c]pyrido[2,1-a]isoquinoline-6-carboxylate [8.1f]

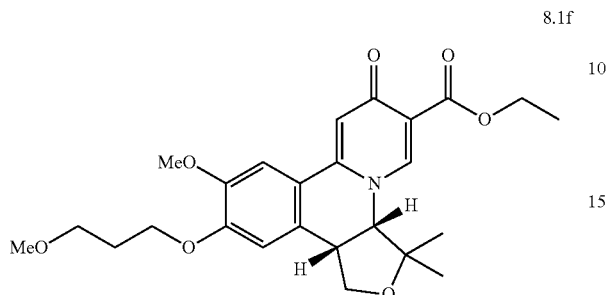

A 4 mL vial was charged with 8.1e (200 mg, 0.626 mmol) in EtOH (1.5 ml). Added ethyl (E)-2-(ethoxymethylene)-3-oxobutanoate (408 mg, 2.192 mmol). The vial was sealed, purged with N2, and heated to 85° C. overnight. An additional 400 mg ethyl (E)-2-(ethoxymethylene)-3-oxobutanoate was added. After 5 h, the volatiles were removed under vacuum. The oil was taken up in DME (1.3 mL) and p-chloranil (185 mg) was added. The mixture was heated at 100° C. for 30 min. After cooling at rt, the solvent was removed on rotovap and 5 mL ether was added and the solid filtered. The black solid was taken up in MeOH and loaded onto diatomaceous earth, and then purified by silica gel column chromatography, IPA/EtOAc 0 to 70 to give product. The stereoisomers were separated by chiral HPLC (AD column, flow rate 1 mL/min, heptane/IPA=60/40). Peak 3 (tR 6.76 min) was isolated as 8.1f (13.5 mg, 0.030 mmol, 4.71% yield). LC-MS (m/z): 458.4 [M+H]$^+$.

Step 7: (3aS,12bR)-10-methoxy-11-(3-methoxypropoxy)-3,3-dimethyl-7-oxo-3,3a,7,12b-tetrahydro-1H-furo[3,4-c]pyrido[2,1-a]isoquinoline-6-carboxylic acid [8.1]

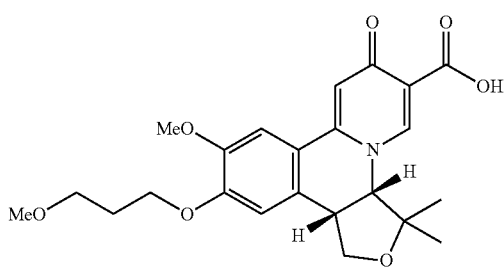

To a solution of 8.1f (12.5 mg, 0.027 mmol) in THF (1 mL) was added NaOH (0.022 mL, 0.109 mmol) and stirred overnight. The solution was acidified by adding 4.0 N HCl aq solution and extracted with EtOAc. The combined organic layers were dried over Na$_2$SO$_4$ and concentrated to provide a yellow oil, which was purified by HPLC (Kinetex column, 0.1% TFA in H$_2$O/MeCN, 1.2 mL/min) to provide 8.1 (7.8 mg, 52%). $^1$H NMR (500 MHz, DMSO-d$_6$): 8.62 (s, 1H), 7.64 (s, 1H), 7.57 (s, 1H), 7.11 (s, 1H), 5.04 (br d, J=8.75 Hz, 1H), 4.40 (br dd, J=9.81, 1.30 Hz, 1H), 4.17-4.26 (m, 3H), 4.11 (dt, J=9.75, 6.47 Hz, 2H), 3.94-4.00 (m, 1H), 3.91 (s, 3H), 3.50 (br t, J=6.27 Hz, 2H), 3.27 (s, 3H), 2.00 (dt, J=12.65, 6.21 Hz, 2H), 1.39 (s, 3H), 0.64 (s, 3H). LC-MS (m/z): 430.1 [M+H]$^+$.

Example 9: Synthesis 11-methoxy-12-(3-methoxypropoxy)-4,4-dimethyl-8-oxo-2,3,4,4a,8,13b-hexahydro-1H-pyrido[1,2-f]phenanthridine-7-carboxylic acid [9.1] and [9.2]

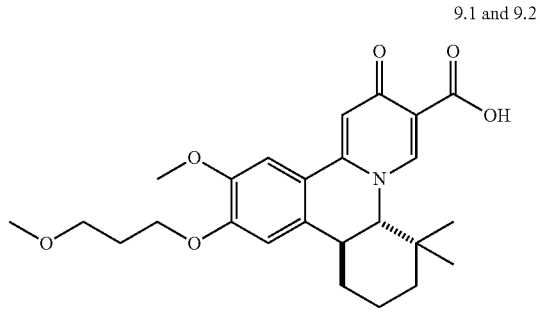

Step 1: 6-(4-methoxy-3-(3-methoxypropoxy) phenyl)-2,2-dimethylcyclohexanone [9.1a]

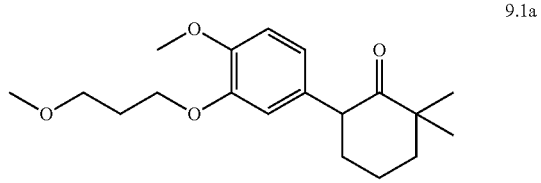

A mixture of Pd(OAc)$_2$ (14 mg, 0.064 mmol), sodium tert-butoxide (0.795 g, 8.27 mmol), dicyclohexyl(2'-methyl-[1,1'-biphenyl]-2-yl)phosphane (58 mg), 2,2-dimethylcyclohexanone (1.056 ml, 7.63 mmol) and 4-bromo-1-methoxy-2-(3-methoxypropoxy)benzene (1.75 g, 6.36 mmol) in toluene (6.0 ml) was heated in a sealed vial under nitrogen atmosphere at 50° C. for 18 hours. The mixture was diluted with EtOAc and washed with sat sodium bicarbonate. The organic layer was separated, dried over Na$_2$SO$_4$, filtrated and concentrated. The remaining oil was purified by silica gel column chromatography, EtOAc/heptane 5 to 50%, to give product (1 g, 49.1% yield). LC-MS (m/z): 321.2 [M+H]$^+$.

Step 2: 6-(4-methoxy-3-(3-methoxypropoxy)phenyl)-2,2-dimethylcyclohexan-1-amine [9.1b]

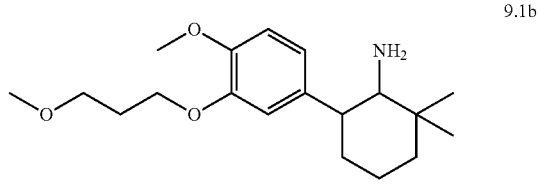

To the mixture of 5-(4-methoxy-3-(3-methoxypropoxy) phenyl)-2,2-dimethylcyclohexanone (500 mg, 1.56 mmol) in MeOH (5 ml) was added acetic acid ammonia salt (2.4 g, 31.2 mmol) and sodium cyanoborohydride (981 mg, 15.4 mmol). The mixture was stirred at 70° C. for 8 hours and then was concentrated under reduced pressure. The remaining material was diluted with EtOAc, washed with water and brine, dried over Na$_2$SO$_4$ and concentrated. The crude material was used in the next step without further purification. LCMS (m/z): 322.0 [M+H]$^+$.

Step 3: N-(5-(4-methoxy-3-(3-methoxypropoxy) phenyl)-2,2 dimethylcyclohexyl)formamide [9.1c]

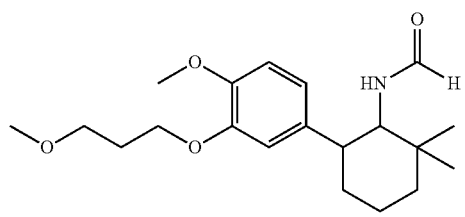

9.1c

To the mixture of 5-(4-methoxy-3-(3-methoxypropoxy) phenyl)-2,2-dimethylcyclohexamine (500 mg, 1.56 mmol) in dioxane (5 ml) was added formic acid (0.286 mL, 6.22 mmol). The mixture was stirred at 100° C. for 6 hours. The mixture was concentrated to afford the crude product which was used in the next step without further purification. LCMS (m/z): 350.2 [M+H]$^+$.

Step 4: 8-methoxy-9-(3-methoxypropoxy)-4,4-dimethyl-1,2,3,4,4a,10b-hexahydrophenanthridine [9.1d]

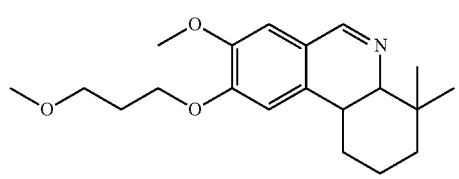

9.1d

To a mixture of N-(5-(4-methoxy-3-(3-methoxypropoxy) phenyl)-2,2-dimethylcyclohexyl)formamide (543 mg, 1.54 mmol) in acetonitrile (3 ml) was added POCl$_3$ (217 µl, 2.33 mmol). The mixture was stirred at 85° C. for 2 hours and then concentrated. The residue was dissolved in EtOAc and basified by ammonium hydroxide solution. The phases were separated and the organic layer was washed with brine, dried over Na$_2$SO$_4$ and concentrated. The remaining material was purified by silica gel chromatography, acetone/heptane 5 to 50% to give the title product. (320 mg, 62% yield). LCMS (m/z): 332.3 [M+H]$^+$.

Step 5: Ethyl (11-methoxy-12-(3-methoxypropoxy)-4,4-dimethyl-8-oxo-2,3,4,4a,8,9,9a,13b-octahydro-1H-pyrido[1,2-f]phenanthridine-7-carboxylate [9.1e]

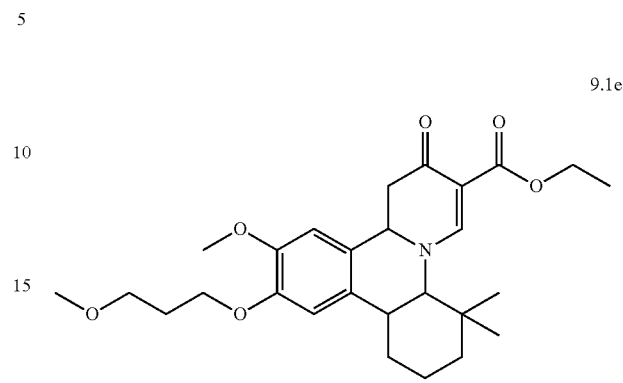

9.1e

To a mixture of 8-methoxy-9-(3-methoxypropoxy)-4,4-dimethyl-1,2,3,4,4a,10b-hexahydrophenanthridine (140 mg, 0.422 mmol) in EtOH (1.6 ml) was added (Z)-ethyl 2-(ethoxymethylene)-3-oxobutanoate (236 mg, 1.267 mmol). The mixture was stirred at 110° C. for 16 hours. After cooling, the mixture was concentrated and the crude material was used in the next step without further purification. LCMS (m/z): 472.0 [M+H]$^+$.

Step 6: Ethyl 11-methoxy-12-(3-methoxypropoxy)-4,4-dimethyl-8-oxo-2,3,4,4a,8,13b-hexahydro-1H-pyrido[1,2-f]phenanthridine-7-carboxylate [9.1f]

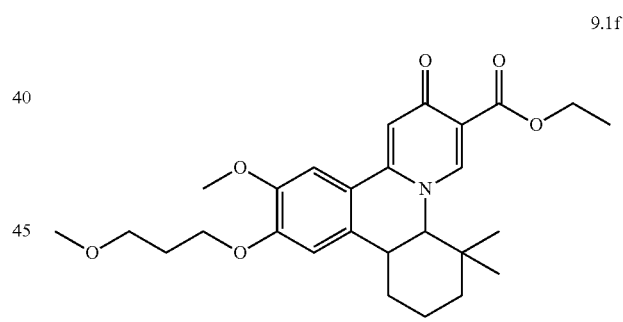

9.1f

To a mixture of 9.1e (199.7 mg, 0.422 mmol) in DME (1.0 ml) was added p-chloranil (114.6 mg, 0.464 mmol). The mixture was stirred at 110° C. for 2 hours. After cooling to rt, the mixture was filtered and the solid was washed with cold DME. After drying, the desired product (100 mg, 50.5% yield over two steps) was obtained as a light yellow solid. LCMS (m/z): 470.0 [M+H]$^+$.

Step 7: 11-methoxy-12-(3-methoxypropoxy)-4,4-dimethyl-8-oxo-2,3,4,4a,8,13b-hexahydro-1H-pyrido[1,2-f]phenanthridine-7-carboxylic acid [9.1] and [9.2]

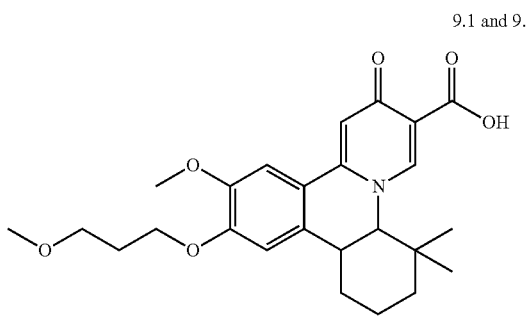

9.1 and 9.2

To a mixture of 9.1f (50 mg, 0.106 mmol) in THF (0.6 ml), MeOH (0.6 ml) and water (0.6 ml) was added LiOH (7.7 mg, 0.319 mmol). After stirring at rt for 2 hours, the mixture was concentrated and then acidified by adding 3.0 N HCl aq solution. To the resultant mixture was added EtOAc. The organic layer was washed with water and brine, dried, and concentrated. The crude residue was purified by reverse phase HPLC to give product (10 mg, 21% yield). LCMS (m/z): 442.2 [M+H]$^+$. H NMR (400 MHz, Acetonitrile-d3): 9.15 (s, 1H), 7.11 (s, 1H), 6.98 (s, 1H), 4.15 (dt, J=9.3, 4.7 Hz, 2H), 3.91 (s, 3H), 3.71 (d, J=12.4 Hz, 1H), 3.53 (t, J=6.2 Hz, 2H), 3.32 (s, 3H), 2.98 (td, J=12.2, 5.2 Hz, 1H), 2.74-2.54 (m, 1H), 2.12-2.00 (m, 2H), 1.96 (dt, J=4.5, 2.4 Hz, 5H), 1.46 (d, J=29.8 Hz, 9H).

The relative configuration of the product was established to be as shown below by nuclear Overhauser effect (NOE) experiments, but the absolute stereochemistry of each enantiomer has not been confirmed.

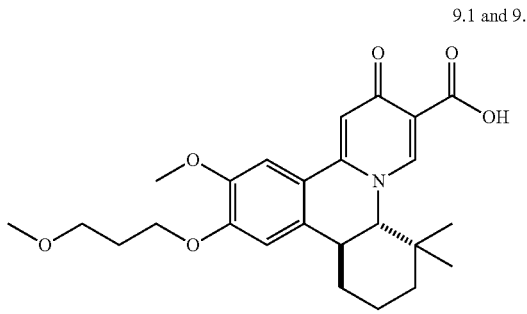

9.1 and 9.2

The racemic material was separated by chiral SFC (OD column, flow rate 100 ml/min, CO$_2$/MeOH=70/30) to give two enantiomers: 9.1 (tR 3.93 min) and 9.2 (tR 6.14 min).

The following compounds can be made by similar methods using starting materials that are known in the art:

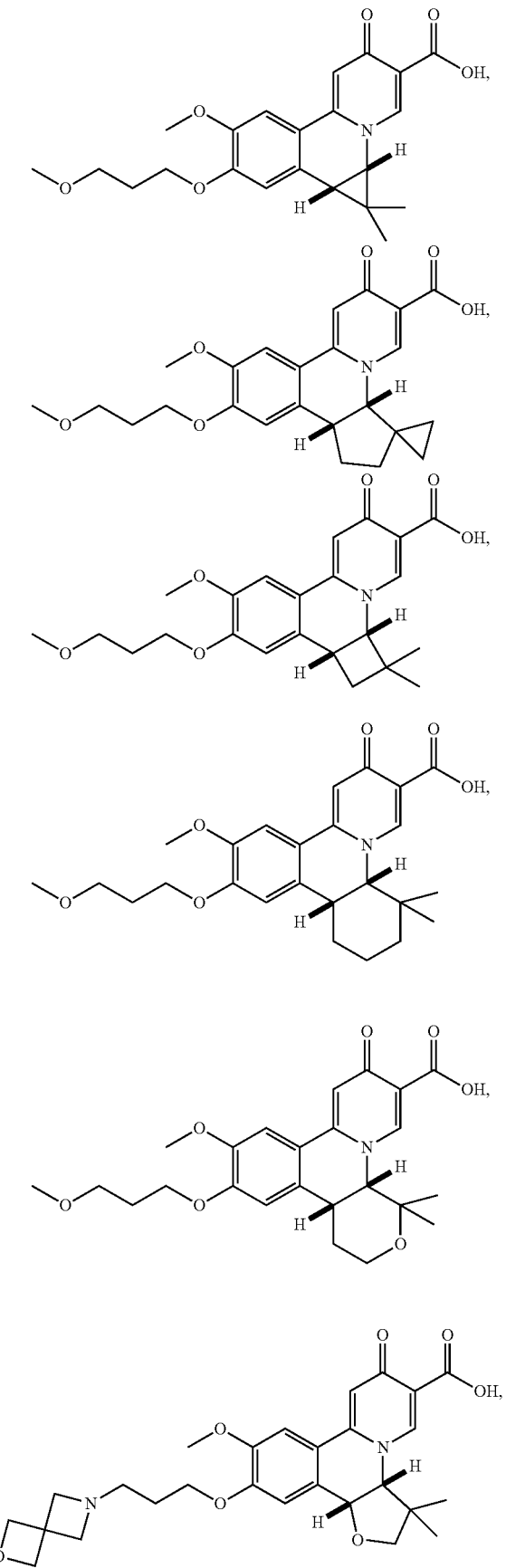

69
-continued
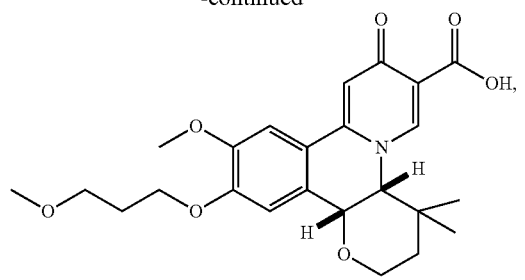
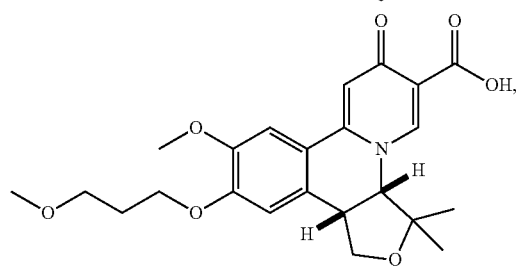
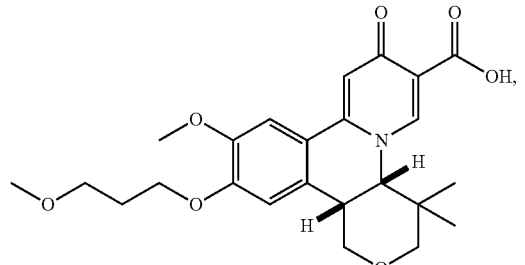
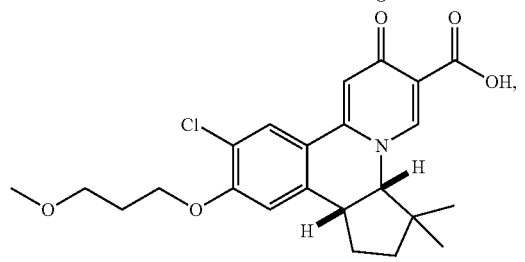
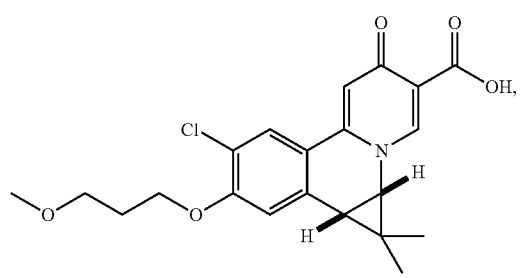
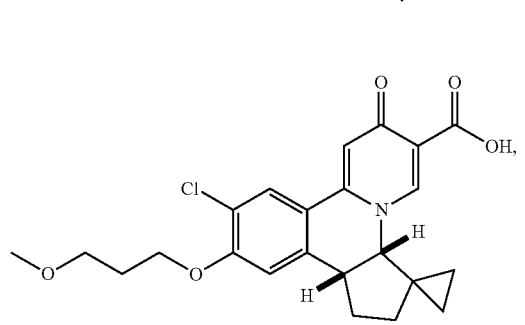
70
-continued
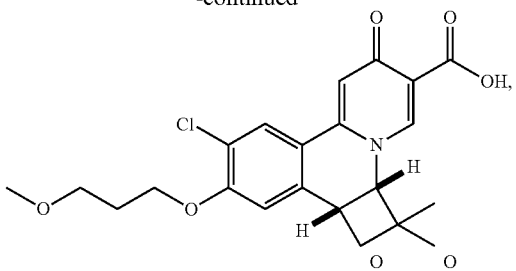
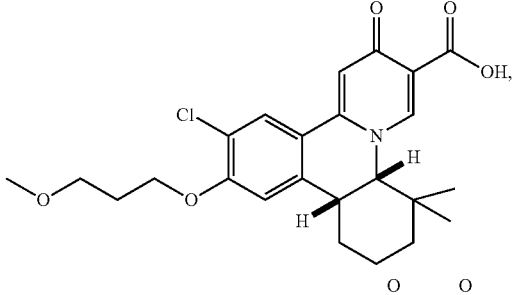
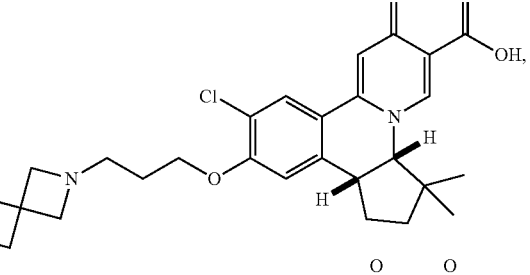
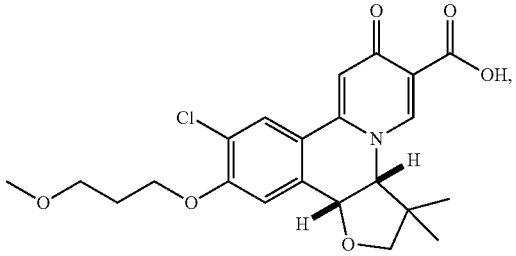
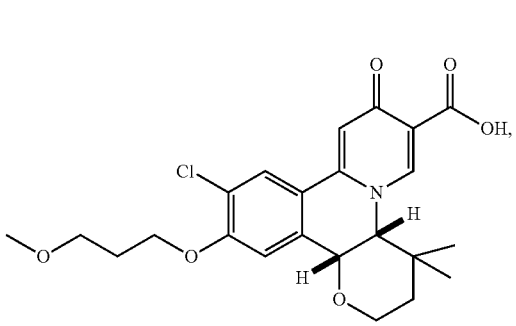

71
-continued
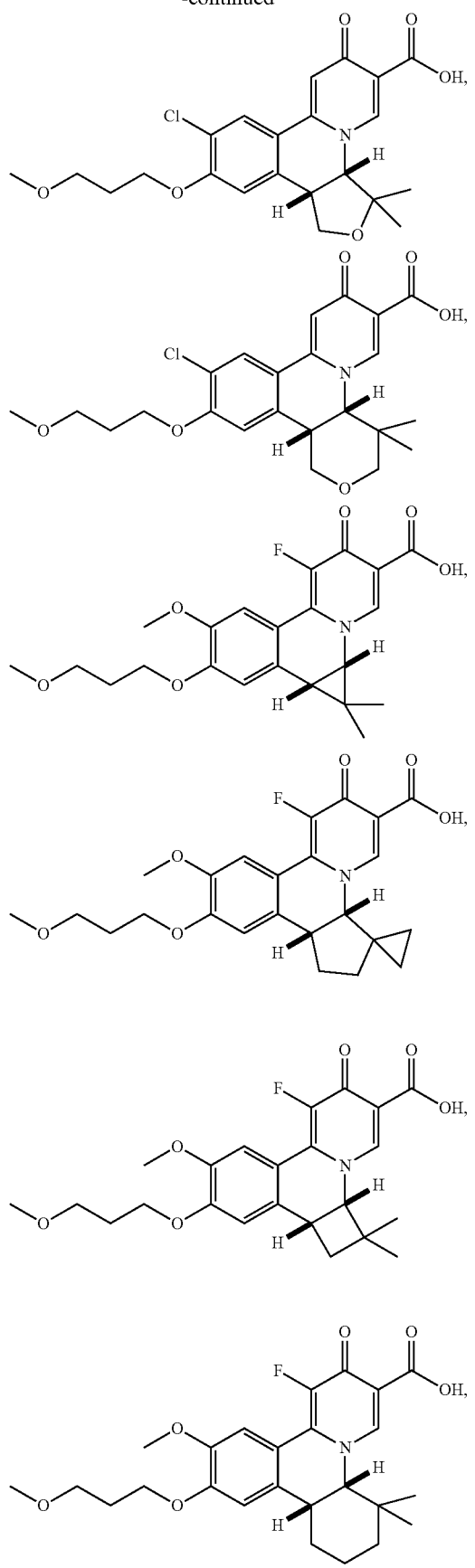
72
-continued
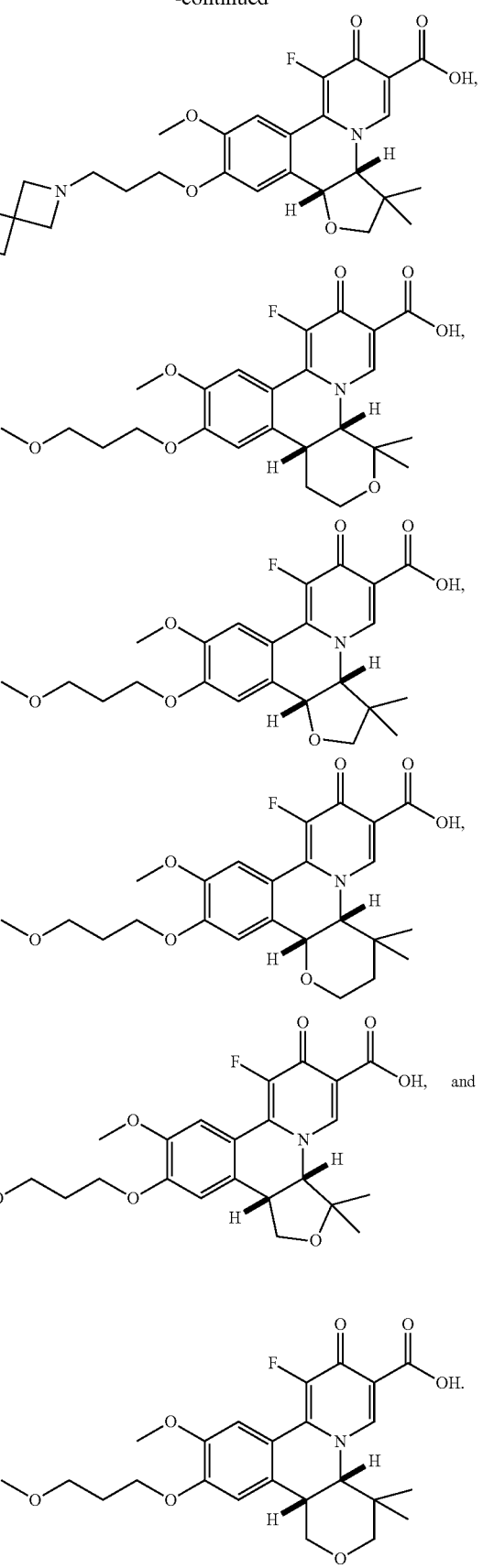

Biological Examples

HBV Cell Line

HepG2-Clone42, a Tet-inducible HBV-expressing cell line with a stably integrated 1.3mer copy of the HBV ayw strain, was generated based on the Tet-inducible HepAD38 cell line with slight modifications. Ladner S K, et al., *Antimicrobial Agents and Chemotherapy.* 41(8):1715-1720 (1997). HepG2-Clone42 cells were cultured in DMEM/F-12+Glutamax™ (Life Technologies, Carlsbad, Calif., USA), supplemented with 10% fetal bovine serum (Life Technologies), G-418 (Corning, Manassas, Va., USA) at a final concentration of 0.5 mg/mL, and 5 µg/mL Doxycycline (Sigma, St. Louis, Mo., USA) and maintained in 5% $CO_2$ at 37° C.

HBsAq Assay

HepG2-Clone42 cells were seeded in into black clear-bottom 96-well plates at a concentration of $6.0 \times 10^4$ cells/well. 24 hours post-seeding, the cells were treated with 200 µl/well of media containing five-fold serial dilutions of compounds in DMSO. DMSO alone was used as the no drug control. The final DMSO concentration in all wells was 0.5%.

The HBsAg ELISA kit (Alpha Diagnostic International, San Antonio, Tex., USE, Catalog #4110) was used to determine the level (semi-quantitative) of secreted HBV sAg.

The HBSAg ELISA assay was performed following the manufacturer's protocol as described.

Step 1. Pipet 100 µL each of compound or DMSO treated samples into HBsAg ELISA plates. Seal plates and incubate at room temp for 60 minutes.

Step 2. Aspirate samples and wash three times with Wash Buffer. Dispense 100µ of antibody-HRP conjugate to each well. Incubate at room temp for 30 minutes.

Step 3. Aspirate samples and wash three times with Wash Buffer. Add 100 µL of TMB Substrate to all wells and incubate 15 minutes at room temp.

Step 4. Dispense 100 µL of Stop Solution to each well. Measure absorbance of ELISA plate at 450 nm.

Dose Response Curves

Dose-response curves were generated and the $EC_{50}$ value was defined as the compound concentration at which HBsAg secretion was reduced 50% compared to the DMSO control.

$EC_{50}$ values were determined as follows:

1. Determine the percent of HBsAg secretion inhibition. Calculate the percent inhibition on of HBsAg secretion inhibition using the following equation:

$$100 \times (X_C - M_B)/(M_D - M_B)$$

where $X_C$ is the absorbance signal from compound-treated well; $M_B$ is average absorbance signal (background signal) for column 12 (no cells+HBsAg ELISA sample buffer) and $M_D$ is average absorbance signal from DMSO-treated wells. Then calculate $EC_{50}$ values by non-linear regression using a four parameter curve logistic equation.

The curve fit model employed is XLFit Dose Response One Site Model 204: $y=(A+((B-A)/(1+(10^{((C-x)*D)}))))$ where A is the minimum y value, B is the maximum y value, C is the log EC50 value, and D is the slope factor.

High Throughput Solubility Measurement

1. Transfer 20 ul of 10 mM DMSO stock solution into a 96 deep well plate labeled as sample plate and 5 ul to another plate labeled as compound standard plate.
2. Place the buffer plate in a Multi-Tainer MT-4 container (FTS Systems). Freeze dry overnight to remove DMSO.
3. Add 100 ul of Cl-free PBS (pH 6.8) to the dried compound in the buffer plate and 95 ul of DMSO to the standard plate.
4. The buffer plate is be sonicated in a water bath for 10 min.
5. The two plates are then placed onto the VWR orbital shaker to equilibrate for 24 hours at room temperature.
6. The buffer plate is centrifuged at 4000 rpm for 30 min.
7. Transfer 10 ul aliquots of supernatant from the buffer plate to a sample plate and dilute 5 fold.
8. Inject both compound standard and sample into the UPLC/UV/CLND/MS to generate multi detector qualitative and quantitive analytical data.
9. Data was processed with Xcalibur. CLND equimolar response was used for measuring compound concentration of DMSO solution. UV270 nm or MS relative ratio was used for solubility determination.

TABLE 1

| Compound | Structure | HBsAg $EC_{50}$ (nM) |
|---|---|---|
| 1.1 | 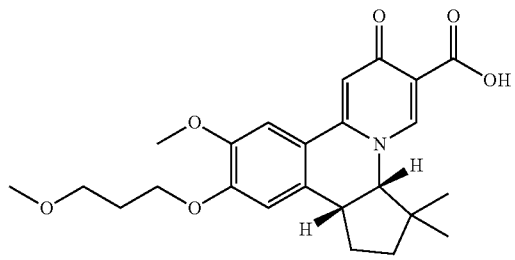 [SMILES: COCCCOc1cc2c(cc1OC)-c1cc(=O)c(C(=O)O)cn1[C@H]1[C@@H]2CCC1(C)C] | 0.1 |

TABLE 1-continued

| | HBsAg inhibition | |
|---|---|---|
| Compound | Structure | HBsAg EC$_{50}$ (nM) |
| 1.2 | | 13 |
| rac-2 | | 460 |
| 3.1 | | 0.3 |
| 3.2 | | 740 |
| 4.1 | | 0.3 |

TABLE 1-continued

| | HBsAg inhibition | |
|---|---|---|
| Compound | Structure | HBsAg EC$_{50}$ (nM) |
| 5.1 | | 6 |
| 5.2 | | 0.1 |
| 6.1 | | 9 |
| 6.2 | | 5 |
| 7.1 | | 0.8 |

TABLE 1-continued

HBsAg inhibition

| Compound | Structure | HBsAg EC$_{50}$ (nM) |
|---|---|---|
| 7.2 | 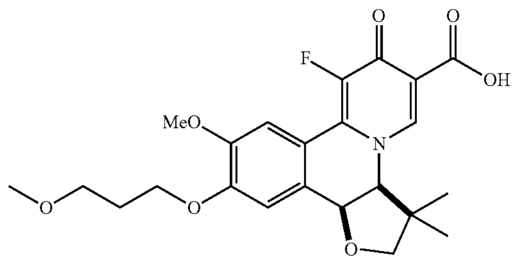 | 90 |
| 8.1 | 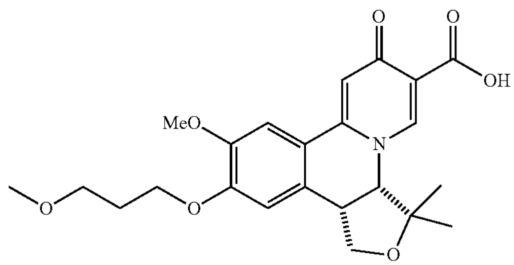 | 1 |
| 9.1 | 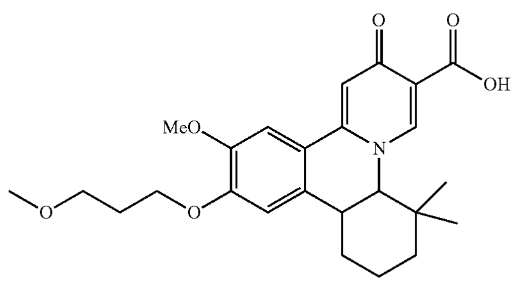 [SMILES: COCCCOc1cc2c(cc1OC)-c1cc(=O)c(C(=O)O)cn1C1C2CCCC1(C)C] | 9 |
| 9.2 | 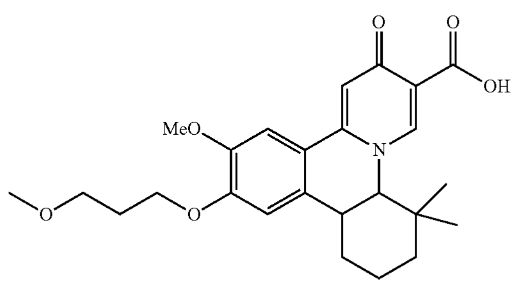 [SMILES: COCCCOc1cc2c(cc1OC)-c1cc(=O)c(C(=O)O)cn1C1C2CCCC1(C)C] | 303 |

TABLE 2

Pharmacokinetic data for selected compounds.
Compound 1.1

| | Mice[a] | Rat[b] | Dog[c] |
|---|---|---|---|
| CL (mL/min · kg) | 24.6 | 15.3 | 6.4 |
| Vss (L/kg) | 3.6 | 1.3 | 1.7 |
| T$_{1/2term.}$ (h)* | 1.6 | 2.4 | 5.9 |
| AUC (uM · h) iv | 1.5 | 2.5 | 3.1 |
| AUC (uM · h) PO | 1.7 | 4.5 | 5.7 |
| C$_{max}$ (uM) PO | 0.57 | 1.72 | 1.9 |
| T$_{max}$ p.o. (h) | 0.5 | 1.33 | 0.22 |
| Oral BA (% F) | 59 | 97 | 93 |

[a] iv 1.0 mg/kg, PO 2.0 mg/kg. Formulation: solution in D5W with PEG (20%) and solutol (5%)
[b] iv 1.0 mg/kg, PO 2.0 mg/kg. Formulation: solution in D5W with PEG (20%) and solutol (5%)
[c] iv 0.5 mg/kg, PO 1.0 mg/kg. Formulation: solution in D5W with PEG (20%) and solutol (5%)

Compound 3.1

|  | Mice[a] | Rat[b] | Dog[c] |
|---|---|---|---|
| CL (mL/min · kg) | 6.9 | 2.1 | 1.3 |
| Vss (L/kg) | 1.0 | 0.6 | 0.6 |
| $T_{1/2term.}$ (h)* | 3.8 | 9.2 | 7.2 |
| AUC (uM · h) iv | 5.5 | 16.6 | 13.3 |
| AUC (uM · h) po | 9.5 | 19.6 | 26.7 |

-continued

|  | Mice[a] | Rat[b] | Dog[c] |
|---|---|---|---|
| $C_{max}$ (uM) PO | 3.0 | 6.5 | 6.2 |
| $T_{max}$ p.o. (h) | 0.5 | 0.5 | 1.5 |
| Oral BA (% F) | 87 | 57 | 96 |

[a]iv 1.0 mg/kg, PO 2.0 mg/kg. Formulation: solution in D5W with PEG (20%) and solutol (5%)
[b]iv 1.0 mg/kg, PO 2.0 mg/kg. Formulation: solution in D5W with PEG (20%) and solutol (5%)
[c]iv 0.5 mg/kg, PO 1.0 mg/kg. Formulation: solution in D5W with PEG (20%) and solutol (10%)

|  | Mice[a] | Rat[b] | Dog[c] |
|---|---|---|---|
| CL (mL/min · kg) | 12.7 | 4.9 | 2.7 |
| Vss (L/kg) | 1.5 | 0.75 | 1.7 |
| $T_{1/2term.}$ (h)* | 1.8 | 1.2 | 12.3 |
| AUC (uM · h) iv | 2.9 | 8.0 | 6.2 |
| AUC (uM · h) PO | 7.2 | 10.2 | 12.8 |
| $C_{max}$ (uM) PO | 1.9 | 2.6 | 3.3 |
| $T_{max}$ p.o. (h) | 1.0 | 2.0 | 0.8 |
| Oral BA (% F) | 100 | 65 | 94 |

[a]iv 1.0 mg/kg, PO 2.0 mg/kg. Formulation: solution in D5W with PEG (20%) and solutol (5%)
[b]iv 1.0 mg/kg, PO 2.0 mg/kg. Formulation: 75% PEG300 and 25% D5W
[c]iv 0.5 mg/kg, PO 1.0 mg/kg. Formulation: solution in D5W with 20% PEG and 10% solutol Comparative Data The following table provides data for solubility of compounds of the invention in PBS (phosphate-buffered saline), using a standard solubility screening method. It also provides data for inhibition of a key cardiac sodium ion channel for selected compounds: inhibition of Nav1.5 is often associated with cardiotoxicity, thus compounds that exhibit little or no inhibition of this sodium channel are less likely to cause adverse effects than compounds that inhibit Nav1.5, and are predicted to be more suitable for development as drugs. Thus the compound of Example 4.1 is predicted to be safer in this respect than the reference compound.

Each of the compounds of the invention exhibited solubility greater than 1 mM in PBS buffer. Compounds with higher solubility possess lower risks in achieving the toxicological end points (in animals) and the oral development pathway (for human) in terms of the bioavailability criteria. A compound of similar structure (Ref. Ex. #132 from WO2015/113990) lacking the fused ring of the claimed compounds, was about 20-fold less soluble; thus the fused ring provides compounds with improved physical properties for formulation and/or development.

| Example No. | Solubility (mM) | Nav1.5 $EC_{50}$ (uM) |
|---|---|---|
| 1.1 | 2.4 | |
| 3.1 | 1.6 | |
| 4.1 | 1.6 | >500 |
| | 0.086 | 46 |

(Ref. Example #132)

The invention claimed is:
1. A compound having the formula:

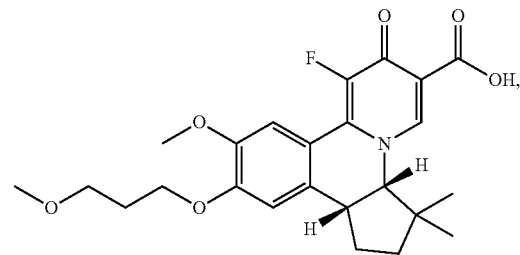 [SMILES: COCCCOc1cc2c(cc1OC)-c1c(F)c(=O)c(C(=O)O)cn1[C@H]1[C@@H]2CCC1(C)C]

or a pharmaceutically acceptable salt thereof.

2. A compound having the formula:

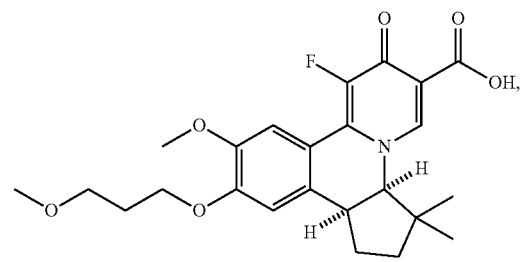 [SMILES: COCCCOc1cc2c(cc1OC)-c1c(F)c(=O)c(C(=O)O)cn1[C@@H]1[C@H]2CCC1(C)C]

or a pharmaceutically acceptable salt thereof.

3. A compound having the formula:

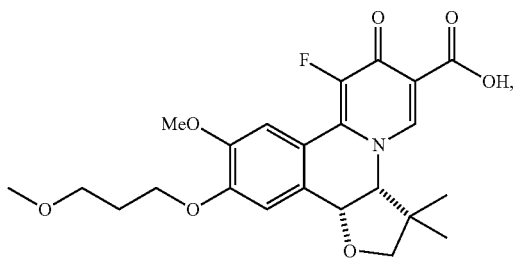

or a pharmaceutically acceptable salt thereof.

4. A compound having the formula:

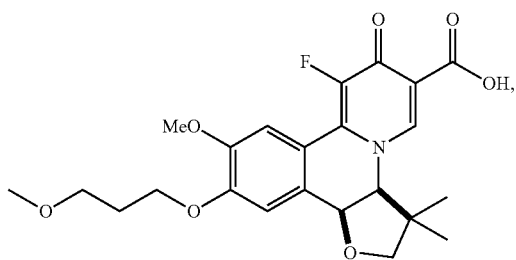

or a pharmaceutically acceptable salt thereof.

5. A pharmaceutical composition, comprising a compound of claim 1 admixed with at least one pharmaceutically acceptable carrier.

6. A method to treat a hepatitis B infection, which comprises administering to a patient having a hepatitis B infection a compound of claim 1.

7. The method of claim 6, wherein the compound of claim 1 is used in combination with an additional therapeutic agent selected from an interferon or peginterferon, an HBV polymerase inhibitor, a viral entry inhibitor, a viral maturation inhibitor, a capsid assembly inhibitor, an HBV core modulator, a reverse transcriptase inhibitor, a TLR-agonist, or an immunomodulator.

8. A pharmaceutical composition, comprising a compound of claim 2 admixed with at least one pharmaceutically acceptable carrier.

9. A method to treat a hepatitis B infection, which comprises administering to a patient having a hepatitis B infection a compound of claim 2.

10. The method of claim 9, wherein the compound of claim 2 is used in combination with an additional therapeutic agent selected from an interferon or peginterferon, an HBV polymerase inhibitor, a viral entry inhibitor, a viral maturation inhibitor, a capsid assembly inhibitor, an HBV core modulator, a reverse transcriptase inhibitor, a TLR-agonist, or an immunomodulator.

11. A pharmaceutical composition, comprising a compound of claim 3 admixed with at least one pharmaceutically acceptable carrier.

12. A method to treat a hepatitis B infection, which comprises administering to a patient having a hepatitis B infection a compound of claim 3.

13. The method of claim 12, wherein the compound of claim 3 is used in combination with an additional therapeutic agent selected from an interferon or peginterferon, an HBV polymerase inhibitor, a viral entry inhibitor, a viral maturation inhibitor, a capsid assembly inhibitor, an HBV core modulator, a reverse transcriptase inhibitor, a TLR-agonist, or an immunomodulator.

14. A pharmaceutical composition, comprising a compound of claim 4 admixed with at least one pharmaceutically acceptable carrier.

15. A method to treat a hepatitis B infection, which comprises administering to a patient having a hepatitis B infection a compound of claim 4.

16. The method of claim 15, wherein the compound of claim 4 is used in combination with an additional therapeutic agent selected from an interferon or peginterferon, an HBV polymerase inhibitor, a viral entry inhibitor, a viral maturation inhibitor, a capsid assembly inhibitor, an HBV core modulator, a reverse transcriptase inhibitor, a TLR-agonist, or an immunomodulator.

* * * * *